(12) United States Patent
Chin et al.

(10) Patent No.: US 8,067,442 B2
(45) Date of Patent: Nov. 29, 2011

(54) HETEROCYCLIC ANTIVIRAL COMPOUNDS

(75) Inventors: Elbert Chin, San Jose, CA (US); Jim Li, San Francisco, CA (US); Francisco Xavier Talamas, Mountain View, CA (US); Beihan Wang, Shanghai (CN)

(73) Assignee: Roche Palo Alto LLC, South San Francisco, CA (US)

( * ) Notice: Subject to any disclaimer, the term of this patent is extended or adjusted under 35 U.S.C. 154(b) by 222 days.

(21) Appl. No.: 12/566,896

(22) Filed: Sep. 25, 2009

(65) Prior Publication Data
US 2010/0081658 A1 Apr. 1, 2010

Related U.S. Application Data

(60) Provisional application No. 61/194,469, filed on Sep. 26, 2008.

(51) Int. Cl.
*A61K 31/44* (2006.01)
*C07D 401/14* (2006.01)

(52) U.S. Cl. ...................... 514/337; 546/279.1

(58) Field of Classification Search ............... 546/279.1; 514/337
See application file for complete search history.

(56) References Cited

U.S. PATENT DOCUMENTS
2010/0021423 A1 1/2010 Brameld et al.

FOREIGN PATENT DOCUMENTS

| WO | WO00/09543 A2 | 2/2000 |
|---|---|---|
| WO | WO01/85172 A1 | 11/2001 |
| WO | 2009032116 A1 | 3/2009 |
| WO | 2009032123 A2 | 3/2009 |
| WO | 2009032125 A1 | 3/2009 |
| WO | 2009039127 A1 | 3/2009 |
| WO | 2009039134 A1 | 3/2009 |
| WO | WO2009/039135 A1 | 3/2009 |
| WO | 2009064848 A1 | 5/2009 |
| WO | 2009064852 A1 | 5/2009 |
| WO | WO2010/111436 A2 | 9/2010 |
| WO | WO2010/111437 A1 | 9/2010 |

*Primary Examiner* — Rebecca Anderson
(74) *Attorney, Agent, or Firm* — Brian L. Buckwalter

(57) ABSTRACT

Compounds having the formula I wherein $R^1$, $R^{2a}$, $R^{2b}$, $R^{2c}$, $R^3$, Y and p are as defined herein and C2-C3 is a single or double bond are Hepatitis C virus NS5b polymerase inhibitors. Also disclosed are compositions and methods for treating an HCV infection and inhibiting HCV replication.

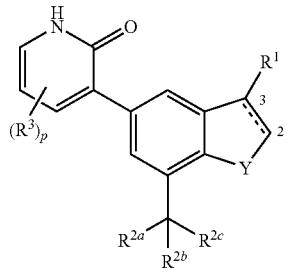

12 Claims, No Drawings

HETEROCYCLIC ANTIVIRAL COMPOUNDS

CROSS REFERENCE TO PRIOR APPLICATIONS

This application claims the benefit of priority to U.S. Ser. No. 61/194,469 filed Sep. 26, 2008 which are hereby incorporated by reference in their entirety.

FIELD OF THE INVENTION

The present invention provides 3-(7-alkyl-benzofuran-5-yl)-1H-pyridin-2-one and 3-[7-(1-alkyl-cyclopropyl)-benzofuran-5-yl]-1H-pyridin-2-one compounds and derivatives thereof which are inhibitors of RNA-dependent RNA viral polymerase. These compounds are useful for the treatment of RNA-dependent RNA viral infection. They are particularly useful as inhibitors of hepatitis C virus (HCV) NS5B polymerase, as inhibitors of HCV replication, and for the treatment of hepatitis C infection.

BACKGROUND

Hepatitis C virus is the leading cause of chronic liver disease throughout the world. (Boyer, N. et al., *J. Hepatol.* 2000 32:98-112). Patients infected with HCV are at risk of developing cirrhosis of the liver and subsequent hepatocellular carcinoma and hence HCV is the major indication for liver transplantation.

HCV has been classified as a member of the virus family Flaviviridae that includes the genera flaviviruses, pestiviruses, and hapaceiviruses which includes hepatitis C viruses (Rice, C. M., Flaviviridae: The viruses and their replication. In: Fields Virology, Editors: B. N. Fields, D. M. Knipe and P. M. Howley, Lippincott-Raven Publishers, Philadelphia, Pa., Chapter 30, 931-959, 1996). HCV is an enveloped virus containing a positive-sense single-stranded RNA genome of approximately 9.4 kb. The viral genome consists of a highly conserved 5' untranslated region (UTR), a long open reading frame encoding a polyprotein precursor of approximately 3011 amino acids, and a short 3' UTR.

Genetic analysis of HCV has identified six main genotypes which diverge by over 30% of the DNA sequence. More than 30 subtypes have been distinguished. In the US approximately 70% of infected individuals have Type 1a and 1b infection. Type 1b is the most prevalent subtype in Asia. (X. Forms and J. Bukh, *Clinics in Liver Disease* 1999 3:693-716; J. Bukh et al., *Semin. Liv. Dis.* 1995 15:41-63). Unfortunately Type 1 infectious is more resistant to therapy than either type 2 or 3 genotypes (N. N. Zein, *Clin. Microbiol. Rev.*, 2000 13:223-235).

Viral structural proteins include a nucleocapsid core protein (C) and two envelope glycoproteins, E1 and E2. HCV also encodes two proteases, a zinc-dependent metalloproteinase encoded by the NS2-NS3 region and a serine protease encoded in the NS3 region. These proteases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of nonstructural protein 5) remain unknown. It is believed that most of the non-structural proteins encoded by the HCV RNA genome are involved in RNA replication.

Currently a limited number of approved therapies are available for the treatment of HCV infection. New and existing therapeutic approaches for treating HCV infection and inhibiting of HCV NS5B polymerase activity have been reviewed: R. G. Gish, *Sem. Liver. Dis.,* 1999 19:5; Di Besceglie, A. M. and Bacon, B. R., *Scientific American,* October: 1999 80-85; G. Lake-Bakaar, Current and Future Therapy for Chronic Hepatitis C Virus Liver Disease, *Curr. Drug Targ. Infect Dis.* 2003 3(3):247-253; P. Hoffmann et al., Recent patent on experimental therapy for hepatitis C virus infection (1999-2002), *Exp. Opin. Ther. Patents* 2003 13(11):1707-1723; M. P. Walker et al., Promising Candidates for the treatment of chronic hepatitis C, *Exp. Opin. Investig. Drugs* 2003 12(8): 1269-1280; S.-L. Tan et al., Hepatitis C Therapeutics: Current Status and Emerging Strategies, *Nature Rev. Drug Discov.* 2002 1:867-881; J. Z. Wu and Z. Hong, Targeting NS5B RNA-Dependent RNA Polymerase for Anti-HCV Chemotherapy, *Curr. Drug Targ.—Infect. Dis.* 2003 3(3):207-219.

Ribavirin (1-((2R,3R,4S,5R)-3,4-Dihydroxy-5-hydroxymethyl-tetrahydro-furan-2-yl)-1H-[1,2,4]triazole-3-carboxylic acid amide; Virazole®) is a synthetic, non-interferon-inducing, broad-spectrum antiviral nucleoside analog. Ribavirin has in vitro activity against several DNA and RNA viruses including Flaviviridae (Gary L. Davis. *Gastroenterology* 2000 118:S104-S114). Although, in monotherapy ribavirin reduces serum amino transferase levels to normal in 40% of patients, it does not lower serum levels of HCV-RNA. Ribavirin also exhibits significant toxicity and is known to induce anemia. Viramidine is a ribavirin prodrug converted ribavirin by adenosine deaminase to in hepatocytes. (J. Z. Wu, *Antivir. Chem. Chemother.* 2006 17(1):33-9)

Interferons (IFNs) have been available for the treatment of chronic hepatitis for nearly a decade. IFNs are glycoproteins produced by immune cells in response to viral infection. Two distinct types of interferon are recognized: Type 1 includes several interferon alphas and one interferon beta, type 2 includes interferon gamma. Type 1 interferons are produced mainly by infected cells and protect neighboring cells from de novo infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary. Cessation of therapy results in a 70% relapse rate and only 10-15% exhibit a sustained virological response with normal serum alanine transferase levels. (Davis, Luke-Bakaar, supra)

One limitation of early IFN therapy was rapid clearance of the protein from the blood. Chemical derivatization of IFN with polyethyleneglycol (PEG) has resulted in proteins with substantially improved pharmacokinetic properties. PEGASYS® is a conjugate interferon –2a and a 40 kD branched mono-methoxy PEG and PEG-INTRON® is a conjugate of interferon –2b and a 12 kD mono-methoxy PEG. (B. A. Luxon et al., *Clin. Therap.* 2002 24(9):13631383; A. Kozlowski and J. M. Harris, *J. Control. Release* 2001 72:217-224).

Combination therapy of HCV with ribavirin and interferon-α currently is the optimal therapy for HCV. Combining ribavirin and PEG-IFN (infra) results in a sustained viral response (SVR) in 54-56% of patients with type 1 HCV. The SVR approaches 80% for type 2 and 3 HCV. (Walker, supra) Unfortunately, combination therapy also produces side effects which pose clinical challenges. Depression, flu-like symptoms and skin reactions are associated with subcutaneous IFN-α and hemolytic anemia is associated with sustained treatment with ribavirin.

A number of potential molecular targets for drug development as anti-HCV therapeutics have now been identified including, but not limited to, the NS2-NS3 autoprotease, the NS3 protease, the NS3 helicase and the NS5B polymerase.

The RNA-dependent RNA polymerase is absolutely essential for replication of the single-stranded, positive sense, RNA genome. This enzyme has elicited significant interest among medicinal chemists.

Nucleoside inhibitors can act either as a chain terminator or as a competitive inhibitor that interferes with nucleotide binding to the polymerase. To function as a chain terminator the nucleoside analog must be taken up by the cell in vivo and be converted in vivo to its triphosphate form to compete as a substrate at the polymerase nucleotide binding site. This conversion to the triphosphate is commonly mediated by cellular kinases which impart additional structural limitations on any nucleoside. In addition this requirement for phosphorylation limits the direct evaluation of nucleosides as inhibitors of HCV replication to cell-based assays (J. A. Martin et al., U.S. Pat. No. 6,846,810; C. Pierra et al., *J. Med. Chem.* 2006 49(22):6614-6620; J. W. Tomassini et al., *Antimicrob. Agents and Chemother.* 2005 49(5):2050; J. L. Clark et al., *J. Med. Chem.* 2005 48(17):2005).

Compounds of the present invention and their isomeric forms and pharmaceutically acceptable salts thereof are also useful in treating viral infections, in particular, hepatitis C infection, and diseases in living hosts when used in combination with each other and with other biologically active agents, including but not limited to the group consisting of interferon, a pegylated interferon, ribavirin, protease inhibitors, polymerase inhibitors, small interfering RNA compounds, antisense compounds, nucleotide analogs, nucleoside analogs, immunoglobulins, immunomodulators, hepatoprotectants, anti-inflammatory agents, antibiotics, antivirals and antiinfective compounds. Such combination therapy may also comprise providing a compound of the invention either concurrently or sequentially with other medicinal agents or potentiators, such as ribavirin and related compounds, amantadine and related compounds, various interferons such as, for example, interferon-alpha, interferon-beta, interferon gamma and the like, as well as alternate forms of interferons such as pegylated interferons. Additionally combinations of ribavirin and interferon, may be administered as an additional combination therapy with at least one of the compounds of the present invention.

Other interferons currently in development include albinterferon-α-2b (Albuferon), IFN-omega with DUROS, LOCTERON™ and interferon-α-2b XL. As these and other interferons reach the marketplace their use in combination therapy with compounds of the present invention is anticipated.

HCV polymerase inhibitors are another target for drug discovery and compounds in development include R-1626, R-7128, IDX184/IDX102, PF-868554 (Pfizer), VCH-759 (ViroChem), GS-9190 (Gilead), A-837093 and A-848837 (Abbot), MK-3281 (Merck), GSK949614 and GSK625433 (Glaxo), ANA598 (Anadys), VBY 708 (ViroBay).

Inhibitors of the HCV NS3 protease also have been identified as potentially useful for treatment of HCV. Protease inhibitors in clinical trials include VX-950 (Telaprevir, Vertex), SCH503034 (Broceprevir, Schering), TMC435350 (Tibotec/Medivir) and ITMN-191 (Intermune). Other protease inhibitors in earlier stages of development include MK7009 (Merck), BMS-790052 (Bristol Myers Squibb), VBY-376 (Virobay), IDXSCA/IDXSCB (Idenix), BI12202 (Boehringer), VX-500 (Vertex), PHX1766 Phenomix).

Other targets for anti-HCV therapy under investigation include cyclophilin inhibitors which inhibit RNA binding to NS5b, nitazoxanide, Celgosivir (Migenix), an inhibitor of α-glucosidase-1, caspase inhibitors, Toll-like receptor agonists and immunostimulants such as Zadaxin (SciClone).

SUMMARY OF THE INVENTION

There is currently no preventive treatment of Hepatitis C virus (HCV) and currently approved therapies, which exist only against HCV, are limited. Design and development of new pharmaceutical compounds is essential.

The present invention provides a compound according to formula I, or a pharmaceutically acceptable salt thereof, wherein:

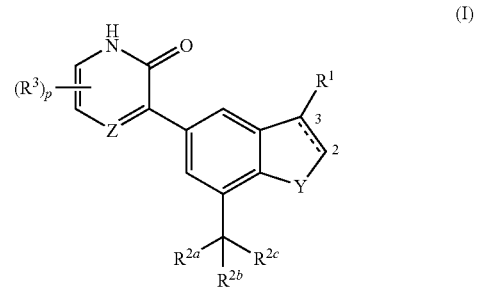

(I)

the bond between C2 and C3 is either a single or double bond;

Z is N or CH;

$R^1$ is hydrogen, $C_{1-6}$ hydroxyalkyl, $-(CR^7_2)_m COX$, $-(CR^7_2)_m CN$, $C_{1-3}$ hydroxyalkyl, phenyl or heteroaryl wherein said heteroaryl is pyridinyl, pyrimidinyl, pyrazinyl or pyridazinyl and said phenyl or said heteroaryl is optionally independently substituted with one to three substituent selected from the group consisting of hydroxy, $C_{1-6}$ alkoxy, $C_{1-6}$ alkyl, $C_{1-6}$ haloalkyl, $C_{1-6}$ heteroalkyl, $C_{1-3}$ alkoxy-$C_{1-6}$ alkyl, $-(CR^7_2)_m NR^a R^b$, cyano, nitro, $-(CR^7_2)_m COR^4$, $-(CR^7_2)_m SO_2 NR^c R^d$ and $-O(CR^7_2)_m COR^4$;

$R^{2a}$, $R^{2b}$ and $R^{2c}$ (i) when taken independently are selected independently from $C_{1-3}$ alkyl, $C_{1-2}$ alkoxy, fluoro or $C_{1-2}$ fluoroalkyl or (ii) when taken together, $R^{2a}$ and $R^{2b}$ together are $C_{2-4}$ methylene and $R^{2c}$ is $C_{1-3}$ alkyl, $C_{1-2}$ alkoxy or $C_{1-2}$ fluoroalkyl;

$R^3$ is independently in each occurrence halogen, $C_{1-3}$ alkyl, $C_{1-3}$ haloalkyl or $C_{1-3}$ alkoxy;

$R^4$ is hydroxy, $C_{1-6}$ alkoxy or $NR^c R^d$;

$R^5$ is hydrogen $C_{1-6}$ alkyl, $C_{1-3}$ acyl, $C_{1-3}$ alkylsulfonyl or $SO_2 NR^i R^j$;

$R^7$ is independently in each occurrence hydrogen or $C_{1-3}$ alkyl;

X is hydroxy, $C_{1-6}$ alkoxy, $NR^e R^f$, phenyl or heteroaryl wherein said heteroaryl is pyridinyl, thienyl or furanyl and said phenyl and said heteroaryl are optionally substituted with one to three substituents independently selected from hydroxyl, $C_{1-3}$ alkyl, $C_{1-3}$ alkoxy or halogen;

$R^a$ and $R^b$ (i) when taken independently are hydrogen, $C_{1-3}$ alkyl, $C_{1-3}$ hydroxyalkyl, $C_{1-3}$ acyl, $C_{1-6}$ alkylsulfonyl, $C_{3-7}$ cycloalkylsulfonyl, $-SO_2-NR^c R^d$ wherein at least one of $R^a$ and $R^b$ is hydrogen, $C_{1-3}$ hydroxyalkyl or $C_{1-3}$ alkyl, or, (ii) $R^a$ and $R^b$ when taken together with the nitrogen atom to which they are attached form a pyrrolidine, piperidine or azepine ring said pyrrolidine, piperidine or azepine ring optionally substituted with 1 to 3 groups independently selected from hydroxy, amino, $C_{1-3}$ alkylamine, $C_{1-3}$ dialkylamine, amino-$C_{1-3}$ alkyl, $C_{1-3}$ alkylamine-$C_{1-3}$ alkyl or $C_{1-3}$ dialkylamine-$C_{1-3}$ alkyl, carboxyl, halogen or $C_{1-3}$ alkyl; or, (iii) $R^a$ and $R^b$ together are $(CH_2)_2 X^1 (CH_2)_2$;

$R^c$ and $R^d$ (i) when taken independently are hydrogen, $C_{1-3}$ alkyl; or, (ii) $R^c$ and $R^d$ when taken together along with the nitrogen atom to which they are attached form a pyrrolidine, piperidine or azepine ring; or, (iii) $R^c$ and $R^d$ together are $(CH_2)_2X^1(CH_2)_2$;

$R^e$ and $R^f$ (i) when taken independently are hydrogen, $C_{1-6}$ alkyl, $C_{1-3}$ alkoxy-$C_{1-3}$ alkyl, $C_{3-7}$ cycloalkyl, phenyl or thiazol-2-yl, said cycloalkyl ring optionally substituted by $C_{1-3}$ hydroxyalkyl, and said phenyl optionally substituted with hydroxy or $(CH_2)_mNR^gR^h$; or, (ii) $R^e$ and $R^f$ when taken together along with the nitrogen atom to which they are attached form an azetidine, pyrrolidine, piperidine, azepine, morpholine, pyrazolidin-1-yl, thiazolidin-3-yl, isothiazolidin-2-yl, isoxazolidin-2-yl or oxazolidin-3-yl ring each optionally substituted by one or two groups independently selected in each occurrence from halogen, hydroxy, $C_{1-3}$ alkyl, $C_{1-3}$ hydroxyalkyl, —$(CR^7_2)_mNR^gR^h$, —$(CR^7_2)_mCONR^gR^h$, —$(CR^7_2)_mSO_2$—$C_{1-3}$ alkyl or —$(CR^7_2)_mCOR^4$, or (iii) $R^e$ and $R^f$ together are $(CH_2)_2X^1(CH_2)_2$ or [1,4]diazepam-1-yl optionally substituted with $C_{1-3}$ hydroxyalkyl, $(CR^7_2)_mNR^gR^h$ or $C_{1-3}$ alkyl;

$R^g$ and $R^h$ (i) when taken independently are hydrogen, $C_{1-6}$ alkyl, $C_{1-6}$ haloalkyl, $C_{1-6}$ acyl, $C_{1-6}$ haloalkylcarbonyl, $C_{1-6}$ alkylsulfonyl, $C_{1-6}$ haloalkylsulfonyl, $C_{3-7}$ cycloalkylsulfonyl, phenylsulfonyl, —$SO_2$—$NR^iR^j$, or $C_{1-6}$ alkoxycarbonyl; or, (ii) $R^g$ and $R^h$ taken together are $(CH_2)_2X^2(CH_2)_2$ optionally substituted with $C_{1-3}$ hydroxyalkyl;

$R^i$ and $R^j$ are independently hydrogen or $C_{1-3}$ alkyl;

$X^1$ is independently $S(O)_n$ or $NR^5$;

$X^2$ are independently O, $S(O)_n$ or $NR^5$;

Y is O, S or $NR^7$; with the proviso that when the bond between C2 and C3 is a single bond, Y is O;

m is independently in each occurrence zero to three;

n is zero to two;

p is zero to two.

or a pharmaceutically acceptable salt thereof.

The present invention also provides a method for treating a disease caused by the Hepatitis C Virus (HCV) virus by administering a therapeutically effective quantity of a compound according to formula I to a patient in need thereof. The compound can be administered alone or co-administered with other antiviral compounds or immunomodulators.

The present invention also provides a method for inhibiting replication of HCV in a cell by administering a compound according to formula I in an amount effective to inhibit HCV.

The present invention also provides a pharmaceutical composition comprising a compound according to formula I and at least one pharmaceutically acceptable carrier, diluent or excipient.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "------" drawn through a bond each refer to the point of attachment of a functional group or other chemical moiety to the rest of the molecule of which it is a part. Thus, for example:

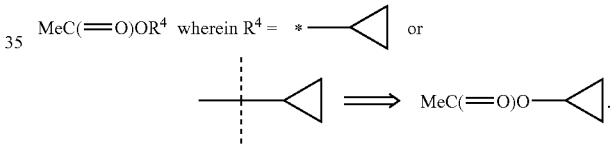

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, unless specifically indicated otherwise, the word "or" is used in the "inclusive" sense of "and/or" and not the "exclusive" sense of "either/or".

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

It will be appreciated by the skilled artisan that some of the compounds of formula I may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. It will be further appreciated by the skilled artisan that substitution of the tropane ring can be in either endo- or exo-configuration, and the present invention covers both configurations. The present invention includes all the individual stereoisomers (e.g. enantiomers), racemic mixtures or partially resolved mixtures of the compounds of formulae I and, where appropriate, the individual tautomeric forms thereof.

The racemates can be used as such or can be resolved into their individual isomers. The resolution can afford stereochemically pure compounds or mixtures enriched in one or more isomers. Methods for separation of isomers are well known (cf. Allinger N. L. and Eliel E. L. in "*Topics in Stereochemistry*", Vol. 6, Wiley Interscience, 1971) and include physical methods such as chromatography using a chiral adsorbent. Individual isomers can be prepared in chiral form from chiral precursors. Alternatively individual isomers can be separated chemically from a mixture by forming diastereomeric salts with a chiral acid, such as the individual enantiomers of 10-camphorsulfonic acid, camphoric acid, .alpha.-bromocamphoric acid, tartaric acid, diacetyltartaric acid, malic acid, pyrrolidone-5-carboxylic acid, and the like, fractionally crystallizing the salts, and then freeing one or both of the resolved bases, optionally repeating the process, so as to obtain either or both substantially free of the other; i.e., in a form having an optical purity of >95%. Alternatively the racemates can be covalently linked to a chiral compound (auxiliary) to produce diastereomers which can be separated by chromatography or by fractional crystallization after which time the chiral auxiliary is chemically removed to afford the pure enantiomers.

The compounds of formula I contain at least one basic center and suitable acid addition salts are formed from acids which form non-toxic salts. Examples of salts of inorganic acids include the hydrochloride, hydrobromide, hydroiodide, chloride, bromide, iodide, sulphate, bisulphate, nitrate, phosphate, hydrogen phosphate. Examples of salts of organic acids include acetate, fumarate, pamoate, aspartate, besylate, carbonate, bicarbonate, camsylate, D and L-lactate, D and L-tartrate, esylate, mesylate, malonate, orotate, glucepate, methylsulphate, stearate, glucuronate, 2-napsylate, tosylate, hibenzate, nicotinate, isethionate, malate, maleate, citrate, gluconate, succinate, saccharate, benzoate, esylate, and pamoate salts. For a review on suitable salts see Berge et al, *J. Pharm. Sic.*, 1977 66:1-19 and G. S. Paulekuhn et al. *J. Med. Chem.* 2007 50:6665.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). The starting materials and reagents used in preparing these compounds generally are either available from commercial suppliers, such as Aldrich Chemical Co., or are prepared by methods known to those skilled in the art following procedures set forth in references. Materials, reagents and the like to which reference are made in the following description and examples are obtainable from commercial sources, unless otherwise noted. General synthetic procedures have been described in treatise such as *Fieser and Fieser's Reagents for Organic Synthesis*; Wiley & Sons: New York, Volumes 1-21; R. C. LaRock, Comprehensive Organic Transformations, 2$^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40 and will be familiar to those skilled in the art.

In one embodiment of the invention there is provided a compound according to formula I wherein $R^1$, $R^{2a}$, $R^{2b}$, $R^{2c}$, $R^3$, $R^4$, $R^5$, $R^7$, $R^a$, $R^b$, $R^c$, $R^d$, $R^e$, $R^f$, $R^g$, $R^h$, $R^i$, $R^j$, X, $X^1$, $X^2$, Y, Z, m, n and p are as defined herein above. The phrase "as defined herein above" when referring to a variable incorporates by reference the broadest definition for each group as provided in the Summary of the Invention or the broadest claim. In all other embodiments provided below, substituents which can be present in each embodiment and which are not explicitly defined retain the broadest definition permitted in the Summary of the Invention.

In another embodiment of the present invention there is provided a compound according to formula I, or a pharmaceutically acceptable salt thereof, wherein: the bond between C2 and C3 is either a single or double bond. Z is CH. $R^1$ is —$(CR^7_2)_m$COX, —$(CR^7_2)_m$CN, $C_{1-3}$ hydroxyalkyl, phenyl or heteroaryl wherein said heteroaryl is pyridinyl, pyrimidinyl, pyrazinyl or pyridazinyl and said phenyl or said heteroaryl is optionally independently substituted with one to three substituent selected from the group consisting of hydroxy, $C_{1-6}$ alkoxy, hydroxy, halogen, $C_{1-6}$ alkyl, $C_{1-6}$ haloalkyl, $C_{1-6}$ hydroxyalkyl, $C_{1-3}$ alkoxy-$C_{1-6}$ alkyl, —$(CR^7_2)_m$NR$^a$R$^b$, cyano, nitro, —$(CR^7_2)_m$COR$^4$, —$(CR^7_2)_m$SO$_2$NR$^c$R$^d$ and —O$(CR^7_2)_m$COR$^4$. $R^{2a}$, $R^{2b}$ and $R^{2c}$ (i) when taken independently are selected independently from $C_{1-3}$ alkyl, $C_{1-2}$ alkoxy or $C_{1-2}$ fluoroalkyl or (ii) when taken together, $R^{2a}$ and $R^{2b}$ together are $C_{2-4}$ methylene and $R^{2c}$ is $C_{1-3}$ alkyl, $C_{1-2}$ alkoxy or $C_{1-2}$ fluoroalkyl. $R^3$ is independently in each occurrence halogen, $C_{1-3}$ alkyl, $C_{1-3}$ haloalkyl, $C_{1-3}$ alkoxy. $R^4$ is hydroxy, $C_{1-6}$ alkoxy or $NR^cR^d$. $R^5$ is hydrogen $C_{1-6}$ alkyl, $C_{1-3}$ acyl, $SO_2$—$C_{1-3}$ alkyl or —$SO_2NR^iR^j$. $R^6$ is hydroxy, $C_{1-6}$ alkoxy. $R^7$ is independently in each occurrence hydrogen or $C_{1-3}$ alkyl. X is hydroxy, $C_{1-6}$ alkoxy, $NR^eR^f$, phenyl or heteroaryl wherein said heteroaryl is pyridinyl, thienyl or furanyl and said phenyl and said heteroaryl are optionally substituted with one to three substituent independently selected from hydroxyl, $C_{1-3}$ alkyl, $C_{1-3}$ alkoxy or halogen. $R^a$ and $R^b$ (i) when taken independently are hydrogen, $C_{1-3}$ alkyl, $C_{1-3}$ hydroxyalkyl, $C_{1-3}$ acyl, —$SO_2$—$C_{1-6}$ alkyl; —$SO_2$—$C_{3-7}$-cycloalkyl, —$SO_2$—$NR^c$ $R^d$ wherein at least one of $R^a$ and $R^b$ is hydrogen, $C_{1-3}$ hydroxyalkyl or $C_{1-3}$ alkyl, or when taken together or (ii) $R^a$ and $R^b$ together with the nitrogen atom to which they are attached form a pyrrolidine, piperidine or azepine ring said pyrrolidine, piperidine or azepine ring optionally substituted with 1 to 3 groups independently selected from hydroxy, amino, $C_{1-3}$ alkylamine or $C_{1-3}$ dialkylamine, amino-$C_{1-3}$ alkyl, $C_{1-3}$ alkylamine-$C_{1-3}$ alkyl or $C_{1-3}$ dialkylamine-$C_{1-3}$ alkyl, carboxyl, halogen and $C_{1-3}$ alkyl; or, (iii) $R^a$ and $R^b$ together are $(CH_2)_2X^1(CH_2)_2$. $R^c$ and $R^d$ (i) when taken independently are hydrogen, $C_{1-3}$ alkyl, or when taken together, or (ii) $R^c$ and $R^d$ along with the nitrogen atom to which they are attached form a pyrrolidine, piperidine or azepine ring; or (iii) $R^a$ and $R^b$ together are $(CH_2)_2X^1(CH_2)_2$. $R^e$ and $R^f$ (i) when taken independently are hydrogen, $C_{1-6}$ alkyl, $C_{1-3}$alkoxy-$C_{1-3}$ alkyl $C_{3-7}$ cycloalkyl, phenyl; said cycloalkyl ring optionally substituted with one to four substituents independently selected from the group consisting of $C_{1-3}$ hydroxyalkyl; and said phenyl optionally substituted with hydroxy; or when taken together, or (ii) $R^e$ and $R^f$ along with the nitrogen atom to which they are attached form a pyrrolidine, piperidine, azepine, morpholinyl, pyrazolidin-1-yl, thiazolidin-3-yl, isothiazolidin-2-yl, isoxazolidin-2-yl or oxazolidin-3-yl ring optionally substituted by one or two groups independently selected in each occurrence from halogen, hydroxy, $C_{1-3}$ alkyl, $C_{1-3}$ hydroxyalkyl, $(CH_2)_mNR^gR^h$, —$(CH_2)_mCONR^gR^h$, or —$(CH_2)_mCOR$, or (iii) $R^e$ and $R^f$ together are $(CH_2)_2X^1(CH_2)_2$ optionally substituted with $C_{1-3}$ hydroxyalkyl or $C^{1-3}$ alkyl. $R^g$ and $R^h$ (i) when taken independently hydrogen, $C_{1-6}$ alkyl, $C_{1-6}$ haloalkyl, $C_{1-6}$ acyl, —$SO_2$ $C_{1-3}$ alkyl, —$SO_2$—$C_{3-7}$ cycloalkyl, —$SO_2$—$NR^iR^j$, $C_{1-6}$ alkoxycarbonyl or, (ii) $R^g$ and $R^h$ together are $(CH_2)_2$ $X^2(CH_2)_2$ optionally substituted with $C_{1-3}$ hydroxyalkyl. $R^i$ and $R^j$ are independently hydrogen or $C_{1-3}$ alkyl. $X^1$ and $X^2$ are independently O, $S(O)_m$ or $NR^5$. Y is O or $NR^7$; with the proviso that when the bond between C2 and C3 is a single bond, Y is O. In each occurrence m is independently zero to two. In each occurrence n is zero to three. In each occurrence, p is zero to second; or a pharmaceutically acceptable salt thereof.

In a second embodiment of the invention there is provided a compound according to formula I wherein Y is O; and, $R^1$, $R^{2a}$, $R^{2b}$, $R^{2c}$, $R^3$, $R^4$, $R^5$, $R^7$, $R^a$, $R^b$, $R^c$, $R^d$, $R^e$, $R^f$, $R^g$, $R^h$, $R^i$, $R^j$, X, $X^1$, $X^2$, m, n and p are as defined herein above.

In another embodiment of the invention there is provided a compound according to formula I wherein Y is O; $R^e$ and $R^f$ either are (i) independently hydrogen, $C_{1-6}$ alkyl, $C_{1-3}$alkoxy-$C_{1-3}$ alkyl $C_{3-7}$ cycloalkyl, phenyl; said cycloalkyl ring optionally substituted with one to four substituents independently selected from the group consisting of $C_{1-3}$ hydroxyalkyl; and said phenyl optionally substituted with hydroxy; or are taken together and (ii) $R^e$ and $R^f$ along with the nitrogen atom to which they are attached form a pyrrolidine, piperidine, azepine, morpholinyl substituted by one or two groups independently selected in each occurrence from halogen, hydroxy, $C_{1-3}$ alkyl, $C_{1-3}$ hydroxyalkyl, $(CH_2)_mNR^gR^h$, —$(CH_2)_mCONR^gR^h$, or —$(CH_2)_mCOR$, or (iii) $R^e$ and $R^f$ together are $(CH_2)_2X^1(CH_2)_2$ optionally substituted with $C_{1-3}$ hydroxyalkyl or $C^{1-3}$ alkyl.

In yet another embodiment of the invention there is provided a compound according to formula I wherein Y is $NR^7$; The bond between C2 and C3 is a double bond, $R^e$ and $R^f$ either are (i) independently hydrogen, $C_{1-6}$ alkyl, $C_{1-3}$alkoxy-$C_{1-3}$ alkyl $C_{3-7}$ cycloalkyl, phenyl; said cycloalkyl ring optionally substituted with one to four substituents independently selected from the group consisting of $C_{1-3}$ hydroxyalkyl; and said phenyl optionally substituted with hydroxy; or are taken together and (ii) $R^e$ and $R^f$ along with the nitrogen atom to which they are attached form a pyrrolidine, piperidine, azepine, morpholinyl substituted by one or two groups independently selected in each occurrence from halogen, hydroxy, $C_{1-3}$ alkyl, $C_{1-3}$ hydroxyalkyl, $(CH_2)_mNR^gR^h$, —$(CH_2)_mCONR^gR^h$, or —$(CH_2)_mCOR$, or (iii) $R^e$ and $R^f$ together are $(CH_2)_2X^1(CH_2)_2$ optionally substituted with $C_{1-3}$ hydroxyalkyl or $C^{1-3}$ alkyl.

In a third embodiment of the present invention there is provided a compound according to formula I wherein Y is O and Z is CH. The bond between C2 and C3 is a double bond. $R^1$ is —$(CR^7_2)_mCOX$ wherein m is zero and X is $NR^eR^f$. $R^e$ and $R^f$ together with the nitrogen to which they are attached are piperidine, pyrrolidine or morpholine each optionally substituted by $(CR^7_2)_mNR^gR^h$ wherein m and p are zero or one and $R^7$ is, in each occurrence, hydrogen; $R^g$ is hydrogen or $C_{1-3}$ alkyl; and, $R^h$ is hydrogen, $C_{1-3}$ alkyl, $C_{1-3}$ alkylsulfonyl, cyclopropylsulfonyl or $SO_2NR^iR^j$ wherein $R^i$ and $R^j$ are independently hydrogen, $C_{1-3}$ alkyl.

In a another embodiment of the present invention there is provided a compound according to formula I wherein Y is O and Z is N. The bond between C2 and C3 is a double bond. $R^1$ is —$(CR^7_2)_mCOX$ wherein m is zero and X is $NR^eR^f$. $R^e$ and $R^f$ together with the nitrogen to which they are attached are piperidine, pyrrolidine or morpholine each optionally substituted by $(CR^7_2)_mNR^gR^h$ wherein m and p are zero or one and $R^7$ is, in each occurrence, hydrogen; $R^g$ is hydrogen or $C_{1-3}$ alkyl; and, $R^h$ is hydrogen, $C_{1-3}$ alkyl, $C_{1-3}$ alkylsulfonyl, cyclopropylsulfonyl or $SO_2NR^iR^j$ wherein $R^i$ and $R^j$ are independently hydrogen, $C_{1-3}$ alkyl.

In a third embodiment of the present invention there is provided a compound according to formula I wherein Y is S and Z is CH. The bond between C2 and C3 is a double bond. $R^1$ is —$(CR^7_2)_mCOX$ wherein m is zero and X is $NR^eR^f$. $R^e$ and $R^f$ together with the nitrogen to which they are attached are piperidine, pyrrolidine or morpholine each optionally substituted by $(CR^7_2)_mNR^gR^h$ wherein m and p are zero or one and $R^7$ is, in each occurrence, hydrogen; $R^g$ is hydrogen or $C_{1-3}$ alkyl; and, $R^h$ is hydrogen, $C_{1-3}$ alkyl, $C_{1-3}$ alkylsulfonyl, cyclopropylsulfonyl or $SO_2NR^iR^j$ wherein $R^i$ and $R^j$ are independently hydrogen, $C_{1-3}$ alkyl.

In a fourth embodiment of the present invention there is provided a compound according to formula I wherein Y is O and Z is CH. The bond between C2 and C3 is a double bond. $R^1$ is —$(CR^7_2)_mCOX$ wherein m is zero. $R^{2a}$, $R^{2b}$ and $R^{2c}$ are methyl. $R^3$ is halogen or $C_{1-3}$ alkyl. X is $NR^eR^f$ wherein $R^e$ and $R^f$ together with the nitrogen to which they are attached are piperidine, pyrrolidine or morpholine each optionally substituted by $(CR^7_2)_mNR^gR^h$ wherein m is zero or one, $R^7$ is, in each occurrence, hydrogen and p is one. $R^g$ is hydrogen or $C_{1-3}$ alkyl; and, $R^h$ is hydrogen, $C_{1-3}$ alkyl, $C_{1-3}$ alkylsulfonyl, cyclopropylsulfonyl or $SO_2NR^iR^j$ wherein $R^i$ and $R^j$ are independently hydrogen or $C_{1-3}$ alkyl.

In another embodiment of the present invention there is provided a compound according to formula I wherein Y is O and Z is CH. the bond between C2 and C3 is a double bond;

$R^1$ is —$(CR^7_2)_m$COX wherein m is zero. $R^{2a}$, $R^{2b}$ and $R^{2c}$ are methyl. X is $NR^eR^f$; $R^e$ and $R^f$ together with the nitrogen to which they are attached are piperidine, pyrrolidine or morpholine each optionally substituted by $(CR^7_2)_m NR^g R^h$ wherein m is zero or one, $R^7$ is, in each occurrence, hydrogen and p is zero. $R^g$ is hydrogen or $C_{1-3}$ alkyl and $R^h$ is hydrogen, $C_{1-3}$ alkyl, $C_{1-3}$ alkylsulfonyl, cyclopropylsulfonyl or $SO_2 NR^i R^j$ wherein $R^i$ and $R^j$ are independently hydrogen or $C_{1-3}$ alkyl.

In a fifth embodiment of the present invention there is provided a compound according to formula I wherein Y is O and Z is CH. The bond between C2 and C3 is a double bond. $R^1$ is —$(CR^7_2)_m$COX wherein m is zero, $R^7$ is, in each occurrence, hydrogen and X is $NR^eR^f$. $R^e$ and $R^f$ together with the nitrogen to which they are attached are piperidine, pyrrolidine ring or morpholine each optionally substituted by $(CR^7_2)_m NR^g R^h$ wherein m and p are zero or one. $R^g$ is hydrogen and $R^h$ is $C_{1-3}$ alkylsulfonyl or cyclopropylsulfonyl.

In another embodiment of the present invention there is provided a compound according to formula I wherein Y is O and Z is CH. The bond between C2 and C3 is a double bond. $R^1$ is —$(CR^7_2)_m$COX wherein m is zero, $R^7$ is, in each occurrence, hydrogen and X is $NR^eR^f$. $R^{2a}$, $R^{2b}$ and $R^{2c}$ are methyl. $R^e$ and $R^f$ together with the nitrogen to which they are attached are piperidine, pyrrolidine ring or morpholine each optionally substituted by $(CR^7_2)_m NR^g R^h$ wherein m and p are zero or one. $R^g$ is hydrogen and, $R^h$ is $C_{1-3}$ alkylsulfonyl or cyclopropylsulfonyl.

In another embodiment of the present invention there is provided a compound according to formula I wherein Y is O and Z is CH. The bond between C2 and C3 is a double bond. $R^1$ is —$(CR^7_2)_m$COX wherein m is zero, $R^7$ is, in each occurrence, hydrogen and X is $NR^eR^f$. $R^{2a}$, $R^{2b}$ and $R^{2c}$ are methyl. $R^e$ and $R^f$ together with the nitrogen to which they are attached are piperidine, pyrrolidine substituted at the C3 by $(CH_2)_m NR^g R^h$ or morpholine substituted at C2 by $(CH_2)_m NR^g R^h$ wherein m and p are zero or one. $R^g$ is hydrogen and $R^h$ is $C_{1-3}$ alkylsulfonyl or cyclopropylsulfonyl.

In a sixth embodiment of the present invention there is provided a compound according to formula I wherein Y is O and Z is CH. The bond between C2 and C3 is a double bond. $R^1$ is phenyl or pyridinyl optionally independently substituted with one to three substituent selected from the group consisting of hydroxy, $C_{1-6}$ alkoxy, hydroxy, $C_{1-6}$ alkyl, $C_{1-6}$ haloalkyl, $C_{1-6}$ heteroalkyl, $C_{1-3}$ alkoxy-$C_{1-6}$ alkyl, —$(CR^7_2)_m NR^a R^b$, cyano, nitro, —$(CR^7_2)_m COR^4$, —$(CR^7_2)_m SO_2 NR^c R^d$ and —$O(CR^7_2)_m COR^4$ wherein m is zero or one and $R^7$ is, in each occurrence, hydrogen.

In another embodiment of the present invention there is provided a compound according to formula I wherein Y is O and Z is CH. The bond between C2 and C3 is a double bond. $R^1$ is phenyl or pyridinyl optionally independently substituted with one to three substituent selected from the group consisting of hydroxy, $C_{1-6}$ alkoxy, hydroxy, $C_{1-6}$ alkyl, $C_{1-6}$ haloalkyl, $C_{1-6}$ heteroalkyl, $C_{1-3}$ alkoxy-$C_{1-6}$ alkyl, —$(CR^7_2)_m NR^a R^b$, cyano, nitro, —$(CR^7_2)_m COR^4$, —$(CR^7_2)_m SO_2 NR^c R^d$ and —$O(CR^7_2)_m COR^4$ wherein m is zero or one and $R^7$ is, in each occurrence, hydrogen. $R^{2a}$, $R^{2b}$ and $R^{2c}$ are methyl.

In a seventh embodiment of the present invention there is provided a compound according to formula I wherein Y is O and Z is CH. The bond between C2 and C3 is a double bond. $R^1$ is phenyl or pyridinyl substituted by either (a) —$(CR^7_2)_m NR^a R^b$ wherein wherein m is zero or one, $R^7$ is, in each occurrence, hydrogen, $R^a$ is hydrogen, $C_{1-3}$ alkyl or $C_{1-3}$ hydroxyalkyl and $R^b$ is hydrogen, $C_{1-3}$ alkyl, $C_{1-3}$ alkylsulfonyl or cyclopropylsulfonyl; or, (b) —$(CR^7_2)_m COR^4$ wherein m is zero or one, $R^7$ is, in each occurrence, hydrogen and $R^4$ is $NR^c R^d$.

In another embodiment of the present invention there is provided a compound according to formula I wherein Y is O and Z is CH. The bond between C2 and C3 is a double bond and $R^1$ is phenyl or pyridinyl substituted at the 4-position by (a) —$(CR^7_2)_m NR^a R^b$ wherein m is zero or one, $R^7$ is, in each occurrence, hydrogen, $R^a$ is hydrogen, $C_{1-3}$ alkyl or $C_{1-3}$ hydroxyalkyl and $R^b$ is hydrogen, $C_{1-3}$ alkyl, $C_{1-3}$ alkylsulfonyl or cyclopropylsulfonyl; or, (b) —$(CR^7_2)_m COR^4$ and $R^4$ is $NR^c R^d$ wherein m is zero or one and $R^7$ is, in each occurrence, hydrogen.

In a eighth embodiment of the present invention there is provided a compound according to formula I wherein Y is O and Z is CH. The bond between C2 and C3 is a double bond. $R^1$ is phenyl or pyridinyl substituted by a one to three substituents independently selected from the group consisting of hydroxy, $C_{1-6}$ alkoxy, cyano and —$O(CR^7_2)_m COR^4$ wherein m is zero or one and $R^7$ is, in each occurrence, hydrogen.

In another embodiment of the present invention there is provided a compound according to formula I wherein Y is O and Z is CH. The bond between C2 and C3 is a double bond and $R^1$ is phenyl or pyridinyl either substituted by a one to three substituents independently selected from the group consisting of hydroxy, $C_{1-6}$ alkoxy, cyano and —$O(CR^7_2)_m COR^4$ wherein m is zero or one and $R^7$ is, in each occurrence, hydrogen. $R^{2a}$, $R^{2b}$ and $R^{2c}$ are methyl.

In a ninth embodiment of the invention there is provided a compound according to formula I wherein Y is $NR^7$ and Z is CH. $R^7$ is $C_{1-3}$ alkyl and $R^1$, $R^{2a}$, $R^{2b}$, $R^{2c}$, $R^3$, $R^4$, $R^5$, $R^7$, $R^a$, $R^h$, $R^e$, $R^d$, $R^e$, $R^f$, $R^g$, $R^h$, $R^i$, $R^j$, X, $X^1$, $X^2$, m, n and p are as defined herein above.

In a tenth embodiment of the present invention there is provided a compound according to formula I wherein Y is $NR^7$ and Z is CH wherein $R^7$ is $C_{1-3}$ alkyl. The bond between C2 and C3 is a double bond; $R^1$ is —$(CR^7_2)_m$COX wherein m is zero and $R^7$ is, in each occurrence, hydrogen and X is $NR^eR^f$. $R^e$ and $R^f$ together with the nitrogen to which they are attached are piperidine, pyrrolidine or morpholine each optionally substituted by $(CR^7_2)_m NR^g R^h$ wherein m is zero or one and $R^7$ is, in each occurrence, hydrogen. p is zero or one. $R^g$ is hydrogen or $C_{1-3}$ alkyl and, $R^h$ is hydrogen, $C_{1-3}$ alkyl, $C_{1-3}$ alkylsulfonyl, cyclopropylsulfonyl or $SO_2 NR^i R^j$ wherein $R^i$ and $R^j$ are independently hydrogen or $C_{1-3}$ alkyl.

In another embodiment of the present invention there is provided a compound according to formula I wherein Y is $NR^7$ and Z is CH wherein $R^7$ is $C_{1-3}$ alkyl. The bond between C2 and C3 is a double bond. $R^1$ is —$(CR^7_2)_m$COX wherein m is zero, $R^7$ is, in each occurrence, hydrogen and X is $NR^eR^f$. $R^e$ and $R^f$ together with the nitrogen to which they are attached are piperidine, pyrrolidine or morpholine each optionally substituted by $(CR^7_2)_m NR^g R^h$ wherein m is zero or one and $R^7$ is, in each occurrence, hydrogen. p is zero or one. $R^g$ is hydrogen or $C_{1-3}$ alkyl and, $R^h$ is hydrogen, $C_{1-3}$ alkyl, $C_{1-3}$ alkylsulfonyl, cyclopropylsulfonyl or $SO_2 NR^i R^j$ wherein $R^i$ and $R^j$ are independently hydrogen or $C_{1-3}$ alkyl. $R^3$ is halogen or $C_{1-3}$ alkyl. $R^{2a}$, $R^{2b}$ and $R^{2c}$ are methyl.

In another embodiment of the present invention there is provided a compound according to formula I wherein Y is $NR^7$ and Z is CH wherein $R^7$ is $C_{1-3}$ alkyl. The bond between C2 and C3 is a double bond. $R^1$ is —$(CR^7_2)_m$COX wherein m is zero, $R^7$ is, in each occurrence, hydrogen and X is $NR^eR^f$. $R^e$ and $R^f$ together with the nitrogen to which they are attached are piperidine, pyrrolidine or morpholine each optionally substituted by $(CR^7_2)_m NR^g R^h$ wherein m is zero or one and $R^7$ is, in each occurrence, hydrogen. p is zero. $R^g$ is hydrogen or $C_{1-3}$ alkyl and $R^h$ is hydrogen, $C_{1-3}$ alkyl, $C_{1-3}$ alkylsulfonyl, cyclopropylsulfonyl or $SO_2NR^iR^j$ wherein $R^i$ and $R^j$ are independently hydrogen or $C_{1-3}$ alkyl. $R^{2a}$, $R^{2h}$ and $R^{2e}$ are methyl.

In an eleventh embodiment of the present invention there is provide a compound according to formula I which compound is selected from compounds I-1 to I-111 and I-112 in TABLE I.

In a twelfth embodiment of the present invention there is provide a method of treating a disease caused by HCV in a patient in need thereof comprising administering a therapeutically effective amount of a compound according to formula I wherein $R^1$, $R^{2a}$, $R^{2b}$, $R^{2c}$, $R^3$, $R^4$, $R^5$, $R^7$, $R^a$, $R^b$, $R^c$, $R^d$, $R^e$, $R^f$, $R^g$, $R^h$, $R^i$, $R^j$, X, $X^1$, $X^2$, Y, Z, m, n and p are as defined herein above.

In a thirteenth embodiment of the present invention there is provide a method of treating a disease caused by HCV in a patient in need thereof comprising co-administering a therapeutically effective amount of a compound according to formula I wherein $R^1$, $R^{2a}$, $R^{2b}$, $R^{2c}$, $R^3$, $R^4$, $R^5$, $R^7$, $R^a$, $R^b$, $R^c$, $R^d$, $R^e$, $R^f$, $R^g$, $R^h$, $R^i$, $R^j$, X, $X^1$, $X^2$, Y, Z, m, n and p are as defined herein above and at least one immune system modulator and/or at least one antiviral agent that inhibits replication of HCV.

In a fourteenth embodiment of the present invention there is provide a method of treating a disease caused by HCV in a patient in need thereof comprising co-administering a therapeutically effective amount of a compound according to formula I wherein $R^1$, $R^{2a}$, $R^{2b}$, $R^{2c}$, $R^3$, $R^4$, $R^5$, $R^7$, $R^a$, $R^b$, $R^c$, $R^d$, $R^e$, $R^f$, $R^g$, $R^h$, $R^i$, $R^j$, X, $X^1$, $X^2$, Y, Z, m, n and p are as defined herein above and at least one immune system modulator and/or at least one antiviral agent that inhibits replication of HCV.

In a fifteenth embodiment of the present invention there is provide a method of treating a disease caused by HCV in a patient in need thereof comprising co-administering a therapeutically effective amount of a compound according to formula I wherein $R^1$, $R^{2a}$, $R^{2b}$, $R^{2c}$, $R^3$, $R^4$, $R^5$, $R^7$, $R^a$, $R^b$, $R^c$, $R^d$, $R^e$, $R^f$, $R^g$, $R^h$, $R^i$, $R^j$, X, $X^1$, $X^2$, Y, Z, m, n and p are as defined herein above and an interferon or chemically derivatized interferon.

In a sixteenth embodiment of the present invention there is provide a method of treating a disease caused by HCV in a patient in need thereof comprising co-administering a therapeutically effective amount of a compound according to formula I wherein $R^1$, $R^{2a}$, $R^{2b}$, $R^{2c}$, $R^3$, $R^4$, $R^5$, $R^7$, $R^a$, $R^b$, $R^c$, $R^d$, $R^e$, $R^f$, $R^g$, $R^h$, $R^i$, $R^j$, X, $X^1$, $X^2$, Y, Z, m, n and p are as defined herein above and another antiviral compound selected from the group consisting of a HCV protease inhibitor, another HCV polymerase inhibitor, a HCV helicase inhibitor, a HCV primase inhibitor and a HCV fusion inhibitor.

In a seventeenth embodiment of the present invention there is provided a method of inhibiting the replication of HCV in a cell comprising administering a therapeutically effective amount of a compound according to formula I wherein $R^1$, $R^{2a}$, $R^{2b}$, $R^{2e}$, $R^3$, $R^4$, $R^5$, $R^7$, $R^a$, $R^b$, $R^c$, $R^d$, $R^e$, $R^f$, $R^g$, $R^h$, $R^i$, $R^j$, X, $X^1$, $X^2$, Y, Z, m, n and p are as defined herein above.

In a eighteenth embodiment of the present invention there is provided a composition containing a therapeutically effective amount of a compound according to formula I wherein $R^1$, $R^{2a}$, $R^{2b}$, $R^{2c}$, $R^3$, $R^4$, $R^5$, $R^7$, $R^a$, $R^b$, $R^c$, $R^d$, $R^e$, $R^f$, $R^g$, $R^h$, $R^i$, $R^j$, X, $X^1$, $X^2$, Y, Z, m, n and p are as defined herein above admixed with at least one pharmaceutically acceptable carrier, diluent or excipient.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "alkyl" as used herein without further limitation denotes an unbranched or branched chain, satd., monovalent hydrocarbon residue containing 1 to 10 carbon atoms. The term "lower alkyl" denotes a straight or branched chain hydrocarbon residue containing 1 to 6 carbon atoms. "$C_{1-6}$ alkyl" as used herein refers to an alkyl composed of 1 to 6 carbons. Examples of alkyl groups include, but are not limited to, lower alkyl groups include methyl, ethyl, propyl, i-propyl, n-butyl, i-butyl, t-butyl, neopentyl, hexyl, and octyl.

The term "haloalkyl" as used herein denotes a unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, 1-fluoroethyl, 1-chloroethyl, 12-fluoroethyl, 2-chloroethyl, 2-bromoethyl, 2,2-dichloroethyl, 3-bromopropyl or 2,2,2-trifluoroethyl.

The term "$C_{1-6}$ fluoroalkyl" as used herein denotes a unbranched or branched chain alkyl group as defined above wherein 1, 2, 3 or more hydrogen atoms are substituted by a fluorine.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The terms "hydroxyalkyl" and "alkoxyalkyl" as used herein denote an alkyl radical as herein defined wherein one to three hydrogen atoms on different carbon atoms is/are replaced by hydroxyl or alkoxy groups respectively. A $C_{1-3}$ alkoxy-$C_{1-6}$ alkyl moiety refers to a $C_{1-6}$ alkyl substituent in which 1 to 3 hydrogen atoms are replaced by a C1-3 alkoxy and the point of attachment of the alkoxy is the oxygen atom.

The term "halogen" or "halo" as used herein means fluorine, chlorine, bromine, or iodine.

The term "acyl" or "alkanoyl" as used herein denotes a group of formula —C(═O)R wherein R is hydrogen or lower alkyl as defined herein. The term or "alkylcarbonyl" as used herein denotes a group of formula C(═O)R wherein R is alkyl as defined herein. The term $C_{1-6}$ acyl refers to a group —C(═O)R contain 1 to 6 carbon atoms. The $C_1$ acyl group is the formyl group wherein R═H and a $C_6$ acyl group refers to hexanoyl when the alkyl chain is unbranched. The term "arylcarbonyl" as used herein means a group of formula C(═O)R wherein R is an aryl group; the term "benzoyl" as used herein an "arylcarbonyl" group wherein R is phenyl.

The terms "amino", "alkylamino" and "dialkylamino" as used herein refer to —NH$_2$, —NHR and —NR$_2$ respectively and R is alkyl as defined above. The two alkyl groups attached to a nitrogen in a dialkyl moiety can be the same or different. The terms "aminoalkyl", "alkylaminoalkyl" and "dialkylaminoalkyl" as used herein refer to NH$_2$(alkylene)-[or NH$_2$(CR'$_2$)$_n$—], RHN(alkylene)-[or NHR(CR'$_2$)$_n$—], and R$_2$N(alkylene)-[or NR$_2$(CR'$_2$)$_n$—] respectively wherein R is alkyl, and both alkylene and alkyl are as defined herein. "C$_{1-10}$ alkylamino" as used herein refers to an aminoalkyl wherein alkyl is C$_{1-10}$. C$_{1-10}$ alkyl-amino-C$_{2-6}$ alkyl" as used herein refers to a C$_{1-10}$ alkylamino(alkylene)$_{2-6}$ wherein alkyl is C$_{1-10}$ and the alkylene is (CH$_2$)$_{2-6}$. When the alkylene group contains three or more carbon atoms, the alkylene can be linear, e.g. —(CH$_2$)$_4$— or branched, e.g., —(CMe$_2$CH$_2$)—. The term "phenylamino" as used herein refers to —NHPh wherein Ph represents an optionally substituted phenyl group.

The term "alkylene" as used herein denotes a divalent saturated linear hydrocarbon radical of 1 to 10 carbon atoms (e.g., (CH$_2$)$_n$) or a branched saturated divalent hydrocarbon radical of 2 to 10 carbon atoms (e.g., —CHMe— or —CH$_2$CH(i-Pr)CH$_2$—), unless otherwise indicated. C$_{0-4}$ alkylene refers to a linear or branched saturated divalent hydrocarbon radical comprising 1-4 carbon atoms or, in the case of C$_0$, the alkylene radical is omitted. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The terms "alkylsulfonyl" and "arylsulfonyl" as used herein denotes a group of formula —S(=O)$_2$R wherein R is alkyl or aryl respectively and alkyl and aryl are as defined herein. The term "C$_{1-3}$ alkylsulfonylamido" or "C$_{1-3}$ alkylsulfonylamino" as used herein refers to a group RSO$_2$NH— wherein R is a C$_{1-3}$ alkyl group as defined herein. The terms C$_{1-6}$ haloalkylsulfonyl, C$_{3-7}$ cycloalkylsulfonyl, refer to a compound, S(=O)$_2$R wherein R is C$_{1-6}$ haloalkyl or C$_{3-7}$ cycloalkyl, respectively The terms "oxetane" (oxetanyl), "tetrahydrofuran" (tetrahydrofuranyl) and "tetrahydropyran" ("tetrahydropyranyl") refer to a four, five and six-membered non-fused heterocyclic ring respectively, each containing one oxygen atom. "azetidine" ("azetidinyl") "pyrrole" ("pyrrolidinyl"), "piperidine" ("piperidinyl"), "azepine" ("azepinyl") The terms "furan" ("furyl"), "pyrrole" ("pyrrolyl") and "thiophene" ("thienyl") refer to five membered heteroaryl rings with one oxygen, nitrogen and sulfur respectively. The term "pyridine" ("pyridinyl") refers to a six-membered heteroaromatic ring with one nitrogen atom. The terms "pyrimidine" (pyrimidinyl), "pyrazine" ("pyrazinyl") and "pyridazine" ("pyridazinyl") refer to a six-membered nonfused heteroaromatic ring with two nitrogen atoms disposed in a 1,3, a 1,4 and a 1,2 relationship respectively. The respective radical names are in parentheses.

The terms thiazol-2-yl, pyrazolidin-1-yl, thiazolidin-3-yl, isothiazolidin-2-yl, isoxazolidin-2-yl or oxazolidin-3-yl refer to radicals (i) to (vi) respectively

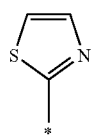

(i)

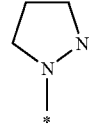

(ii)

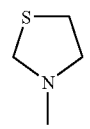

(iii)

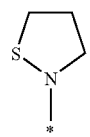

(iv)

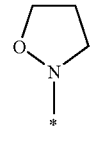

(v)

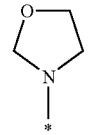

(vi)

Compounds of the present invention and their isomeric forms and pharmaceutically acceptable salts thereof are also useful in treating viral infections, in particular, hepatitis C infection, and diseases in living hosts when used in combination with each other and with other biologically active agents, including but not limited to the group consisting of interferon, a pegylated interferon, ribavirin, protease inhibitors, polymerase inhibitors, small interfering RNA compounds, antisense compounds, nucleotide analogs, nucleoside analogs, immunoglobulins, immunomodulators, hepatoprotectants, anti-inflammatory agents, antibiotics, antivirals and antiinfective compounds. Such combination therapy may also comprise providing a compound of the invention either concurrently or sequentially with other medicinal agents or potentiators, such as ribavirin and related compounds, amantadine and related compounds, various interferons such as, for example, interferon-alpha, interferon-beta, interferon gamma and the like, as well as alternate forms of interferons such as pegylated interferons. Additionally combinations of ribavirin and interferon, may be administered as an additional combination therapy with at least one of the compounds of the present invention.

In one embodiment, the compounds of the present invention according to formula I are used in combination with other active therapeutic ingredients or agents to treat patients with an HCV viral infection. According to the present invention, the active therapeutic ingredient used in combination with the compound of the present invention can be any agent having a therapeutic effect when used in combination with the compound of the present invention. For example, the active agent used in combination with the compound of the present invention can be interferons, ribavirin analogs, HCV NS3 protease inhibitors, nucleoside inhibitors of HCV polymerase, non-nucleoside inhibitors of HCV polymerase, and other drugs for treating HCV, or mixtures thereof.

Examples of the nucleoside NS5b polymerase inhibitors include, but are not limited to NM-283, valopicitabine, R1626, PSI-6130 (R1656), IDX184 and IDX102 (Idenix) BILB 1941.

Examples of the non-nucleoside NS5b polymerase inhibitors include, but are not limited to HCV-796 (ViroPharma and Wyeth), MK-0608, MK-3281 (Merck), NM-107, R7128 (R4048), VCH-759, GSK625433 and GSK625433 (Glaxo), PF-868554 (Pfizer), GS-9190 (Gilead), A-837093 and A848837 (Abbot Laboratories), ANA598 (Anadys Pharmaceuticals); GL100597 (GNLB/NVS), VBY 708 (ViroBay), benzimidazole derivatives (H. Hashimoto et al. WO 01/47833, H. Hashimoto et al. WO 03/000254, P. L. Beaulieu et al. WO 03/020240 A2; P. L. Beaulieu et al. U.S. Pat. No. 6,448,281 B1; P. L. Beaulieu et al. WO 03/007945 A1), benzo-1,2,4-thiadiazine derivatives (D. Dhanak et al. WO 01/85172 A1, filed May 10, 2001; D. Chai et al., WO2002098424, filed Jun. 7, 2002, D. Dhanak et al. WO 03/037262 A2, filed Oct. 28, 2002; K. J. Duffy et al. WO03/099801 A1, filed May 23, 2003, M. G. Darcy et al. WO2003059356, filed Oct. 28, 2002; D. Chai et al. WO 2004052312, filed Jun. 24, 2004, D. Chai et al. WO2004052313, filed Dec. 13, 2003; D. M. Fitch et al., WO2004058150, filed Dec. 11, 2003; D. K. Hutchinson et al. WO2005019191, filed Aug. 19, 2004; J. K. Pratt et al. WO 2004/041818 A1, filed Oct. 31, 2003), 1,1-dioxo-4H-benzo[1,4]thiazin-3-yl derivatives (J. F. Blake et al. in U.S. Patent Publication US20060252785 and 1,1-dioxo-benzo[d]isothazol-3-yl compounds (J. F. Blake et al. in U.S. Patent Publication 2006040927).

Examples of the HCV NS3 protease inhibitors include, but are not limited to SCH-503034 (Schering, SCH-7), VX-950 (telaprevir, Vertex), BILN-2065 (Boehringer-Ingelheim, BMS-605339 (Bristo Myers Squibb), and ITMN-191 (Intermune).

Examples of the interferons include, but are not limited to pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen and actimmune, IFN-omega with DUROS, albuferon, locteron, Albuferon, Rebif, oral interferon alpha, IFNalpha-2b XL, AVI-005, PEG-Infergen, and pegylated IFN-beta.

Ribavirin analogs and the ribavirin prodrug viramidine (taribavirin) have been administered with interferons to control HCV.

Commonly used abbreviations include: acetyl (Ac), aqueous (aq.), atmospheres (Atm), 2,2'-bis(diphenylphosphino)-1,1'-binaphthyl (BINAP), tert-butoxycarbonyl (Boc), di-tert-butyl pyrocarbonate or boc anhydride (BOC$_2$O), benzyl (Bn), butyl (Bu), Chemical Abstracts Registration Number (CASRN), benzyloxycarbonyl (CBZ or Z), carbonyl diimidazo (CDI), 1,5-diazabicyclo[4.3.0]non-5-ene (DBN), 1,8-diazabicyclo[5.4.0]undec-7-ene (DBU), N,N'-dicyclohexyl-carbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino) ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether (Et$_2$O), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), methanol (MeOH), melting point (mp), MeSO$_2$— (mesyl or Ms), methyl (Me), acetonitrile (MeCN), m-chloroperbenzoic acid (MCPBA), mass spectrum (ms), methyl tert-butyl ether (MTBE), N-methylmorpholine (NMM), N-methylpyrrolidone (NMP), phenyl (Ph), propyl (Pr), iso-propyl (i-Pr), pounds per square inch (psi), pyridine (pyr), room temperature (rt or RT), satd. (saturated), tert-butyldimethylsilyl or t-BuMe2Si (TBDMS), triethylamine (TEA or Et$_3$N), triflate or CF$_3$SO$_2$— (TO, trifluoroacetic acid (TFA), O-benzotriazol-1-yl-N,N,N',N'-tetramethyluronium tetrafluoroborate (TBTU), thin layer chromatography (TLC), tetrahydrofuran (THF), tetramethylethylenediamine (TMEDA), trimethylsilyl or Me$_3$Si (TMS), p-toluenesulfonic acid monohydrate (TsOH or pTsOH), 4-Me—C$_6$H$_4$SO$_2$— or tosyl (Ts), N-urethane-N-carboxyanhydride (UNCA). Conventional nomenclature including the prefixes normal (n), iso (i-), secondary (sec-), tertiary (tert- or t-) and neo- have their customary meaning when used with an alkyl moiety. (J. Rigaudy and D. P. Klesney, Nomenclature in Organic Chemistry, IUPAC 1979 Pergamon Press, Oxford.).

Compounds and Preparation

In general, the nomenclature used in this application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

Compounds of the present invention can be made by a variety of methods illustrated in the synthetic reaction schemes depicted and described below. The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, Volumes 1-21; R. C. LaRock, Comprehensive Organic Transformations, 2nd edition Wiley-VCH, New York 1999; Comprehensive Organic Synthesis, B. Trost and I. Fleming (Eds.) vol. 1-9 Pergamon, Oxford, 1991; Comprehensive Heterocyclic Chemistry, A. R. Katritzky and C. W. Rees (Eds) Pergamon, Oxford 1984, vol. 1-9; Comprehensive Heterocyclic Chemistry II, A. R. Katritzky and C. W. Rees (Eds) Pergamon, Oxford 1996, vol. 1-11; and Organic Reactions, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C. The optimal temperature will vary according to the nature of the reaction and electronic and steric effects which may accelerate or attenuate the reaction rate.

In general, the nomenclature used in this application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

Examples of representative compounds within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

TABLE I[3]

| Cpd No. | $R^1$ | $R^2$ | $R^3$ | Y | ms | mp | $IC_{50}$[1] |
|---|---|---|---|---|---|---|---|
| I-1 | —OH | t-Bu | H | O | 284 | | |
| I-2 | —H | t-Bu | H | O | 268 | 217.0-218.0 | 0.202 |
| I-3 | —$CO_2Et$ | t-Bu | H | O | 340 | | 0.258 |
| I-4 | —$CO_2H$ | t-Bu | H | O | 312 | | 0.381 |
| I-5 | —$CH_2CN$ | t-Bu | H | O | 307 | 231.0-232.0 | 0.330 |
| I-6 | —$CH_2CO_2H$ | t-Bu | H | O | 326 | 233.0-234.0 | 0.358 |
| I-7 | morpholinyl carbonyl | t-Bu | H | O | 381 | | 0.142 |
| I-8 | —$CH_2OH$ | t-Bu | H | O | 298 | | 0.515 |
| I-9 | —CONH-i-Pr | t-Bu | H | O | 353 | | 1.54 |
| I-10 | —$CONHCH_2$-i-Pr | t-Bu | H | O | 367 | | 0.404 |
| I-11 | —CON(Me)-$CH_2$-i-Pr | t-Bu | H | O | 381 | | 0.475 |
| I-12 | 4-hydroxypiperidinyl carbonyl | t-Bu | H | O | 395 | | 0.063 |
| I-13 | piperidinyl carbonyl | t-Bu | H | O | 379 | | 0.048 |
| I-14 | 3-(hydroxymethyl)piperidinyl carbonyl | t-Bu | H | O | 409 | | 0.066 |
| I-15 | 2-(hydroxymethyl)morpholinyl carbonyl | t-Bu | H | O | 411 | | 0.325 |

TABLE I³-continued

Structure (I): 2-oxo-1H-pyridine attached to benzofuran/indole with R¹ at position 3, R² at position 7, (R³)n substituents, and Y heteroatom.

| Cpd No. | R¹ | R² | R³ | Y | ms | mp | IC₅₀¹ |
|---|---|---|---|---|---|---|---|
| I-16 | *-C(=O)-N-pyrrolidinyl-CH₂OH (2S) | t-Bu | H | O | 395 | | 0.19 |
| I-17 | *-C(=O)-N-pyrrolidinyl-CH₂OH (2R) | t-Bu | H | O | 395 | | 0.112 |
| I-18 | *-C(=O)NH-C(cyclopentyl)(CH₂OH) | t-Bu | H | O | 409 | | 4.8 |
| I-19 | *—CONH[(CH₂)₂OMe]₂ | t-Bu | H | O | 427 | | 4.35 |
| I-20 | *—C(=O)Ph | t-Bu | H | O | 372 | 271.0-272.0 | 0.049 |
| I-21 | *-C(=O)NH-(3-hydroxyphenyl) | t-Bu | H | O | | 402 | 1.89 |
| I-22 | *—CONHMe | t-Bu | H | O | 325 | | 0.77 |
| I-23 | —CONHPh | t-Bu | H | O | 387 | | 0.425 |
| I-24 | -Ph | t-Bu | H | O | 344 | 257.0-258.0 | 0.019 |
| I-25 | *—CONH(Et)(CH₂)₂OMe | t-Bu | H | O | 397 | | 1.33 |
| I-26 | (2,3-dihydrobenzofuran with 3-CO₂Me, 7-CMe₃) | | | | 328 | | 0.037 |
| I-27 | *-C(=O)-N-piperidinyl-3-OH | t-Bu | H | O | 395 | | 0.186 |

TABLE I³-continued

Structure (I): pyridinone-benzofuran core with substituents R¹ (position 3), R² (position 7), $(R^3)_n$, Y (position 1).

| Cpd No. | R¹ | R² | R³ | Y | ms | mp | IC₅₀¹ |
|---|---|---|---|---|---|---|---|
| I-28 | *-C(O)-piperazine-NH | t-Bu | H | O | 380 | | 1.94 |
| I-29 | *-C(O)-N(piperidine)-NH₂ | t-Bu | H | O | 394 | | 0.024 |
| I-30 | *-C(O)-(3-OMe-phenyl) | t-Bu | H | O | 402 | | 0.329 |
| I-31 | *-C(O)-(3-Me-thiophene-2-yl) | t-Bu | H | O | 392 | | 0.069 |
| I-32 | *-(3-CN-phenyl) | t-Bu | H | O | 369 | | 0.038 |
| I-33 | *-(3-OMe-phenyl) | t-Bu | H | O | 374 | 204.0-205.0 | 0.014 |
| I-34 | *-(3-OH-phenyl) | t-Bu | H | O | 360 | | 0.024 |
| I-35 | *-(4-CN-phenyl) | t-Bu | H | O | 369 | | 0.072 |
| I-36 | *-C(O)-(3-OH-phenyl) | t-Bu | H | O | 388 | 268.0-269.0 | 0.038 |

TABLE I[3]-continued
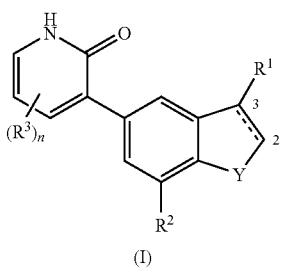
(I)
| Cpd No. | R[1] | R[2] | R[3] | Y | ms | mp | IC$_{50}$[1] |
|---|---|---|---|---|---|---|---|
| I-37 | *—C$_6$H$_4$—CH$_2$NHSO$_2$Me (para) | t-Bu | H | O | 451 | 271.0-273.0 | 0.004 |
| I-38 | (3R)-1-acyl-3-(NHCO$_2$-tert-Bu)piperidine | t-Bu | H | O | 494 | | 0.132 |
| I-39 | 1-acyl-4-(NHCO$_2$-tert-Bu)piperidine | t-Bu | H | O | 494 | | 4.37 |
| I-40 | (3S)-1-acyl-3-(NHCO$_2$-tert-Bu)piperidine | t-Bu | H | O | 516 | | 1.41 |
| I-41 | (3R)-1-acyl-3-aminopiperidine | t-Bu | H | O | 394 | 269.0-270.0 | 0.126 |
| I-42 | (3S)-1-acyl-3-aminopiperidine | t-Bu | H | O | 394 | 254.9-258.1 | 0.549 |
| I-43 | 1-acyl-3-(CH$_2$NHCO$_2$-tert-Bu)piperidine | t-Bu | H | O | 508 | | 1.695 |
| I-45 | 1-acyl-3-(CH$_2$NHCO$_2$-tert-Bu)pyrrolidine | t-Bu | H | O | 494 | | 0.076 |

TABLE I³-continued
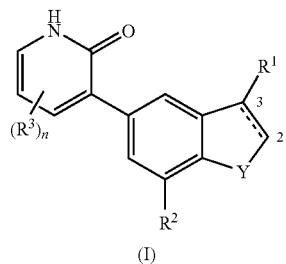
(I)
| Cpd No. | R¹ | R² | R³ | Y | ms | mp | IC$_{50}$¹ |
|---|---|---|---|---|---|---|---|
| I-46 | (1-acyl piperidin-3-yl with NHSO₂Me) | t-Bu | H | O | 472 | | 0.194 |
| I-47 | (1-acyl piperidin-3-yl with NHSO₂Me) | t-Bu | H | O | 472 | | 0.172 |
| I-48 | (1-acyl pyrrolidin-3-yl with NH₂) | t-Bu | H | O | 308 | >300 | 0.052 |
| I-49 | (1-acyl pyrrolidin-3-yl with CH₂NH₂) | t-Bu | H | O | 394 | >300 | 0.104 |
| I-50 | (1-acyl piperidin-3-yl with CH₂NH₂) | t-Bu | H | O | 408 | 150.0-155.0 | 0.051 |
| I-51 | (1-acyl pyrrolidine) | t-Bu | H | O | 365 | | 0.012 |
| I-52 | (1-acyl-4-acetylpiperazine) | t-Bu | H | O | 422 | | 1.246 |
| I-53 | (1-acyl pyrrolidin-3-yl with NMe₂) | t-Bu | H | O | 408 | | 0.454 |
| I-54 | (1-acyl-4-methyl-1,4-diazepane) | t-Bu | H | O | 408 | | 1.54 |

TABLE I³-continued
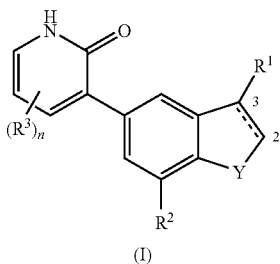
(I)
| Cpd No. | R¹ | R² | R³ | Y | ms | mp | IC₅₀¹ |
|---|---|---|---|---|---|---|---|
| I-55 | *-C(O)-N(piperidine)-NHCOCF₃ | t-Bu | H | O | 490 | | 2.28 |
| I-58 | *-C(O)-N(piperidine)-CONH₂ | t-Bu | H | O | 422 | 422 | 0.282 |
| I-59 | *-C₆H₄-CH₂NH₂ (para) | t-Bu | H | O | 374 | | 0.349 |
| I-60 | *-C(O)-N(pyrrolidine)-NHCOCF₃ | t-Bu | H | O | 476 | | 0.051 |
| I-61 | *-C(O)-N(piperidine)-CONH₂ (3-position) | t-Bu | H | O | 422 | | 0.066 |
| I-62 | *-C₆H₄-CH₂NH₂ (meta) | t-Bu | H | O | 373 | | 0.893 |
| I-63 | *-C(O)-N(pyrrolidine)(MeO₂C)(OH) | t-Bu | H | O | 439 | | 1.61 |
| I-64 | *-C(O)-N(piperidine)(OH)(CONH₂) | t-Bu | H | O | 438 | | 0.097 |
| I-65 | *-C(O)-N(pyrrolidine)-OH | t-Bu | H | O | 381 | | 0.126 |

TABLE I³-continued

| Cpd No. | R¹ | R² | R³ | Y | ms | mp | IC$_{50}$[1] |
|---|---|---|---|---|---|---|---|
| I-66 | [1-(C(O)-)-4-(NHEt)-4-(CONH₂)-piperidine] | t-Bu | H | O | 465 | | 0.134 |
| I-67 | [1-(C(O)-)-3-(NMe₂)-pyrrolidine] | t-Bu | H | O | 408 | | 0.889 |
| I-68 | [1-(C(O)-)-4,4-difluoropiperidine] | t-Bu | H | O | 415 | | 0.597 |
| I-69 | [1-(C(O)-)-3,3-dimethylpiperidine] | t-Bu | H | O | 407 | | 0.831 |
| I-70 | [1-(C(O)-)-3-(CH₂OH)-pyrrolidine] | t-Bu | H | O | 395 | | 0.053 |
| I-71 | [3-(C(O)-)-thiazolidine] | t-Bu | H | O | 383 | | 0.050 |
| I-72 | [1-(C(O)-)-3-(CH₂NHSO₂Me)-pyrrolidine] | t-Bu | H | O | 472 | 258.0-260.0 | 0.008 |
| I-73 | [1-(C(O)-)-3-(CH₂NHSO₂Me)-pyrrolidine] | t-Bu | H | O | 472 | | 0.021 |
| I-74 | [4-(CH₂NHSO₂Me)-phenyl] | t-Bu | 5-F | O | 469 | | 0.037 |

TABLE I³-continued
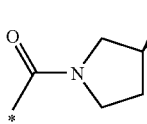
(I)
| Cpd No. | R¹ | R² | R³ | Y | ms | mp | IC$_{50}$¹ |
|---|---|---|---|---|---|---|---|
| I-75 | 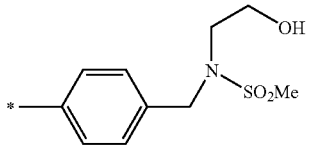 | t-Bu | H | O | 436 | | 0.197 |
| I-76 | 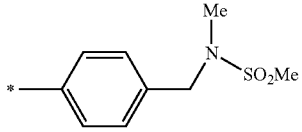 | t-Bu | H | O | 495 | 222.0-224.0 | 0.035 |
| I-77 | 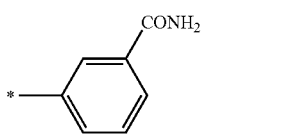 | t-Bu | H | O | 465 | 243.0-245.0 | 0.036 |
| I-78 | 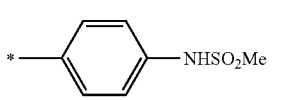 | t-Bu | H | O | 387 | 190.0-193.0 | 0.009 |
| I-79 | 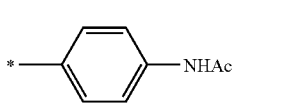 | t-Bu | H | O | 437 | 182.0-184.0 | 0.027 |
| I-80 | 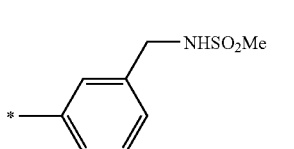 | t-Bu | H | O | 401 | >300 | 0.064 |
| I-81 | 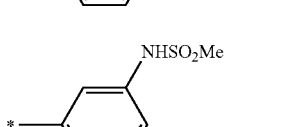 | t-Bu | H | O | | 130.0-133.0 | 0.175 |
| I-82 | 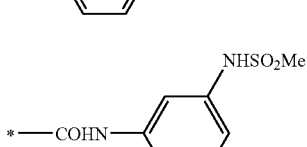 | t-Bu | H | O | | 227.0-230.0 | 0.113 |
| I-83 |  | t-Bu | H | O | | 290.0-291.0 | 0.201 |

TABLE I³-continued

| Cpd No. | R¹ | R² | R³ | Y | ms | mp | IC₅₀¹ |
|---|---|---|---|---|---|---|---|
| I-84 | thiazol-2-yl-NHC(O)-* | t-Bu | H | O | 394 | >300 | 0.357 |
| I-85 | 3-(NHSO₂Me-CH₂)-phenyl-NHC(O)-* | t-Bu | H | O | 494 | 237.0-239.0 | 0.741 |
| I-86 | *-C₆H₄-NH₂ (4-) | t-Bu | H | O |  | 248.0-250.0 | 0.009 |
| I-87 | *-C₆H₄-CONH₂ (4-) | t-Bu | H | O |  | 282.0-284.0 | 0.002 |
| I-88 | *-C₆H₄-CH(Me)NHSO₂Me (4-) | t-Bu | H | O |  | 255.0-257.0 | 0.008 |
| I-89 | *-(2-aminopyrimidin-5-yl) | t-Bu | H | O | 361 | >300 | 0.69 |
| I-90 | 4-(CH₂NHSO₂Me)-piperidin-1-yl-C(O)-* | t-Bu | H | O | 486 |  | 0.006 |
| I-91 | *-(5-methylpyridin-2-yl) | t-Bu | H | O |  | 295.0-297.0 | 0.326 |
| I-92 | (3S)-3-(CH₂NHSO₂Me)-pyrrolidin-1-yl-C(O)-* | t-Bu | 5-F | O |  | 296.0-298.0 | 0.029 |
| I-93 | *-(6-(CH₂NHSO₂Me)pyridin-3-yl) | t-Bu | H | O | 452 |  | 0.012 |

TABLE I[3]-continued

Structure (I): pyridinone-benzofuran core with substituents $R^1$, $R^2$, $(R^3)_n$, and Y.

| Cpd No. | R[1] | R[2] | R[3] | Y | ms | mp | IC$_{50}$[1] |
|---|---|---|---|---|---|---|---|
| I-94 | *-C(O)-N(azetidine) | t-Bu | H | O | 351 | >300 | 0.148 |
| I-95 | *-C(O)-N(azetidin-3-yl-CH$_2$OH) | t-Bu | H | O | 381 | 292.0-293.0 | 0.043 |
| I-96 | *-(6-aminopyridin-3-yl) | t-Bu | H | O |  | 255.0-257.0 | 0.047 |
| I-97 | *-(4-OMe, 3-CH$_2$OMe, 5-CH$_2$NHSO$_2$Me-phenyl) | t-Bu | H | O |  | 128.0-130.0 | 0.515 |
| I-98 | *-C(O)-N(pyrrolidin-3-yl-CH$_2$NHSO$_2$Me) | t-Bu | 6-Me | O |  | 178.0-180.0 | 0.016 |
| I-99 | *-C(O)-N(piperidin-4-yl-NHSO$_2$Me) | t-Bu | H | O |  | 193.0-195.0 | 0.876 |
| I-100[2] | *-C(O)-N(piperidin-3-yl-CH$_2$NHSO$_2$Me) | t-Bu | H | O | 486 |  | 0.008 |
| I-101[2] | *-C(O)-N(piperidin-3-yl-CH$_2$NHSO$_2$Me) | t-Bu | H | O | 486 |  | 0.009 |
| I-102 | *-C(O)-N(azetidin-3-ol) | t-Bu | H | O | 367 | 264.0-266.0 | 0.135 |

TABLE I[3]-continued (Structure I: 1H-pyridin-2-one with (R[3])n substituent, connected to a benzofuran/indole with R[1] at C-3, R[2] at position 7, and Y as the heteroatom)

| Cpd No. | R[1] | R[2] | R[3] | Y | ms | mp | IC$_{50}$[1] |
|---|---|---|---|---|---|---|---|
| I-103 | *-C(O)-azetidinyl-CH$_2$-NHSO$_2$Me | t-Bu | H | O | | 263.0-265.0 | 0.083 |
| I-104 | *-C(O)-piperidinyl-CH$_2$-N(Me)SO$_2$Me | t-Bu | H | O | | 155.0-157.0 | 0.02 |
| I-105 | *-C(O)-pyrrolidinyl-CH$_2$-N(Me)SO$_2$Me | t-Bu | H | O | | 155.0-157.0 | 0.025 |
| I-106 | *-C(O)-pyrrolidinyl-CH$_2$-NHSO$_2$Et | t-Bu | H | O | 486 | 240.0-242.0 | 0.017 |
| I-107 | *-C(O)-pyrrolidinyl-CH$_2$-NHSO$_2$-cyclopropyl | t-Bu | H | O | 498 | 158.0-160.0 | 0.017 |
| I-108 | *-C(O)-pyrrolidinyl-CH$_2$-NHSO$_2$-i-Pr | t-Bu | H | O | 500 | 163.0-165.0 | 0.025 |
| I-109 | *-C(O)-morpholinyl-CH$_2$-NHSO$_2$Me | t-Bu | H | O | 408 | 163.0-165.0 | 0.005 |
| I-110 | —CN | t-Bu | H | NMe | 306 | | 0.314 |
| I-111 | *-C(O)-pyrrolidinyl-CH$_2$-NHSO$_2$Me | t-Bu | H | NMe | 485 | 168.0-170.0 | 0.008 |
| I-112 | —CONH$_2$ | t-Bu | H | NMe | 324 | 232.0-234.0 | 0.778 |

[1]NS5B polymerase assay, see Example 21
[2]The configuration of the C-3 carbon has not been unambiguously assigned.
[3]The C2-C3 bond of all compounds in TABLE 1 is a double bond unless explicitly depicted otherwise.

Some compounds in following schemes are depicted as a Markush structure with generalized substituents; however, one skilled in the art will immediately appreciate that the nature of the R groups as defined in the claims can varied as defined in the appended claims to afford the various compounds contemplated in this invention. Moreover, the reaction conditions are exemplary and alternative conditions can be identified without undue experimentation. The reaction sequences in the following examples are not meant to limit the scope of the invention as set forth in the claims.

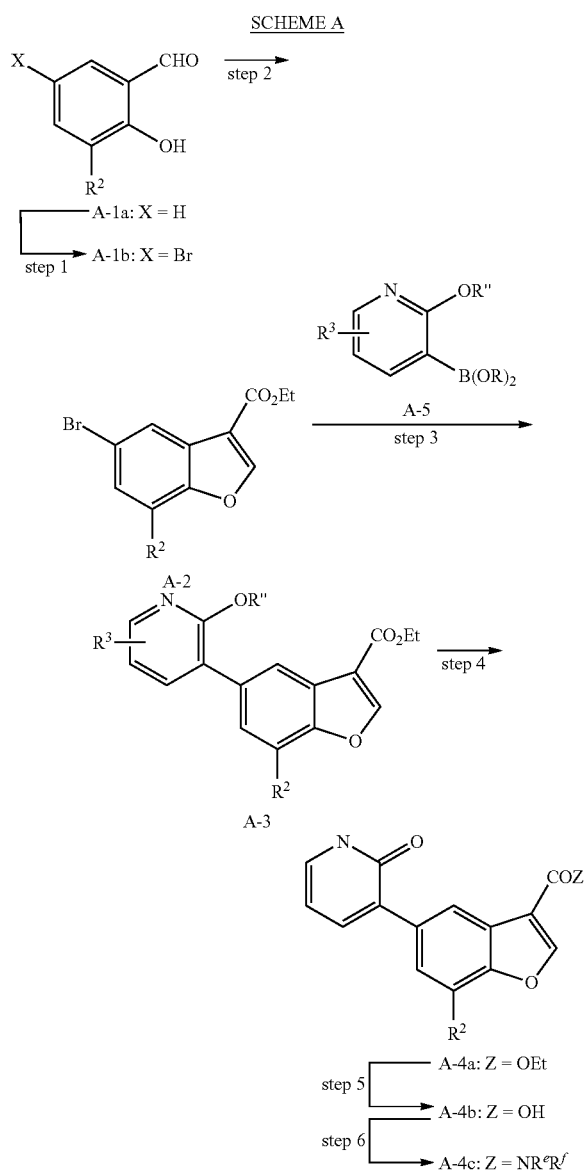

Compounds of the present invention which are 5-(2-oxo-1,2-dihydro-pyridin-3-yl)-7-alkyl-benzofuran-3-carboxylic acid derivatives (A-4) are prepared by condensation of a 3-alkyl-5-bromo-salicylaldehyde (A-1b, $R^2$=alkyl) and ethyl diazoacetate to afford an ethyl 5-bromobenzofuran-3-carboxylate A-2 (M. E. Dudley et al., *Synthesis* 2006 1711-14; *J. Org. Chem.* 2004 69(22):7599) as depicted in SCHEME A. In one aspect of the present invention 5-bromo-salicylaldehyde is readily prepared by bromination of 3-tert-butyl-salicylaldehyde (CAS RN 24623-65-2). The 2-oxo-1,2-dihydro-pyridin-3-yl substituent is introduced into C-5 of the benzofuran by Suzuki coupling of the A-2 and a 2-alkoxy- or 2-benzyloxy-pyridin-3-yl boronic acid (A-5). The resulting pyridinyl ether can be dealkylated to afford the pyridone. Methyl ethers are readily displaced by procedures well known in the art, for example, demethylation with HBr and HOAc affords the pyridone A-4a and MeBr. Benzyl ethers can be cleaved by catalytic hydrogenolysis.

The Suzuki coupling reaction is a palladium-catalyzed coupling of a boronic acid with an aryl or vinyl halide or triflate. Typical catalysts include $Pd(PPh_3)_4$, $PdCl_2(PPh_3)_2$, $Pd(OAc)_2$ and $PdCl_2(dppf)$. With $PdCl_2(dppf)$, primary alkyl borane compounds can be coupled to aryl or vinyl halide or triflate without beta-elimination. The reaction can be carried out in a variety of organic solvents including toluene, THF, dioxane, DCE, DMF, DMSO and MeCN, aqueous solvents and under biphasic conditions. Reactions are typically run from about RT to about 150° C. Additives (e.g., CsF, KF, TlOH, NaOEt and KOH) frequently accelerate the coupling. Although there are numerous components in the Suzuki reaction including the particular palladium catalyst, the ligand, additives, solvent, temperature, etc., numerous protocols have been identified. Highly active catalysts have been described (see, e.g., J. P. Wolfe et al., *J. Am. Chem. Soc.* 1999 121(41):9550-9561 and A. F. Littke et al., *J. Am. Chem. Soc.* 2000 122(17):4020-4028).

The conversion of the ester carboxylic A-4a to an amide A-4c is carried out by well established procedures. Compounds of formula A-4a containing an alkyl ester group, typically a methyl or ethyl ester group, can be hydrolyzed to carboxylic acids under basic reaction conditions (for further reaction conditions see R. C. Larock, *Comprehensive Organic Transformations—A Guide to Functional Group Preparations*, 1989, VCH Publishers Inc., New York; pp. 981-985), preferably using potassium, sodium or lithium hydroxide at room temperature or elevated temperatures in a solvent such as methanol, dioxane, THF, DMF or DMA, or mixtures thereof with $H_2O$ as an optional co-solvent. To enhance the rate of conversion heating may be applied which cab consist of conventional heating or microwave assisted heating might be employed using a suitable microwave irradiation apparatus.

Acylation of an amine by compounds of formula A-4b can be effected by preparing an activated carboxylic acid such as an acid chloride or a symmetrical or mixed acid anhydride and reacting the activated acid with an amine in an inert solvent such as DMF, DCM, THF, with or without water as a co-solvent, at temperatures typically between 0° and 60° C. generally in the presence of a base such as $Na_2CO_3$, $NaHCO_3$, $K_2CO_3$, DIPEA, TEA or pyridine and the like to afford an amide of formula A-4c. Carboxylic acids are converted into the corresponding acid chlorides using standard reagents well known to someone skilled in the art, such as thionyl chloride, oxalyl chloride, phosphoryl chloride and the like. Those reagents can be used in presence of bases such as DIPEA, TEA or pyridine.

Alternatively a carboxylic acid of formula A-4b can be converted in situ into activated acids by different peptide coupling procedures known to those skilled in the art. These activated acids are reacted directly with an amine to afford the compounds of formula A-4c. Said activation with those peptide coupling procedures can involve the use of an activating agent like EDCI, DCC, BOP, PyBrOP, or 2-fluoro-1-methylpyridinium p-toluenesulphonate (Mukaiyama's reagent), and the like, optionally in the presence of modifiers such as HOBt, with or without a base such NMM, TEA or DIPEA in an inert solvent such as DMF or DCM at temperatures between 0° C. and 60° C. The reaction may alternatively be carried out in presence of 0-(7-azabenzotriazol-1-yl)-N,N,N', N'-tetramethyluronium hexafluorophosphate (HATU) or 1-hydroxy-7-azabenzotriazole (HOAt) and TEA or DIPEA in DMF, DCM or THF. Acylation of amines (J. March, supra pp. 417-425; H. G. Benz, *Synthesis of Amides and Related Compounds in Comprehensive Organic Synthesis*, E. Winterfeldt, ed., vol. 6, Pergamon Press, Oxford 1991 pp. 381-411; see R. C. Larock, *Comprehensive Organic Transformations—A Guide to Functional Group Preparations*, 1989, VCH Publishers Inc., New York; pp. 972-976) has been reviewed.

(step 4) to introduce the latent pyridone. (C. Morice et al., *SynLett* 2002, 501)

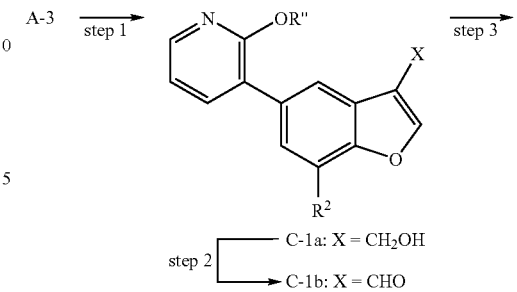

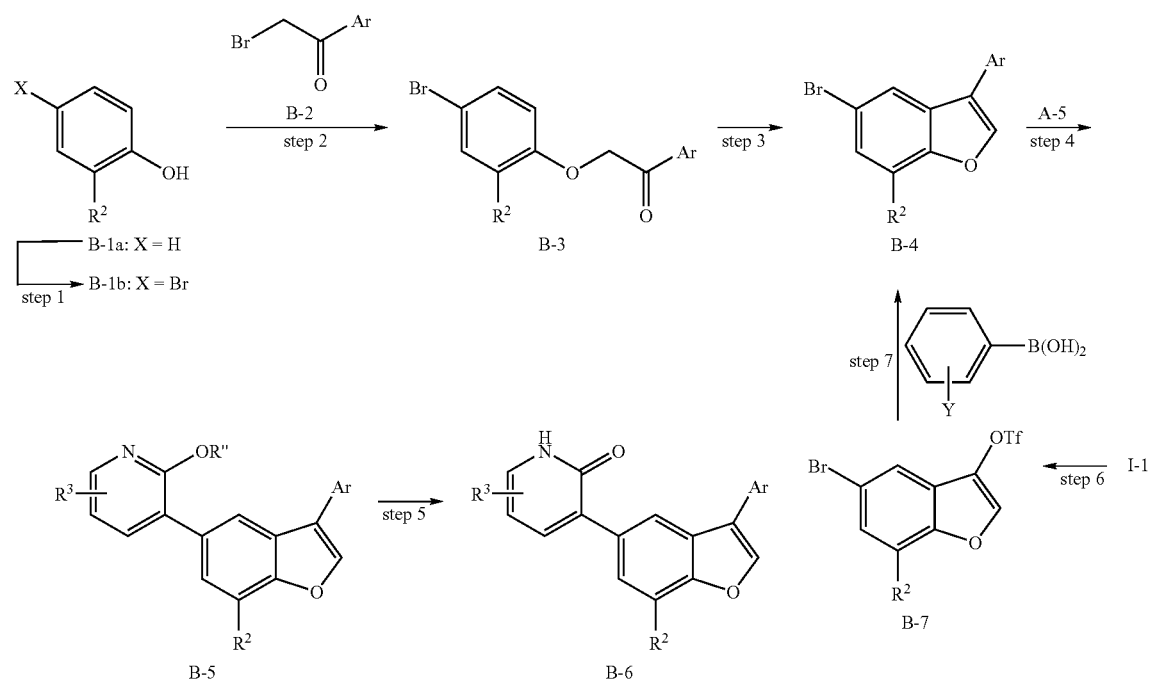

3-Aryl benzofurans can be prepared by cyclization of a 2-phenoxy-1-phenyl-ethanone B-3 irradiation of B-3 in a microwave synthesizer in the presence of montmorillonite KSF. (SCHEME B)(H. M. Meshram, et al. *Synlett* 2000 1273-1274) The requisite starting material is available by alkylation of a 2-alkyl-4-bromo-phenol B-1b with an optionally aryl substituted α-alkylacetophenone. Introduction of the pyridone ring is carried out by Suzuki coupling and dealkylation as depicted in SCHEME A. An alternate route to compounds of formula B-5 utilizes a chemoselective palladium-catalyzed coupling at C-3 of the triflate B-7 with an aryl boronic acid (step 7) and a subsequent palladium catalyzed coupling step -continued

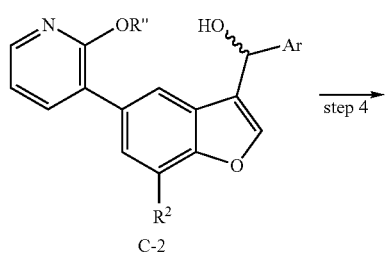

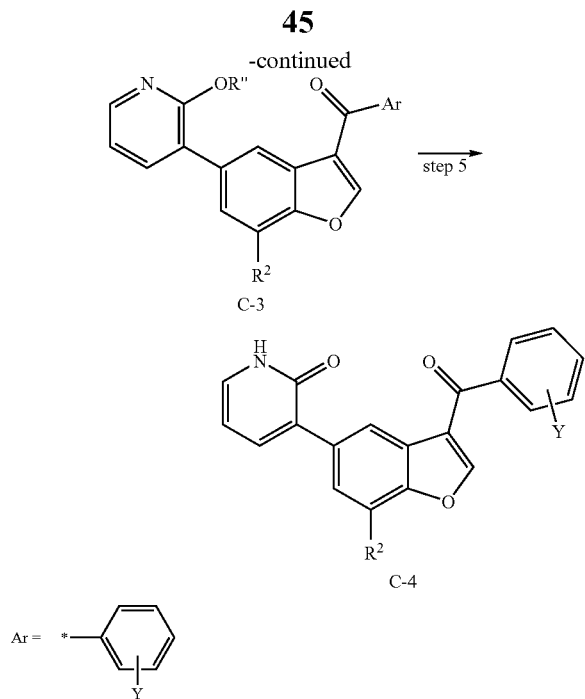

Optionally substituted 3-benzoyl benzofurans C-4 are prepared by addition of a aryl organometallic compound, commonly an aryl Grignard or aryl lithium to C-1b to afford the secondary alcohol C-2 which can be reoxidized to the corresponding ketone. Addition of an organometallic derivative to a ketone is a well documented procedure which is carried out by contacting an aldehyde or ketone with an organometallic reagent in an inert solvent such as Et$_2$O, THF, DME or dioxane at temperatures between 0° C. and −78° C. The oxidation of alcohols to aldehydes, ketones and carboxylic acids is an common transformation in organic synthesis and a correspondingly large number of alternative procedures, conditions and reagents are available which permit the oxidation of almost any alcohol. Among the commonly used reagents are CrO$_3$ or pyridinium dichromate, Jones oxidation (CrO$_3$/acetone), Collins reagent (CrO$_3$/pyridine)) in aqueous, organic or mixed solvents under acidic and basic conditions. Potassium permanganate, MnO$_2$ and Ce(IV) have been used extensively in organic synthesis. DMSO based oxidants including DMSO/DCC (Moffatt Oxidation), DMSO/Ac$_2$O, DMSO/SO$_3$ DMSO/(COCl)$_2$ (Swern Oxidation) in organic solvents in the presence of tertiary amines are often successful. Silver oxide or silver carbonate/CELITE® have been used successfully. The Dess-Martin periodinane run under neutral or near neutral conditions in organic solvents is commonly used. 2,2,6,6-Tetramethylpiperidine 1-oxyl (TEMPO) and sodium hypochlorite has been widely adapted to the oxidation of alcohols.

Conversion of the pyridine C-3 to the corresponding pyridone C-4 can be carried out as described for SCHEME A. One skilled in the art will appreciated that the organometallic reagent can be fully substituted as desired in the final product or the aryl substituent can be modified after the addition/oxidation sequence.

The requisite aldehyde C-1b is readily prepared from A-3. The ester can be reduced to the corresponding alcohol with a hydride reagent such as LiAlH$_4$, diborane or DIBAL in an inert solvent at temperatures between RT and −78° C. in an inert solvent, commonly a hydrocarbon or ethereal solvent. Oxidation of an alcohol is typically carried out in solvents such as DMF, NMP, DMSO, THF, dioxane, and DCM at temperatures between 0° C. and 100° C. Typically used reagents are pyridinium dichromate in methylene chloride (Corey, et al., *Tetrahedron Lett.* 1979 399), DMSO/oxalyl chloride in DCM (Omura, et al., *Tetrahedron* 1978 34:1651), pyridine-sulfur trioxide complex, Dess-Martin periodinane (D. B. Dess, and J. C. Martin, *J. Org. Chem.* 1983 48:4155-4156) or 2-iodoxybenzoic acid (Robert K. Boeckman, Jr., et al. *Collective Volume* 2004 10:696). Benzyl and allylic alcohols are conveniently oxidized with manganese (IV) dioxide. Alternative an acid or ester can be directly reduced to an aldehyde using a hydride reagent such as DIBAL at low temperatures, typically −78° C.

SCHEME D

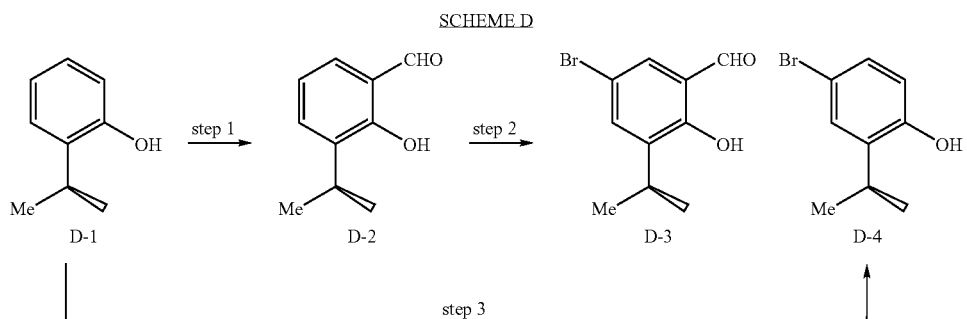

Compounds encompassed by the present invention with a 1-methyl-cyclopropy substituent were prepared from 2-(1-methyl-cyclopropyl)-phenol (D-1, CASRN 4333684-77-6) as depicted in SCHEME D. Alternatively D-1 can be brominated to afford D-4. (J. Berthelot et al. "Regioselective bromination of aromatic compounds I. "Monobromination at the para position of phenols and aromatic amines" *Can. J. Chem.* 1989 67(12):2061) Further elaboration of D-3 or D-4 to compounds of the present invention can be carried out as described in SCHEMES A-C.

Anti-Viral Activity

The activity of the inventive compounds as inhibitors of HCV activity may be measured by any of the suitable methods known to those skilled in the art, including in vivo and in vitro assays. For example, the HCV NS5B inhibitory activity of the compounds of formula I can determined using standard assay procedures described in Behrens et al., *EMBO J.* 1996 15:12-22, Lohmann et al., *Virology* 1998 249:108-118 and Ranjith-Kumar et al., *J. Virology* 2001 75:8615-8623. Unless otherwise noted, the compounds of this invention have demonstrated in vitro HCV NS5B inhibitory activity in such standard assays. The HCV polymerase assay conditions used for compounds of the present invention are described in Example 3. Cell-based replicon systems for HCV have been developed, in which the nonstructural proteins stably replicate subgenomic viral RNA in Huh7 cells (V. Lohmann et al., Science 1999 285:110 and K. J. Blight et al., Science 2000 290:1972. The cell-based replicon assay conditions used for compounds of the present invention are described in Example 22. In the absence of a purified, functional HCV replicase consisting of viral non-structural and host proteins, our understanding of Flaviviridae RNA synthesis comes from studies using active recombinant RNA-dependent RNA-polymerases and validation of these studies in the HCV replicon system Inhibition of recombinant purified HCV polymerase with compounds in vitro biochemical assays may be validated using the replicon system whereby the polymerase exists within a replicase complex, associated with other viral and cellular polypeptides in appropriate stoichiometry. Demonstration of cell-based inhibition of HCV replication may be more predictive of in vivo function than demonstration of HCV NS5B inhibitory activity in vitro biochemical assays Dosage and Administration The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice. "Pharmaceutically acceptable" means that which is useful in preparing a pharmaceutical composition that is generally safe, non-toxic, and neither biologically nor otherwise undesirable and includes that which is acceptable for human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzene-sulfonic acid, 4-chlorobenzenesulfonic acid, 2-naphthalene-sulfonic acid, 4-toluenesulfonic acid, camphorsulfonic acid, 4-methylbicyclo[2.2.2]-oct-2-ene-1-carboxylic acid, gluco-heptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent, such as a nucleoside reverse transcriptase inhibitor, another non-nucleoside reverse transcriptase inhibitor or HIV-1 protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions, and that the treatment of animals includes the treatment of humans as well as other animals. Furthermore, treatment of a HIV-1 infection, as used herein, also includes treatment or prophylaxis of a disease or a condition associated with or mediated by HIV-1 infection, or the clinical symptoms thereof.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

Example 1

N-{(R)-1-[7-tert-Butyl-5-(2-oxo-1,2-dihydro-pyridin-3-yl)-benzofuran-3-carbonyl]-pyrrolidin-3-ylmethyl}-methanesulfonamide (I-73, SCHEME A), 7-tert-butyl-5-(2-oxo-1,2-dihydro-pyridin-3-yl)-benzofuran-3-carboxylic acid ethyl ester (I-3) and 7-tert-butyl-5-(2-oxo-1,2-dihydro-pyridin-3-yl)-benzofuran-3-carboxylic acid (I-4)

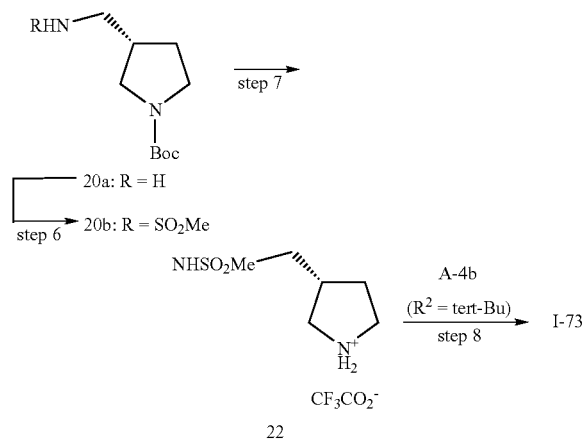

step 1—To a solution of 3-tert-butyl-2-hydroxybenzaldehyde (A-1a, 5.00 g) in DCM (20 mL) at RT was added dropwise a solution of Br$_2$ in DCM (15 mL) over 30 min. The reaction was further stirred for 1 h before the organic volatiles were removed under reduced pressure to afford 7.23 g of A-1b (R$^2$=tert-Bu) as a light yellow solid.

step 2—To a solution of A-1b (5.20 g, R$^2$=tert-Bu) in DCM (40 mL) at RT was added a solution of HBF$_4$.Et$_2$O (54% in Et$_2$O, 548 μL) followed by the dropwise addition of a solution of ethyl diazoacetate (8.30 mL) in DCM (30 mL). After the gas evolution ceased, the organic volatiles were removed under reduced pressure. To the residue was added concentrated H$_2$SO$_4$ (3 mL) and the resulting mixture was stirred for 10 min then diluted with DCM and neutralized with a satd. aq. NaHCO$_3$ solution. The organic layer was separated, washed with brine, dried (Na$_2$SO$_4$) and concentrated. The crude residue was purified by SiO$_2$ chromatography eluting with an EtOAc/hexane gradient (0 to 6% EtOAc) to afford 3.40 g of A-2 (R$^2$=tert-Bu) as an orange solid.

step 3—A sealed tube containing A-2 (1.53 g, R$^2$=tert-Bu), 2-methoxy-3-pyridine boronic acid (1.08 g, CASRN 163105-90-6), Na$_2$CO$_3$ (1.25 g) and Pd(PPh$_3$)$_4$ (543 mg) in a mixture of MeOH (20 mL) and DCM (5 mL) was irradiated in a microwave synthesizer at 120° C. for 45 min. The organic volatiles was removed under reduced pressure. The crude residue was purified by SiO$_2$ chromatography eluting with an EtOAc/hexane gradient (0 to 10% EtOAc) to afford 1.10 g of A-3 (R$^2$=tert-Bu) as colorless oil.

step 4—A solution of A-3 (2.00 g, R$^2$=tert-Bu) in a mixture of 48% HBr (3.13 mL) and HOAc (20 mL) in a sealed tube was heated overnight at 70° C. The reaction mixture was cooled to RT, poured into water, neutralized with a satd. aq. NaHCO$_3$ then extracted with EtOAc. The organic layer was washed with brine, dried (Na$_2$SO$_4$), filtered and concentrated to afford 1.61 g of A-4a (I-3, R$^2$=tert-Bu) as a white solid.

step 5—A solution of A-4a (1.00 g, R$^2$=tert-Bu) in a mixture of 1N aq. LiOH (15 mL) and THF (50 mL) was heated at 45° C. for 3 days. The reaction was cooled RT and acidified with 1N aq. HCl solution then extracted with EtOAc. The organic extract was washed sequentially with water, brine, dried (Na$_2$SO$_4$), filtered and concentrated to give the 950 mg of A-4b (I-4) as a white solid.

step 6—To a solution of (S)-3-(aminomethyl)-1-(tert-butoxycarbonyl)pyrrolidine (320 mg, 20a, CASRN 199175-10-5) in DCM (8 mL) cooled to 0° C. was added pyridine (194 μL) and followed by MsCl (149 μL). The reaction was warmed from 0° C. to RT over 1.5 h before it was quenched with cold water and diluted with EtOAc. The organic layer was washed sequentially with aq. CuSO$_4$ solution, water, brine, then dried (MgSO$_4$), filtered and concentrated.

step 7—To a solution of the crude product from step 6 in DCM (5 mL) at RT was added TFA (0.5 mL). The reaction was stirred for 2 h then concentrated in vacuo. The residue was re-dissolved in DCM and then concentrated. The process was repeated twice more to remove TFA and afford 22.

step 8—To a solution of 22 (70 mg) in DMF (5 mL) cooled to 0° C. was added TEA (54 μL). The mixture was stirred for 15 min then A-4b (40 mg, R$^2$=tert-Bu), HOBt (35 mg), and EDCI (49 mg) were added sequentially. The reaction mixture was warmed 0° C. to RT and stirred for 48 h. The resulting solution was diluted with water and extracted with EtOAc. The organic layer was washed with brine, dried (MgSO$_4$), filtered and concentrated. The crude residue was purified on a preparative TLC plate to afford 0.036 g of I-73. I-72 was prepared analogously except 20a was replaced with (R)-3-(amino methyl)-1-(tert-butoxycarbonyl)pyrrolidine (CASRN 199174-29-3). I-98 and I-92 are prepared in accordance with the procedure for I-72 except in step 2, 2-methoxy-3-pyridine boronic acid is replaced with B-(2-methoxy-6-methyl-3-pyridinyl)-boronic acid (CASRN 1000802-75-4) and B-(5-fluoro-2-methoxy-3-pyridinyl)-boronic acid (CASRN 957120-32-0), respectively.

I-106, I-107 and I-108 are prepared by the same procedure as I-72 except in step 6, mesyl chloride is replace with ethylsulfonyl chloride, cyclopropylsulfonyl chloride and iso-propylsulfonyl chloride, respectively.

I-100, I-101, I-46 and I-47 are prepared analogously except 20a is replaced with N—(S)-1-piperidin-3-ylmethyl-methanesulfonamide (CASRN 1016167-99-9), N-(R)-1-piperidin-3-ylmethyl-methanesulfonamide (CASRN 879275-33-9), (R)-3-amino-piperidine-1-carboxylic acid tert-butyl ester (CASRN 188111-79-7) and (S) 3-amino-piperidine-1-carboxylic acid tert-butyl ester (CASRN 625471-18-3) respectively.

The following are prepared according to the above procedure except steps 6 and 7 are omitted and the amide coupling is carried out as described in step 8 except 22 is replaced with the amine in parenthesis: I-9 (isopropyl amine), I-10 (isobutyl amine), I-11 (isobutyl methyl amine), I-12 (piperidin-4-ol), I-13 (piperidine), I-14 (piperidin-3-yl-methanol), I-15 (morpholin-2-yl-methanol), I-16 ((R)-1-pyrrolidin-2-yl-methanol), I-17 ((S)-1-pyrrolidin-2-yl-methanol), I-18 ((1-aminocyclopentyl)-methanol, CASRN 10316-79-7), I-19 bis-(2- methoxy-ethyl)-amine, I-22 (methylamine), I-23 (aniline), I-25 (ethyl-(2-methoxy-ethyl)-amine), I-27 (3-hydroxy-piperidine), I-38 ((R)-piperidin-3-yl-carbamic acid tert-butyl ester), I-40 ((S)-piperidin-3-yl-carbamic acid tert-butyl ester), I-39 (piperidin-4-yl-carbamic acid tert-butyl ester), I-43 (piperidin-3-ylmethyl-carbamic acid tert-butyl ester), I-45 (pyrrolidin-3-ylmethyl-carbamic acid tert-butyl ester), I-51 (pyrrolidine), I-53 (dimethyl-(S)-pyrrolidin-3-yl-amine, CASRN 132883-44-4), I-54 (1-methyl-[1,4]diazepane, CASRN 4318-37-0), I-58 (piperidine-4-carboxylic acid amide, CASRN 39546-32-2), I-61 (piperidine-3-carboxylic acid amide CASRN 4138-26-5), I-63 ((2S,4R)-4-hydroxy-pyrrolidine-2-carboxylic acid methyl ester, CASRN 1499-56-5), I-64 (4-hydroxy-piperidine-4-carboxylic acid amide, CASRN 693285-66-4), I-65 (3-hydroxy-pyrrolidine, CASRN 40499-83-0), I-66 (4-ethylamino-piperidine-4-carboxylic acid amide, CASRN 84100-54-9), I-67 (dimethyl-(R)-pyrrolidin-3-yl-amine, CASRN 132958-72-6), I-68 (4,4-difluoro-piperidine, CASRN 21987-29-1), I-69 (3,3-dimethyl-piperidine, CASRN 1193-12-0), I-70 (pyrrolidin-3-yl-methanol, CASRN 5082-74-6), I-71 (thiazolidine, CASRN 504-78-9), I-83 (N-(3-aminophenyl)methanesulfonamide, CASRN 37045-73-1), I-84 (2-amino-thiazole), I-85 (N-(3-amino-benzyl)-methanesulfonamide, CASRN 856193-46-9), I-94 (azetidine), I-95 (azetidin-3-yl-methanol, CASRN 95849-02-8), I-102 (azetidin-3-ol, CASRN 45347-82-8).

The following are prepared according to the above procedure except step 6 is omitted, the coupling is in accord with step 8 except 22 is replaced with the amine in parentheses and the Boc protecting group subsequently is removed as described in step 7 (supra): I-41 ((S)-piperidin-3-yl-carbamic acid tert-butyl ester), I-42 ((R)-piperidin-3-yl-carbamic acid tert-butyl ester), I-48 (3-(tert-butoxycarbonylamino)pyrrolidine, CASRN 99724-19-3), I-49 ((pyrrolidin-3-ylmethyl) carbamic acid tert-butyl ester, CASRN 149366-29-6).

I-75 is prepared by acetylation of I-49 with acetic anhydride and pyridine. I-60 is prepared by trifluoroacetylation of I-49 with TFAA and pyridine.

I-103 is prepared according to the above procedure except step 6 and 7 are omitted, the amide is prepared in accord with step 8 except 22 was replaced with (tert-butyl azetidin-3-ylmethyl-carbamate, CASRN 91188-15-7), the Boc protecting group subsequently is removed as described in step 7 (supra) and the resulting primary amine contacted with mesyl chloride and pyridine.

I-29 is prepared according to the above procedure except step 6 and 7 are omitted and the amide is prepared in accord with step 8 except 22 was replaced with piperidin-4-yl-carbamic acid tert-butyl ester (CASRN 73874-95-0) and the Boc protecting group subsequently is removed as described in step 7 (supra): I-99 is prepared by sulfonylation of I-29 with mesyl chloride and pyridine.

I-104, I-109 and I-50 are prepared according to the above procedure except steps 6 and 7 are omitted and the amide is prepared in accord with step 8 except 22 is replaced with methyl-piperidin-3-ylmethyl-carbamic acid tert-butyl ester (CASRN 169750-76-9) and tert-butyl morpholin-2-ylmethyl-carbamate CASRN 173341-02-1) and (piperidin-3-ylmethyl)carbamic acid tert-butyl ester, (CASRN 142643-29-6), respectively. The Boc protecting group subsequently is removed as described in step 7 (supra) and the amine is sulfonylated with mesyl chloride and pyridine. I-90 is prepared by sulfonylation of I-50 with mesyl chloride and pyridine.

I-28 is prepared according to the above procedure except steps 6 and 7 are omitted and the amide coupling is carried out as described in step 8, except 22 is replaced with piperazine-1-carboxylic acid tert-butyl ester (CASRN 57260-71-6) after which the protecting group is removed as described in step 7. I-52 is prepared by acetylation of I-28 with acetic anhydride and pyridine. I-55 is prepared by trifluoroacetylation of I-28.

Example 2

3-[7-tert-Butyl-5-(2-oxo-1,2-dihydro-pyridin-3-yl)-benzofuran-3-yl]-benzamide (I-78, SCHEME B)

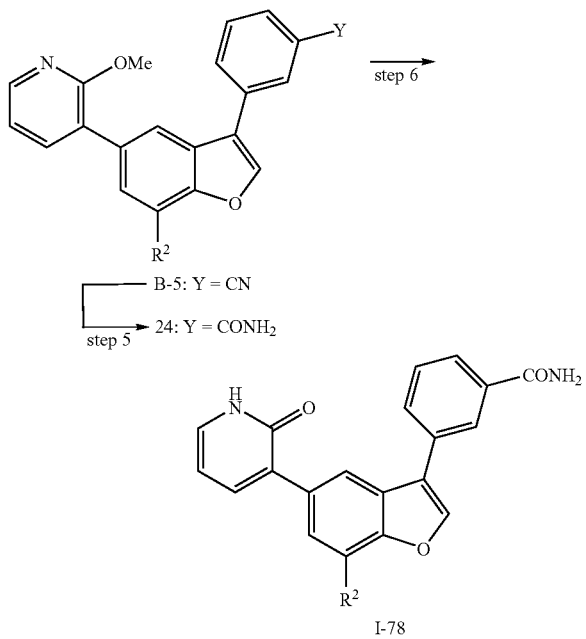

step 2—A tube was charged with a mixture of B-1b (0.50 g, $R^2$=tert-Bu, CASRN 10323-39-4), 3-(2-bromoacetyl)benzonitrile (0.60 g, B-2, Y=CN) and $Na_2CO_3$ (522 mg) in acetone (10 mL), sealed and irradiated in a microwave reactor at 120° C. for 3 h. The reaction was cooled to RT and the resulting solid was filtered off. The filterate was concentrated and the residue partitioned between EtOAc and water. The organic layer was separated, dried ($MgSO_4$), filtered and concentrated. The crude residue was purified by $SiO_2$ chromatography eluting with an EtOAc/hexane gradient (5 to 15% EtOAc) to afford 0.58 g of B-3 ($R^2$=tert-Bu, Y=3-CN) as a white solid.

step 3—A tube was charged with B-3 (0.50 g), montmorillonite KSF (1.00 g) and DCM (3 mL), sealed and irradiated in a microwave reactor at 150° C. for 3 h. The reaction mixture was cooled to RT. The solid was filtered, rinsed with DCM, and the filtrate was concentrated. The crude residue was purified by $SiO_2$ chromatography eluting with 5% EtOAc/hexane to afford 0.287 g of B-4 ($R^2$=tert-Bu, Ar=3-cyanophenyl) as a white solid.

step 4—A tube was charged with B-4 (120 mg), 2-methoxy-3-pyridine boronic acid (78 mg), $Na_2CO_3$ (54 mg) and Pd(dppf)$_2$Cl$_2$.CH$_2$Cl$_2$ (14 mg), MeOH (4 mL) and DCM (1 mL), sealed and irradiated in a microwave reactor at 115° C. for 30 min. The organic volatiles were removed under reduced pressure. The crude residue was purified by $SiO_2$ chromatography eluting with an EtOAc/hexane gradient (2-25% EtOAc) to afford 122 mg of B-5 ($R^2$=tert-Bu, Ar=3-cyanophenyl).

step 5—A mixture of B-5 (120 mg) and hydrido(dimethylphospinous acid-kp)[hydrogen bis(dimethylphospinito-kp)]platinum (18 mg, CASRN 173416-05-2) in EtOH (15 mL) was heated at reflux for 6.5 h at which time the starting material was consumed. The organic volatiles were removed under reduced pressure. The crude residue was purified by SiO$_2$ chromatography eluting with an EtOAc/hexane gradient (40 to 100% EtOAc) to afford 107 mg of 24 as a foam.

step 6—A tube was charged with 24 (100 mg), 48% HBr (0.12 mL) and HOAc (2 mL), sealed and heated at 70° C. for 26 h. The reaction mixture was cooled to RT, carefully poured into a satd. aq. NaHCO$_3$ solution and extracted with EtOAc. The organic layer was washed with brine, dried (MgSO$_4$), filtered and concentrated. The residue was purified on a preparative SiO$_2$ TLC plate to afford 43 mg of I-78 as a solid.

I-32 is prepared analogously except step 5 was omitted and B5 (R$^2$=tert-Bu, Ar=3-cyanophenyl) is dealkylated as described in step 6.

I-87 is prepared analogously except in step 2,3-(2-bromoacetyl)benzonitrile was replaced with 4-(2-bromoacetyl)benzonitrile. I-35 is prepared analogously except step 5 was omitted.

I-33 is prepared analogously except in step 2, 3-(2-bromoacetyl)benzonitrile is replaced with 2-bromo-1-(3-methoxy-phenyl)-ethanone. I-34 is prepared by dealkylation of I-33 according to step 6 of example 4.

Example 3

N-{4-[7-tert-Butyl-5-(2-oxo-1,2-dihydro-pyridin-3-yl)-benzofuran-3-yl]-benzyl}1-methanesulfonamide
(I-37)

step 2—A tube was charged B-1b (1.90 g, R$^2$=tert-Bu), 2-bromo-4'-cyano-acetophenone (1.31 g), Na$_2$CO$_3$ (1.40 g) and acetone (15 mL), sealed and irradiated in a microwave synthesizer at 120° C. for 3 h. The reaction was cooled to RT then the solid was filtered. The filtrate was concentrated and the residue partitioned between EtOAc and water. The organic layer was separated, washed with brine, dried (MgSO$_4$), filtered and concentrated. The crude residue was purified by SiO$_2$ chromatography eluting with an EtOAc/hexane gradient (5 to 10% EtOAc) to afford 1.21 g of B-3 (Ar=3-cyanophenyl, R$^2$=tert-Bu) as a white solid.

step 3—A tube was charged with B-3 (0.45 g), montmorillonite KSF (1.00 g) and DCM (6 mL), sealed and irradiated in the microwave synthesizer at 120° C. for 2 h. The reaction mixture was cooled to RT. The solid was filtered off, washed with DCM, and the filtrate was concentrated. The crude residue was purified by SiO$_2$ chromatography eluting with 5% EtOAc/hexanes to afford 238 mg of B-4 (R$^2$=tert-Bu, Ar=4-cyanophenyl) as a white solid.

step 4—A mixture of B-4 (R$^2$=tert-Bu, Ar=4-cyanophenyl, 190 mg) and Raney nickel (1 mL slurry in water) in MeOH (30 mL) was stirred under 1 atmosphere of H$_2$ at RT for 2.5 h. The catalyst was filtered off, and the filtrate was concentrated. The crude residue was purified by SiO$_2$ chromatography eluting with a MeOH/DCM gradient (1 to 10% MeOH) to afford 154 mg of B-4 (R$^2$=tert-Bu, Ar=4-aminomethyl-phenyl) as an off-white solid.

step 5—To a solution of B-4 (104 mg, R$^2$=tert-Bu, Ar=4-aminomethyl-phenyl) in DCM at 0° C. was added sequentially pyridine (59 μL) and MeSO$_2$Cl (27 μL). The reaction mixture was warmed from 0° C. to RT over 1 h. The reaction was quenched with 1N aq. HCl solution and diluted with EtOAc. The organic layer was washed sequentially with aq. CuSO$_4$ solution, water, brine, dried (MgSO$_4$), filtered and concentrated. The crude residue was purified by SiO$_2$ chromatography eluting with an EtOAc/hexane gradient (5 to 50% EtOAc) to afford 138 mg of B-4 (R$^2$=tert-Bu, Ar=4-MeSO$_2$HNCH$_2$C$_6$H$_4$) as an off-white solid.

step 6—A tube was charged with B-4 (62 mg, R$^2$=tert-Bu, Ar=4-MeSO$_2$HNCH$_2$C$_6$H$_4$), 2-methoxy-3-pyridine boronic acid (33 mg), Na$_2$CO$_3$ (23 mg), Pd(dppf)$_2$Cl$_2$.CH$_2$Cl$_2$ (6 mg) MeOH (4 mL) and DCM (0.5 mL), sealed and irradiated in a microwave synthesizer at 115° C. for 30 min. The organic volatiles were removed under reduced pressure. The crude residue was purified by SiO$_2$ chromatography eluting with an EtOAc/hexane gradient (20 to 50% EtOAc) to afford 59 mg of B-5 (R$^2$=tert-Bu, Ar=4-MeSO$_2$HNCH$_2$C$_6$H$_4$).

step 7—A tube was charged with B-5 (58 mg), 48% HBr (0.2 mL) and AcOH (3.5 mL), sealed and heated at 70° C. for 6.5 h. The reaction mixture was cooled at RT, carefully poured into a satd. aq. NaHCO$_3$ solution and extracted with EtOAc. The organic layer was washed with brine, dried (MgSO$_4$), filtered and concentrated. The residue was purified on a preparative SiO$_2$ TLC plate to afford 40 mg of I-37 as a white solid.

I-81 is prepared analogously except in step 2,2-bromo-4'-cyano-acetophenone is replaced with 2-bromo-3'-cyano-acetophenone. I-59 and I-62 are prepared analogously to I-37 and I-81 respectively except in both instances step 5 is omitted and I-62 was prepared by Suzuki coupling of 2-benzyloxy-pyridin-3-boronic acid and debenzylated by catalytic hydrogenolysis.

I-74 is prepared analogously to I-37 except in step 6,2-methoxy-3-pyridine boronic acid is replaced with B-(5-fluoro-2-methoxy-3-pyridinyl)-boronic acid (CASRN 957120-32-0).

Example 4

3-[7-tert-Butyl-3-(3-methoxy-benzoyl)-benzofuran-5-yl]-1H-pyridin-2-one (I-30) and 3-[7-tert-Butyl-3-(3-hydroxy-benzoyl)-benzofuran-5-yl]-1H-pyridin-2-one (I-36, SCHEME C)

step 1—To a solution of A-3 (1.00 g, R$^2$=tert-Bu, R$^3$=H and R"=Me) and toluene (50 mL) cooled to −78° C. was added dropwise a solution of DIBAL (1.5M in toluene, 3.7 mL). The reaction was stirred and warmed from −78° C. to 0° C. over 3 h then quenched with aq. solution of Rochelle's salt. The reaction mixture was extracted with EtOAc. The organic layer was washed with brine, dried (Na$_2$SO$_4$), filtered and concentrated. The crude residue was purified by SiO$_2$ chromatography eluting with an EtOAc/hexane gradient (5 to 50% EtOAc) to afford 650 mg of C-1a as a foam.

step 2—To a solution C-1a (650 mg, R$^2$=tert-Bu, R$^3$=H and R"=Me) in DCM (30 mL) at 0° C. was added Dess-Martin periodinate (1.69 g). The reaction was stirred and warmed from 0° C. to RT overnight then diluted with water and extracted with DCM. The organic layer was dried (Na$_2$SO$_4$) and concentrated. The residue was purified on a preparative SiO$_2$ TLC plate developed with 30% EtOAc in hexanes to afford 647 mg of C-1b.

step 3—To a solution of C-1b (210 mg, R$^2$=tert-Bu, R$^3$=H and R"=Me) in THF (10 mL) cooled to 0° C. was added a solution of 3-methoxyphenyl magnesium bromide in THF (1.0M in THF, 1.36 mL). The reaction was stirred and warmed from 0° C. to RT over 2 h then quenched with a satd. aq. NH$_4$Cl and extracted with EtOAc. The organic layer was washed with brine, dried (Na$_2$SO$_4$) filtered and concentrated. The residue was purified on a preparative SiO$_2$ TLC plate developed with 35% EtOAc/hexanes to afford 250 mg of C-2 (R$^2$=tert-Bu, R"=Me and Ar=3-MeO—C$_6$H$_4$) as a yellowish oil.

step 4—To a solution C-2 (250 mg, R$^2$=tert-Bu and R"=Me) in DCM (10 mL) at 0° C. was added Dess-Martin periodinate (508 mg). The reaction was stirred and warmed from 0° C. to RT over 3 h then diluted with water and extracted with DCM. The organic layer was dried (Na$_2$SO$_4$), filtered and concentrated. The residue was purified by preparative SiO$_2$ TLC developed with 30% EtOAc/hexanes to afford 150 mg of C-3 (R$^2$=tert-Bu, R"=Me and Ar=3-MeO—C$_6$H$_4$) as a solid.

step 5—A mixture of C-3 (150 mg), 48% HBr (0.20 mL) and AcOH (2 mL) in a sealed tube was heated overnight at 70° C. The reaction mixture was cooled to RT, carefully poured into water, made basic with K$_2$CO$_3$ and then extracted with EtOAc. The organic layer was washed with brine, dried (Na$_2$SO$_4$), filtered and concentrated. The residue was purified by preparative SiO$_2$ TLC developed with 7% MeOH/DCM to afford 90 mg of I-30 as a solid.

step 6—To solution of I-30 (70 mg) in DCM cooled to −78° C. was added a solution of BBr$_3$ (1.0M in DCM, 520 µL). The reaction was stirred for 30 min at −78° C., then slowly warmed up to RT slowly and stirred for 2 d. The reaction was quenched with 1N aq. HCl solution and extracted with EtOAc. The organic layer was separated, dried (MgSO$_4$), filtered and concentrated. The crude residue was purified by preparative SiO$_2$ TLC developed with 50% EtOAc/hexanes to afford 55 mg of I-36 as a light tan-colored solid.

I-20 and I-31 are prepared analogously except in step 3,3-methoxy-phenyl magnesium bromide was replaced with phenyl magnesium bromide and 3-methyl-thien-2-yl magnesium bromide.

Example 5

[7-tert-Butyl-5-(2-oxo-1,2-dihydro-pyridin-3-yl)-benzo furan-3-yl]-acetonitrile (I-5) and [7-tert-Butyl-5-(2-oxo-1,2-dihydro-pyridin-3-yl)-benzo furan-3-yl]-acetic acid (I-6)

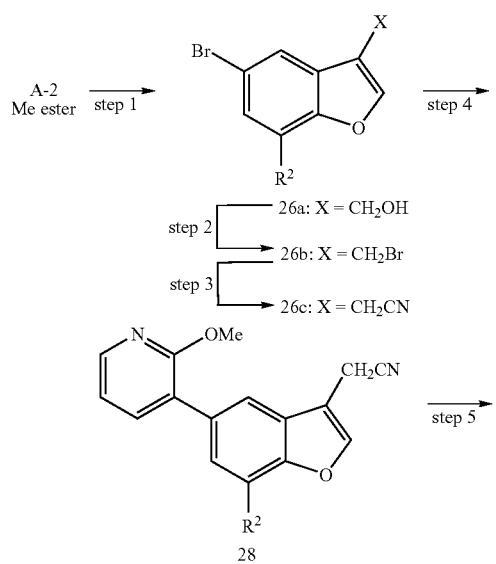

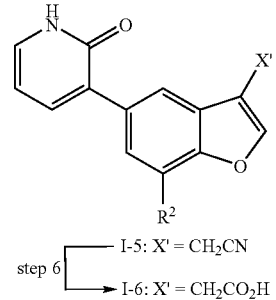

step 1—To a solution of A-2 (645 mg, 1.985 mmol, methyl ester) in toluene (8 mL) cooled to −78° C. was added a solution of DIBAL-H (1.5M in toluene, 4.00 mL, 6.0 mmol). The reaction was gradually warmed to RT over 2 h then cooled to 0° C., quenched carefully with aq. Rochelle's salt, and diluted with EtOAc. The resulting suspension was stirred vigorously for 30 min. The organic layer was washed sequentially with water, brine, dried (Na$_2$SO$_4$), filtered and concentrated. The crude residue was purified by SiO$_2$ chromatography eluting with an EtOAc/hexane gradient (10 to 15% EtOAc) to afford 353 mg (63%) of 26a as a colorless oil.

step 2—To a solution of 26a (353 mg, 1.247 mmol) and CBr$_4$ (472 mg, 1.423 mmol) in DCM (5 mL) cooled to 0° C. was added dropwise a solution of Ph$_3$P (359 mg, 1.370 mmol) in DCM (5 mL). The reaction mixture was gradually warmed to RT and stirred overnight then concentrated. The crude residue was purified by SiO$_2$ chromatography eluting with an EtOAc/hexane gradient (0 to 10% EtOAc) to afford 0.344 mg (80%) of 26b as a colorless oil.

step 3—To a solution of 26b (344 mg, 0.994 mmol) in DMF (3 mL) was added sodium cyanide (79 mg, 1.612 mmol). The reaction mixture was stirred overnight at RT then diluted with EtOAc. The organic layer was washed sequentially with 1N aq. HCl solution, water and brine, dried (Na$_2$SO$_4$), filtered and concentrated. The crude residue was purified by SiO$_2$ chromatography eluting with an EtOAc/hexane gradient (0 to 4% EtOAc) to afford 247 mg (85%) of 26c as a white solid.

step 4—A sealed was charged with 26c (128 mg, 0.438 mmol), 2-methoxy-3-pyridine boronic acid (119 mg, 0.778 mmol), Pd(PPh$_3$)$_4$ (42 mg, 0.036 mmol) and Na$_2$CO$_3$ (135 mg, 1.274 mmol) in a mixture of MeOH (3 mL) and DCM (1 mL), sealed and irradiated in a microwave synthesizer at 115° C. for 20 min. The reaction mixture was concentrated, diluted with EtOAc, washed with brine, dried (Na$_2$SO$_4$), filtered and concentrated. The crude residue was purified by SiO$_2$ chromatography eluting with an EtOAc/hexane gradient (5 to 10% EtOAc) to afford 124 mg (88%) of 28 as a pale yellow oil.

step 5—A mixture of 28 (124 mg, 0.388 mmol), 48% HBr (0.125 mL, 1.089 mmol) and HOAc (3 mL) in a sealed tube was heated overnight at 60° C. The reaction mixture was cooled to RT, carefully poured into a cold satd. aq. NaHCO$_3$, and extracted with EtOAc. The organic layer was washed with brine, dried (Na$_2$SO$_4$), filtered and concentrated. The crude residue was purified by SiO$_2$ chromatography eluting with an EtOAc/hexane gradient (25 to 100% EtOAc) to afford 61 mg (51%) of I-5 as a white solid.

step 6—A solution of I-5 (42 mg, 0.137 mmol) in sulfuric acid (1 mL), HOAc (1 mL), and water (1 mL) was heated at reflux for 4 h. The reaction mixture was cooled to RT then carefully poured into ice water. The reaction mixture was adjusted to pH 5 with satd. aq. NaHCO$_3$, and extracted with EtOAc. The organic layer was washed with brine, dried (Na$_2$SO$_4$), filtered and concentrated. The crude residue was purified on a preparative SiO$_2$ TLC plate developed with 10% MeOH/DCM to afford 17.8 mg (40%) of I-6 as a white solid.

Example 6

3-(7-tert-Butyl-3-oxo-2,3-dihydro-benzofuran-5-yl)-1H-pyridin-2-one (I-1)

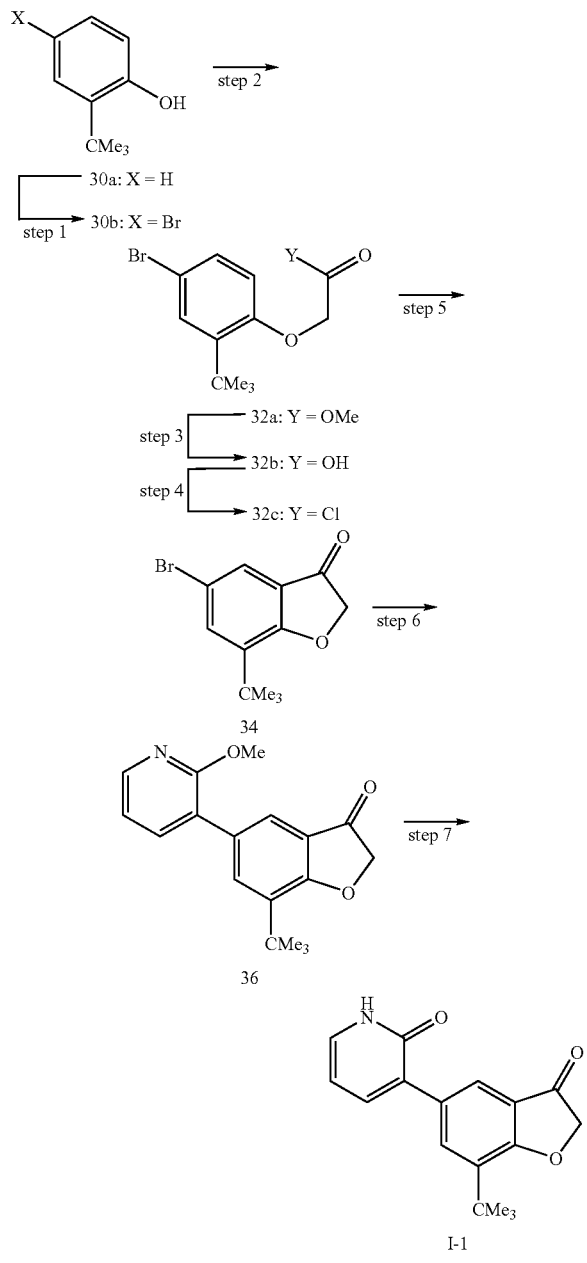

step 1—To a solution of 30a (4.20 mL, 27.34 mmol) in MeOH (80 mL) and DCM (120 mL) was added tetrabutylammonium tribromide (15.66 g, 32.48 mmol). After stirring for 1 h at RT, the reaction was concentrated. The residue was diluted with Et$_2$O. The organic layer was washed sequentially with 1N aq. HCl solution, brine, dried (Na$_2$SO$_4$), filtered and concentrated. The crude residue was purified by SiO$_2$ chromatography eluting with an EtOAc/hexane gradient (5 to 10% EtOAc) to afford 5.13 g (82%) of 30b as a pale yellow oil.

step 2—A mixture of 30b (2.00 g, 8.73 mmol), methyl bromoacetate (0.90 mL, 9.51 mmol) and K$_2$CO$_3$ (4.27 g, 30.90 mmol) in MeOH (20 mL) was heated at reflux overnight. The reaction was cooled to RT before the solid was filtered off and the filtrate was concentrated. The residue was diluted with EtOAc, washed with water, brine, dried (Na$_2$SO$_4$), filtered and concentrated to afford 2.44 g (93%) of 32a as a colorless oil.

step 3—To a solution of 32a (2.44 g, 8.106 mmol) in THF (10 mL), MeOH (10 mL) and water (10 mL) was added LiOH.H$_2$O (3.40 g, 80.952 mmol). The reaction mixture was stirred overnight at RT then the organic volatiles were evaporated. The residue was diluted with EtOAc, and neutralized with 6N aq. HCl (13 mL). The organic layer was separated, dried (Na$_2$SO$_4$), filtered and concentrated to afford 1.98 g (85%) of 32b as a white solid.

step 4—To a solution of 32b (1.98 g, 6.90 mmol) in DCM (20 mL) was added SOCl$_2$ (0.650 mL, 8.91 mmol) and DMF (2 drops). The reaction mixture was heated at reflux for 4 h. The reaction mixture was cooled to RT then concentrated in vacuo to afford 32c which was used directly in step 5.

step 5—To a solution of 32c (6.90 mmol) in DCM (15 mL) cooled to 0° C. was added AlCl$_3$ (1.44 g, 10.80 mmol). The reaction was gradually warmed to RT and stirred overnight. The reaction mixture was carefully quenched by slow addition of ice water, and extracted with EtOAc. The organic layer was washed with brine, dried (Na$_2$SO$_4$), filtered and concentrated. The crude residue was purified by SiO$_2$ chromatography eluting with an EtOAc/hexane gradient (0 to 5% EtOAc) to afford 392 mg of 34 as a white solid.

step 6—A tube was charged with 34 (85 mg, 0.556 mmol), 2-methoxy-3-pyridine boronic acid (99 mg, 0.367 mmol), Pd(PPh$_3$)$_4$ (40 mg, 0.035 mmol) and Na$_2$CO$_3$ (110 mg, 1.038 mmol) and a mixture of MeOH (3 mL) and DCM (1 mL), sealed and irradiated in a microwave synthesizer at 115° C. for 30 min. The organic volatiles were evaporated and the residue was partitioned between EtOAc and water. The organic layer was washed with brine, dried (Na$_2$SO$_4$), filtered and concentrated. The crude residue was purified by SiO$_2$ chromatography eluting with 10% EtOAc/hexanes to afford 46 mg (42%) of 36 as a colorless oil.

step 7—A mixture of 36 (46 mg, 0.1554 mmol), 48% HBr (0.050 mL) and AcOH (2.5 mL) in a sealed tube was heated overnight at 70° C. The reaction mixture was cooled to RT, carefully poured into cold satd. aq. NaHCO$_3$, and extracted with EtOAc. The organic layer was washed with brine, dried (Na$_2$SO$_4$), filtered and concentrated. The crude residue was purified on a preparative SiO$_2$ TLC plate developed with 50% EtOAc/hexanes to afford 6.8 mg (16%) of I-1 as a light yellow solid.

Example 7

3-(7-tert-Butyl-benzofuran-5-yl)-1H-pyridin-2-one (I-2)

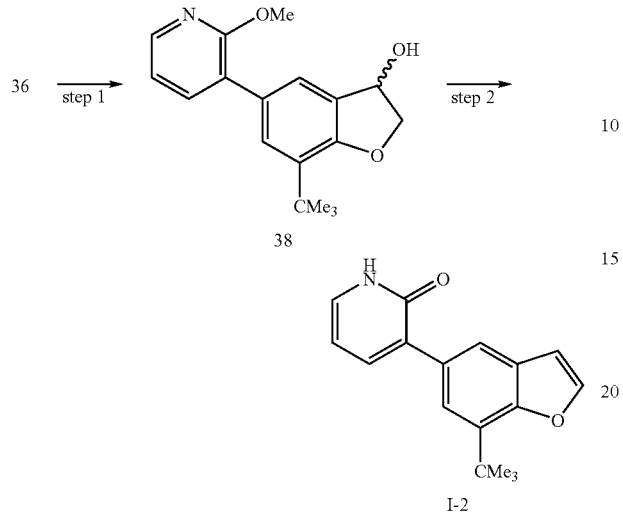

step 1—To a solution of 36 (78 mg, 0.263 mmol) in MeOH (2 mL) and EtOAc (2 mL) was added Pd(OH)$_2$ (20% wt. on carbon, 28.6 mg, 0.041 mmol). The reaction was stirred at RT under an atmosphere of H$_2$ for 20 min. The reaction mixture was transferred to a Parr bottle and was shaken overnight under 42 psi atmosphere of H$_2$ at RT. An additional aliquot of Pd(OH)$_2$/C (66 mg) was added during the process. The catalyst was filtered off. The filtrate was concentrated to give a mixture of the desired benzyl alcohol product and I-1.

The crude product was dissolved in MeOH (2 mL) at RT and NaBH$_4$ (14 mg, 0.368 mmol) was added. The reaction mixture was stirred for 20 min then quenched with 10% aqueous NaHSO$_4$ solution and extracted with EtOAc. The organic layer was washed with brine, dried (Na$_2$SO$_4$), filtered and concentrated. The crude product containing the desired benzyl alcohol 38 was carried on without further purification.

step 2—A mixture of 38, 48% HBr (0.070 mL) and HOAc (3 mL) in a sealed tube was heated overnight at 60° C. The reaction mixture was cooled to RT, carefully poured into cold satd. aq. NaHCO$_3$, and extracted with EtOAc. The organic layer was washed with brine, dried (Na$_2$SO$_4$), filtered and concentrated. The crude residue was purified on a preparative SiO$_2$ TLC plate and developed with 66% EtOAc/hexanes to afford 21 mg (35% over 2 steps) of I-2 as a light yellow solid.

Example 8

7-tert-Butyl-5-(2-oxo-1,2-dihydro-pyridin-3-yl)-2,3-dihydro-benzo furan-3-carboxylic acid methyl ester (I-26)

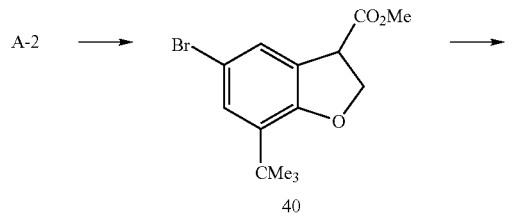

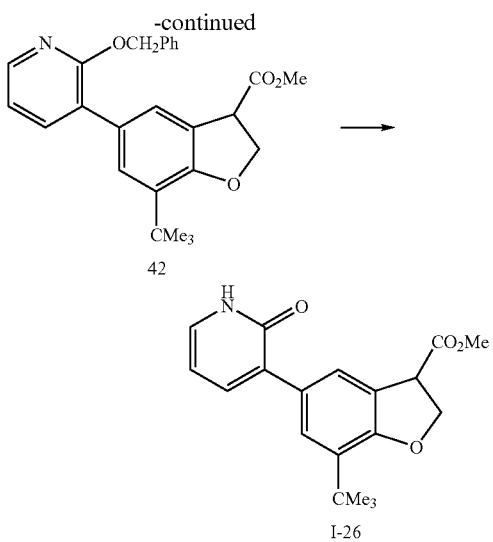

step 1—To a solution A-2 (250 mg, R$^2$=tert-Bu) in MeOH (10 mL) at RT was added Mg (392 mg). The reaction was stirred overnight then quenched with 1N aq. HCl and extracted with EtOAc. The organic layer was washed with brine, dried (Na$_2$SO$_4$), filtered and concentrated. The crude residue was purified on a preparative SiO$_2$ TLC plate developed with 25% EtOAc/hexanes to afford 80 mg of 40 as a colorless oil.

step 2—A tube was charged with 40 (80 mg), 2-benzoxy-3-(4,4,5,5-tetramethyl-[1,3,2]dioxaborolan-2-yl)-pyridine (119 mg), Na$_2$CO$_3$ (68 mg), Pd(PhP$_3$)$_4$ (30 mg) and a mixture of MeOH (4 mL) and DCM (1 mL), sealed and irradiated in a microwave synthesizer at 120° C. for 30 min. The organic volatiles were removed under reduced pressure. The residue was partitioned between EtOAc and water. The organic layer was washed with brine, dried (Na$_2$SO$_4$), filtered and concentrated. The crude residue was purified on a preparative SiO$_2$ TLC plate developed with 30% EtOAc/hexanes to afford 43 mg of 42.

step 3—A mixture of 42 (43 mg) and Pd/C (10% wt. on carbon, 5 mg) in MeOH (3 mL) at RT was stirred under 1 atmosphere of H$_2$ for 1 h. The catalyst was filtered and the filtrate was concentrated. The crude residue was purified on a preparative SiO$_2$ TLC plate developed with EtOAc to afford 15 mg of I-26 as a light tan-solid.

Example 9

N-{4-[7-tert-Butyl-5-(2-oxo-1,2-dihydro-pyridin-3-yl)-benzofuran-3-yl]-phenyl}-methanesulfonamide (I-79)

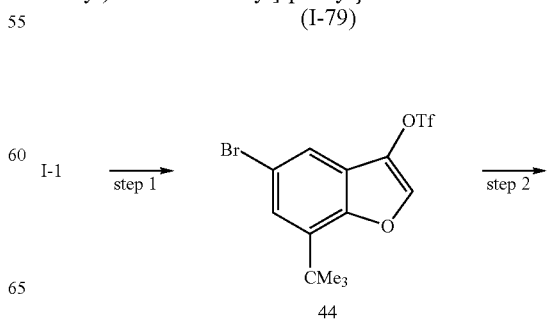

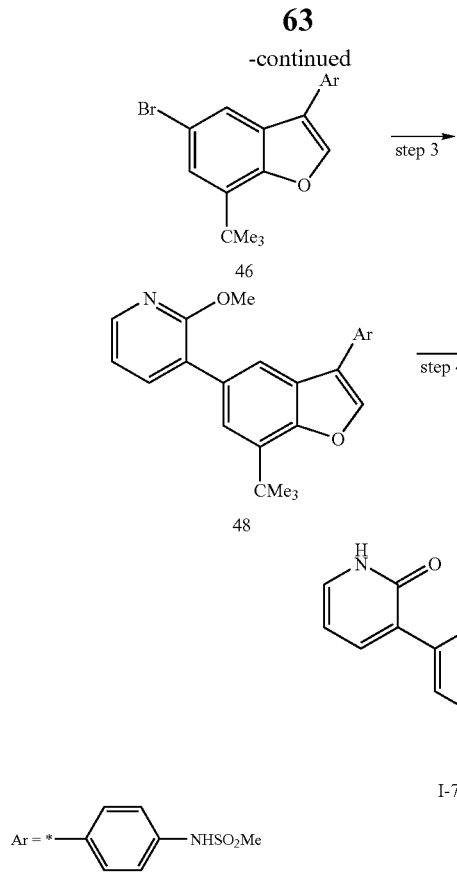

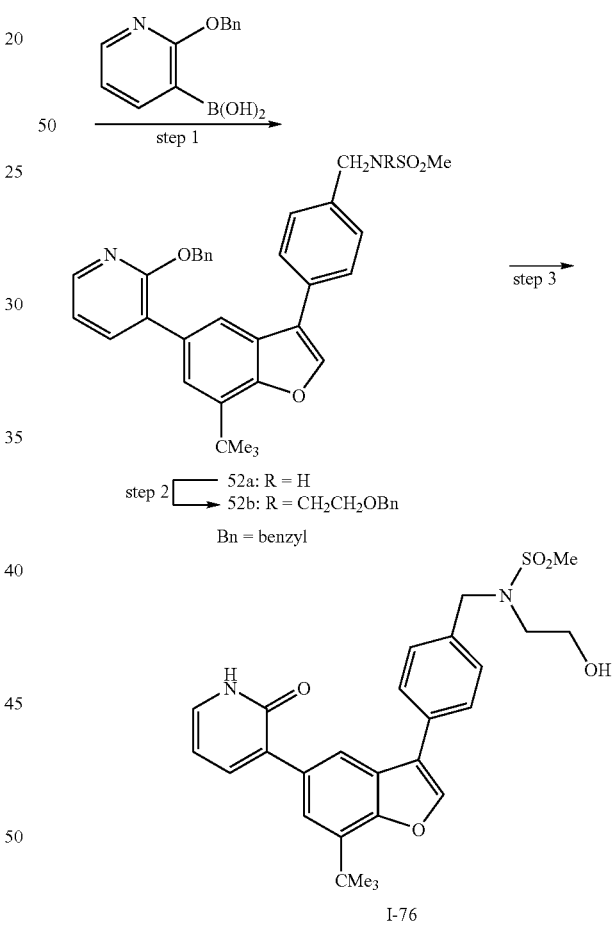

step 1—To a solution of I-1 (1.05 g, 3.9 mmol) in DCM (20 mL) cooled to −10° C. was added DIPEA (0.82 mL, 4.7 mmol). Trifluoromethanesulfonic anhydride (0.72 mL, 4.3 mmol) was added dropwise. The reaction mixture was warmed slowly to RT over 2 h then quenched with H$_2$O. The aqueous phase was extracted with DCM and the combined organic extracts were dried (MgSO$_4$), filtered and concentrated in vacuo. The residue was purified by SiO$_2$ chromatography eluting with 10% EtOAc/hexanes to afford 1.50 g (95%) of 44 as a light yellow solid.

step 2—A microwave vial was charged with 44 (100 mg, 0.25 mmol), 4-(methylsulfonylamino)phenylboronic acid (54 mg, 0.25 mmol), Pd(PPh$_3$)$_4$ (11 mg, 0.01 mmol), Na$_2$CO$_3$ (53 mg, 0.50 mmol), MeOH (2 mL), and DCM (0.5 mL). The vial was sealed and irradiated in a microwave synthesizer at 115° C. for 10 min. After cooling to RT the reaction was quenched with H$_2$O. The aqueous phase was extracted with DCM and the combined organic extracts were dried (MgSO$_4$), filtered and concentrated in vacuo. The residue was purified by SiO$_2$ chromatography eluting with an EtOAc/hexane gradient (0% to 50% EtOAc) to afford 69 mg (66%) of 46 as a pink oil.

step 3—A microwave vial was charged with 46 (170 mg, 0.40 mmol), 2-methoxy-3-pyridineboronic acid (67 mg, 0.44 mmol), Pd(PPh$_3$)$_4$ (23 mg, 0.02 mmol), Na$_2$CO$_3$ (85 mg, 0.80 mmol), MeOH (2 mL), and DCM (0.5 mL), sealed and irradiated in a microwave synthesizer at 115° C. for 20 min. After cooling to the reaction was quenched with H$_2$O. The aqueous phase was extracted with DCM and the combined organic extracts were dried (MgSO$_4$), filtered and concentrated in vacuo. The residue was purified by SiO$_2$ chromatography eluting with a EtOAc/hexane gradient (0% to 50% EtOAc) to afford 145 mg (81%) of 48 as a light yellow solid.

step 5—To a solution of 48 (145 mg, 0.32 mmol) in HOAc (3 mL) was added 48% HBr (0.10 mL, 0.96 mmol). The reaction mixture was heated to 70° C. for 3 h and 90° C. for 2 h then cooled to RT and H$_2$O was added. The resulting precipitate was filtered, rinsed with H$_2$O, and dried under high vacuum to afford 57 mg (41%) of I-79 as a beige solid.

I-86 is prepared analogously except in step 2, 4-(methylsulfonylamino)phenylboronic acid is replaced with 4-aminobenzeneboronic acid.

Example 10

N-{4-[7-tert-Butyl-5-(2-oxo-1,2-dihydro-pyridin-3-yl)-benzo furan-3-yl]-benzyl}-N-(2-hydroxy-ethyl)-methanesulfonamide (I-76)

step 1—A vial was charged with N-[4-(5-bromo-7-tert-butyl-benzofuran-3-yl)-benzyl]-methanesulfonamide (50) (160 mg, B-4, R$^2$=tert-Bu, Ar=MeSO$_2$HNC$_6$H$_4$) see example 3, step 5), 2-benzyloxy-pyridin-3-yl-boronic acid (126 mg), Pd(dppf)$_2$Cl$_2$·CH$_2$Cl$_2$ (15 mg), Na$_2$CO$_3$ (58 mg), MeOH (3 mL) and DCM (1 mL), sealed and irradiated in a microwave synthesizer to 115° C. for 1 h. The reaction mixture was concentrated and partitioned between water and EtOAc. The organic phase was separated, washed with brine, dried, filtered and concentrated. The crude product was purified by SiO$_2$ chromatography eluting with an EtOAc/hexane gradient (40 to 100% EtOAc) to afford 230 mg of 52a as an oil.

step 2—To a solution of 52a (105 mg, 0.194 mmol) and DMF (5 mL) cooled to 0° C. was added NaH (8 mg, 60% dispersion in mineral oil). The mixture was stirred for 10 min then (2-bromo-ethoxymethyl)-benzene (37 μL) was added. The reaction was warmed to RT over 1.5 h, quenched with H₂O and extracted with EtOAc. The organic extracts were washed twice with H₂O, dried and concentrated. The crude product was purified by SiO₂ chromatography eluting with an EtOAc/hexane gradient (20 to 40% EtOAc) to afford 120 mg of 52b.

step 3—A mixture of 52b (115 mg), Pd(OH)₂/C (30 mg) and EtOAc (20 mL) was stirred under 1 atm of hydrogen. The catalyst was filtered and the filtrate was concentrated to afford 58 mg of I-76 as a white solid.

I-77 is prepared in analogously except in step 2, 2-bromo-ethoxymethyl)-benzene was replaced with methyl iodide.

Example 11

N-{(S)-1-[7-tert-Butyl-5-(2-oxo-1,2-dihydro-pyridin-3-yl)-benzofuran-3-carbonyl]-pyrrolidin-3-ylmethyl}-N-methyl-methanesulfonamide (I-105)

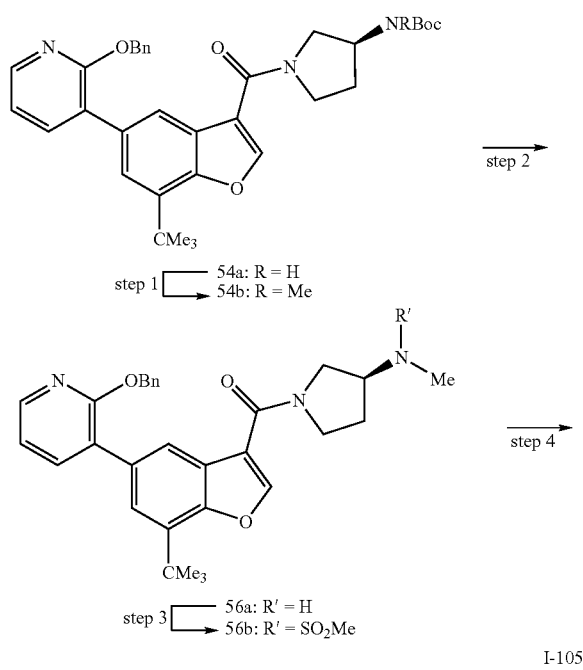

54a was prepared in accord with the procedure described for I-45 in example 1 except in step 3, 2-methoxy-3-pyridine-boronic acid was replaced with 2-benzyloxy-3-pyridine-boronic acid.

step 1—A solution of 54a (190 mg, 0.33 mmol) in DMF (3 mL) was cooled to 0° C. and NaH was added (14 mg, 0.36 mmol, 60% mineral oil dispersion). After stirring for 15 min, MeI (30 μL, 0.49 mmol) was added and the resulting solution stirred for 1 h at 0° C. The reaction was quenched with satd. aq. NH₄Cl. The resulting solution was extracted with EtOAc. The extracts were twice washed with H₂O, brine, dried (MgSO₄), filtered and concentrated to afford 194 mg of 54b as a syrup.

step 2—A solution of 54b (190 mg) and hexafluoro-isopropanol was irradiated in a microwave synthesizer at 150° C. for 1 h (35 watts). The reaction mixture was concentrated to afford 103 mg of 56a.

step 3—To a solution of 56a (120 mg, 0.241 mmol) in DCM (3 mL) cooled to 0° C. was added sequentially pyridine (58 μL, 0.289 mmol) and mesyl chloride (22 μL, 0.289 mmol) and the reaction stirred for 2 h at 0° C. The reaction was quenched with satd. NH₄Cl and extracted with EtOAc. The extracts were washed with 1N HCl and brine, dried, filtered and evaporated. The crude product was purified by SiO₂ chromatography eluting with 50% EtOAc/hexane to afford 118 mg of 56b.

step 4—Removal of the benzyl protecting group from 56b (40 mg) was carried out by hydrogenolysis with Pd(OH)₂ in MeOH out as described in step 3 of example 10 to afford 22.7 mg of I-105 as a white solid.

Example 12

N-{3-[7-tert-Butyl-5-(2-oxo-1,2-dihydro-pyridin-3-yl)-benzofuran-3-yl]-phenyl}-methanesulfonamide (I-82)

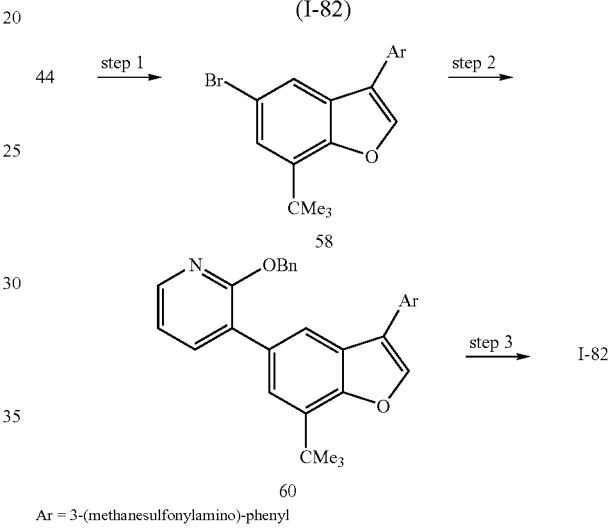

Ar = 3-(methanesulfonylamino)-phenyl step 1—A microwave vial was charged with 44 (0.2 g, 0.499 mmol, R²=CMe₃), 3-(methanylsulfonylamino)benzene boronic acid (0.107 g, 0.499 mmol), Na₂CO₃ (0.106 g, 0.997 mmol), Pd(PPh₃)₄ (0.029 g, 0.0249 mmol), MeOH (5 mL) and DCM (1.25 mL), sealed and irradiated in a microwave synthesizer at 115° C. for 10 min. The reaction mixture was cooled to RT and partitioned between DCM and H₂O. The aqueous phase was back-extracted with DCM and the combined DCM extracts were dried (MgSO₄), filtered and concentrated. The crude product was purified by SiO₂ chromatography (Analogix, 12 g) eluting with a EtOAc/hexane gradient (10 to 30% EtOAc) to afford 128 mg (62%) of 58.

step 2—A microwave vial was charged with 58 (0.168 g, 0.398 mmol, R²=CMe₃), 2-benzyloxy-pyridin-3-yl boronic acid (0.109 g, 0.427 mmol), Na₂CO₃ (0.034 g, 0.796 mmol), Pd(PPh₃)₄ (0.023 g, 0.0199 mmol), MeOH (2.4 mL) and DCM (0.6 mL). The reaction was run and worked up as in step 1. The crude product was purified by SiO₂ chromatography (Analogix, 12 g) eluting with an EtOAc/hexane gradient (10 to 30% EtOAc) to afford 176 mg (84%) of 60.

step 3—A solution of 60 (0.050 g, 0.0949 mmol), 20% Pd/C (4 mg) and MeOH (5 mL) was stirred under a hydrogen atmosphere (H₂ balloon). When the reaction was complete the reaction mixture was filtered through CELITE and the pad was rinsed with EtOAc. The filtrate was concentrated to afford 0.043 g (100%) of I-82.

Example 13

3-[7-tert-Butyl-3-(5-methyl-pyridin-2-yl)-benzofuran-5-yl]-1H-pyridin-2-one (I-91)

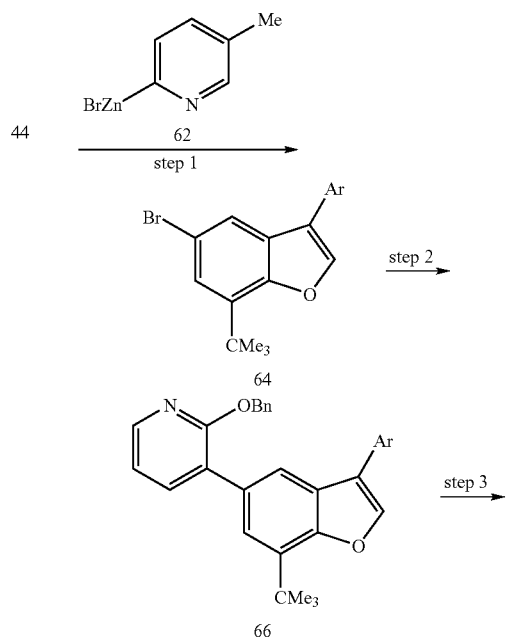

Ar = 5-methyl-pyridin-2-yl step 1—To a solution of 44 (1.0 g, 2.49 mmol), Pd(PPh₃)₄ (0.139 g, 0.12 mmol) and THF (5 mL) at RT was added 5-methyl-pyridin-2-yl zinc bromide (10 mL, 4.98 mmol, 0.5 M solution in THF). The solution was stirred at RT for 4 h. The reaction was quenched with sat'd aq. NH₄Cl and extracted with EtOAc. The EtOAc extracts were washed with brine, dried (MgSO₄), filtered and evaporated. The crude product was purified by SiO₂ chromatography eluting with an EtOAc/hexane gradient (0 to 20% EtOAc) to afford 0.471 g (55%) of 64 as a yellow solid.

Steps 2 and 3 are carried out as described in steps 2 and 3 of example 12 to afford I-91.

Example 14

N-{5-[7-tert-Butyl-5-(2-oxo-1,2-dihydro-pyridin-3-yl)-benzofuran-3-yl]-pyridin-2-ylmethyl}-methanesulfonamide (I-93)

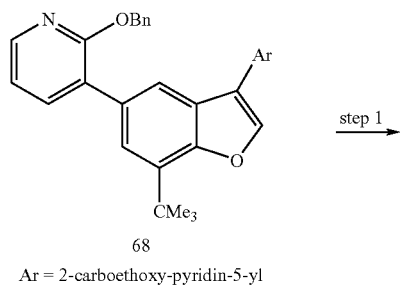

Ar = 2-carboethoxy-pyridin-5-yl

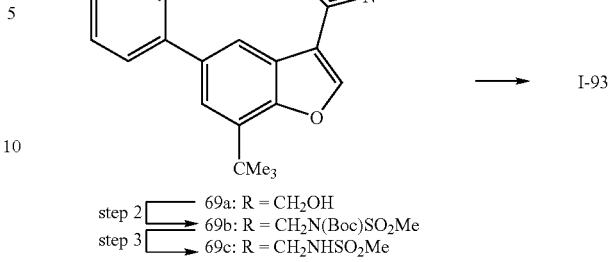

step 2 ⎡ 69a: R = CH₂OH
       ⎣→ 69b: R = CH₂N(Boc)SO₂Me
step 3 ⎣→ 69c: R = CH₂NHSO₂Me The synthesis of 68 was carried out by palladium-catalyzed coupling of 44 (R² = CMe₃) and 5-(4,4,5,5-tetramethyl-[1,3,2]dioxaborolan-2-yl)-pyridine-2-carboxylic acid methyl ester followed by a second coupling of the resulting product with 2-benzyloxy-pyridin-3-yl boronic acid. The couplings are carried out as described in steps 1 and 2 of example 12.

step 1—To a solution of 68 (0.259 g, 0.53 mmol) and THF (5 mL) cooled to 0° C. was added slowly a solution of LiAlH₄ (0.64 mL of a 1.0M THF solution) and the resulting solution was stirred at 0° C. for 30 min. The reaction was quenched with Na₂SO₄.10H₂O and the resulting slurry allowed to stand overnight. The resulting solution was filtered through a pad of CELITE which was washed with EtOAc and MeOH and the filtrate was concentrated. The crude product was purified by SiO₂ chromatography eluting with an EtOAc/hexane gradient (0 to 10% EtOAc) to afford 0.116 g (47%) of 69a as a yellow solid.

step 2—To a solution of 69a (0.116 mg, 0.25 mmol), N-(tert-butoxycarbonyl)-methanesulfonamide (0.059 g, 0.3 mmol) and THF (5 mL) was added PPh₃ (0.059 g, 0.3 mmol). The solution was cooled to 0° C. and diisopropyl azadicarboxylate was added. The solution was stirred at 0° C. for 1 h then the ice bath was removed and the solution warmed to RT. An additional equivalent of PPh₃ and diisopropyl azadicarboxylate were added and the reaction stirred for an additional 3.5 h. The solvents were evaporated and the product purified by SiO₂ chromatography eluting with an EtOAc/hexane gradient (0 to 50% EtOAc) to afford 0.284 g of material which consisted of 69b contaminated with the amine.

step 3—The crude product from step 2 was dissolved in trifluoroethanol (4 mL) and irradiated in a microwave synthesizer at 150° C. for 30 min. The reaction mixture was cooled and concentrated. The crude product was purified by SiO₂ chromatography eluting with an EtOAc/hexane gradient (0 to 100% EtOAc) to afford 0.056 g (40%) of 69c.

The final hydrogenolysis of the benzyl group is carried out as described in step 3 of example 12 to afford I-93.

Example 15

3-[3-(6-Amino-pyridin-3-yl)-7-tert-butyl-benzofuran-5-yl]-1H-pyridin-2-one (I-96)

5-[5-(2-Benzyloxy-pyridin-3-yl)-7-tert-butyl-benzofuran-3-yl]-pyridin-2-ylamine (70) is prepared by palladium-catalyzed coupling of 44 (R² = CMe₃) and 5-(4,4,5,5-tetramethyl-[1,3,2]dioxaborolan-2-yl)-pyridin-2-ylamine (CASRN 827614-64-2) and subsequent coupling of the product and 2-benzyloxy-pyridin-3-yl boronic acid as described in steps 1 and 2 of example 12.

A solution of 70 (0.75 g), 48% HBr (57 μL) and HOAc (2 mL) was stirred overnight at RT. Additional HBr (1 equivalent) was added and the reaction heated to 40° C. for 5 h. The crude product was purified by $SiO_2$ chromatography eluting with a gradient consisting of a solution of DCM/MeOH/$NH_4OH$ (90:10:0.5) and DCM (100 to 0% DCM) to afford 14 mg (23%) of I-96 as a white powder.

I-89 is prepared analogously except in the first palladium-coupling step, 5-(4,4,5,5-tetramethyl-[1,3,2]dioxaborolan-2-yl)-pyridin-2-ylamine was replaced with 5-(4,4,5,5-tetramethyl-[1,3,2]dioxaborolan-2-yl)-pyrimidin-2-ylamine (CASRN 402960-38-7).

Example 16

N-{4-[7-tert-Butyl-5-(2-oxo-1,2-dihydro-pyridin-3-yl)-benzofuran-3-yl]-3-methoxymethyl-benzyl}-methanesulfonamide (I-97)

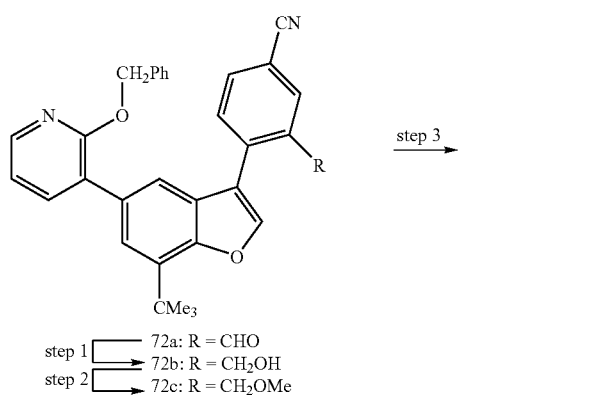

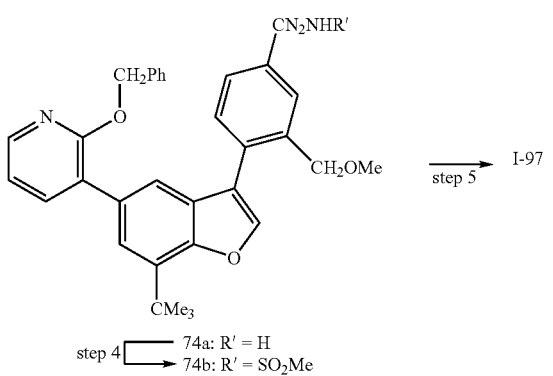

3-Formyl-4-(4,4,5,5-tetramethyl-[1,3,2]dioxaborolan-2-yl)-benzonitrile (71)—To a solution of 4-bromo-3-formyl-benzonitrile (558 mg, 2.66 mmol, CASRN 89003-95-2) in dioxane (13 mL) was added bis-(pinacolato)-diborane (0.742 g, 2.92 mmol), KOAc (0.782 g, 7.97 mmol) and Pd(II) $Cl_2$ (dppf) (0.097 g, 0.133 mmol) and the resulting solution heated at 100° C. for 17 h). The reaction was cooled to RT and diluted with water. The mixture was thrice extracted with EtOAc. The combined extracts were washed sequentially with water and brine, dried ($MgSO_4$) and evaporated. The product was purified by $SiO_2$ chromatography eluting with an EtOAc/hexane gradient (20 to 50% EtOAc) to afford 0.946 g of 71 contaminated with some borane compounds.

The synthesis of 72a was carried out by palladium-catalyzed coupling of 44 ($R^2$=$CMe_3$) and 71 followed by a second coupling of the product with 2-benzyloxy-pyridin-3-yl boronic acid. The couplings are carried out as described in steps 1 and 2 of example 12.

step 1—To a solution of 72a (0.204 g, 0.419 mmol) in MeOH (5 mL) and THF (3 mL) cooled to 0° C. was added $NaBH_4$ (0.017 g, 0.461 mmol). After stirring for 1 h at 0° C. and addition 3 mg of $NaBH_4$ was added and stirring continued for an additional 30 min. The reaction was quenched with water and extracted with EtOAc. The combined extracts were dried ($MgSO_4$), filtered and evaporated. The crude product was purified by $SiO_2$ chromatography eluting with an EtOAc/hexane gradient (0 to 30% EtOAc) to afford 0.193 g (94%) of 72b as a white foam.

step 2—To a solution of 72b (0.186 g, 0.381 mmol) and THF (5 mL) was added NaH (11 mg, 0.457 mmol, 60% mineral oil dispersion). The reaction mixture was stirred at RT for 30 min. Iodomethane (28 μL) was added dropwise and the reaction mixture stirred for 17 h at RT. Additional aliquots of NaH (15 mg) and iodomethane (24 μL) were added and the mixture stirred at 40° C. for 5 h. A third identical aliquot of both NaH and MeI were added and stirring continued overnight at 40° C. at which time 72b was consumed. The reaction mixture was cooled to RT, quenched with water and extracted with EtOAc. The combined extracts were dried ($MgSO_4$), filtered and concentrated. The crude product was purified by $SiO_2$ chromatography eluting with a EtOAc/hexane gradient (0 to 20% EtOAc) to afford 0.1914 g (19%) of 72c as a viscous oil.

step 3—To a solution of 72c (0.172 g, 0.342 mmol) in THF (3 mL) cooled to 0° C. was added dropwise a solution of $LiAlH_4$ (0.38 mL, 1.0 M solution in THF). The cooling bath was removed and the reaction allowed to stir overnight. The reaction mixture was again cooled and additional $LiAlH_4$ solution (0.34 mL) was added and the reaction stirred at RT for 6 h. The reaction was quenched by careful addition of $Na_2SO_4.10H_2O$ until gas evolution ceased. The reaction was stirred for an additional 30 min and anhydrous $Na_2SO_4$ was added. The mixture was filtered through a plug of CELITE which was washed with EtOAc. The solution was evaporated to afford 0.182 g of 74a as a viscous oil.

step 4—To a solution of 74a (0.173 g, 0.341 mmol) and DCM (2 mL) cooled to 0° C. were slowly added sequentially TEA (57 μL, 0.410 mmol) and mesyl chloride (29 μL, 0.376 mmol). The reaction mixture was stirred at 0° C. for 1.5 h. The solution is evaporated, partitioned between EtOAc and water. The combined extracts were washed, dried, filtered and evaporated. The crude product was purified by $SiO_2$ chromatography eluting with a EtOAc/hexane gradient (0 to 50% EtOAc) to afford 0.72 mg (36%) of 74b as a white foam.

The conversion of 74b to I-97 was carried out by catalytic hydrogenolysis of the benzyl group as described in step 3 of example 12.

Example 17

N-(1-{4-[7-tert-Butyl-5-(2-oxo-1,2-dihydro-pyridin-3-yl)-benzofuran-3-yl]-phenyl}-ethyl)-methanesulfonamide (I-88)

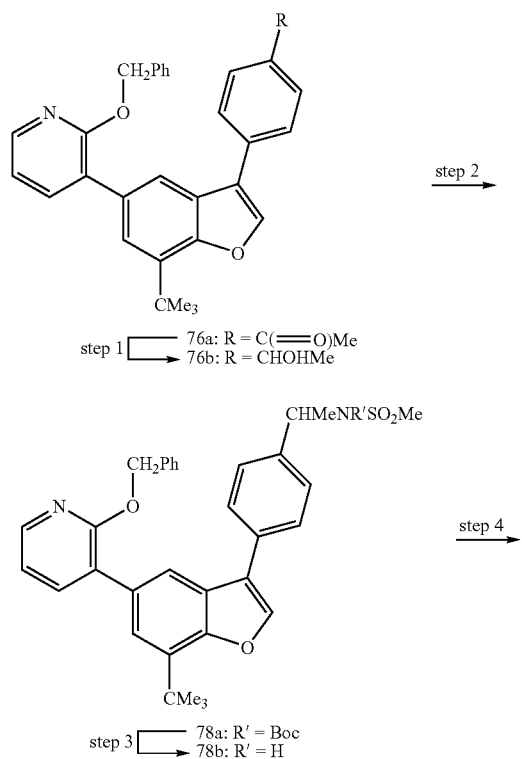

The synthesis of 76a was carried out by palladium-catalyzed coupling of 44 (R²=CMe₃) and 4-acetyl-benzeneboronic acid (CASRN 149104-90-5) followed by a second coupling of the product with 2-benzyloxy-pyridin-3-yl boronic acid. The couplings are carried out as described in steps 1 and 2 of example 12.

step 1—To a solution of 76a (0.566 g, 1.19 mmol) in MeOH (10 mL) and THF (5 mL) at RT was added NaBH₄ (0.050 g, 1.31 mmol). The reaction was stirred at RT for 30 min then quenched with water and extracted with EtOAc. The combined extracts were dried (MgSO₄), filtered and evaporated to afford 0.572 g of 76b as a white foam.

step 2—To a solution of 76b (0.200 g, 0.42 mmol) and THF (4 mL) was added N-(tert-butoxycarbonyl)-methanesulfonamide (0.123 g, 0.63 mmol) and PPh₃ (0.165 g, 0.63 mmol). The resulting solution was cooled to 0° C. and DEAD (100 μL, 0.63 mmol) was added dropwise. The reaction was stirred for 1 h at 0° C. the overnight at RT. The solvents were evaporated and the crude product purified by SiO₂ chromatography eluting with an EtOAc/hexane gradient (10 to 20% EtOAc) to afford 0.152 g (55%) of 78a as a white foam.

step 3—To a solution of 78a (0.150 g, 0.23 mmol) and DCM (8 mL) was added TFA (1 mL) and the resulting solution stirred at RT for 2 h. The volatile solvents were evaporated and the residue dissolved in DCM and sequentially washed with 0.5M NaOH and water. The organic phase was dried (MgSO₄), filtered and evaporated. The crude product was purified by SiO₂ chromatography eluting with an EtOAc/hexane gradient (10 to 40% EtOAc) to afford 67 mg (53%) of 78b as a white foam.

The conversion of 78b to I-88 was carried out by catalytic hydrogenolysis of the benzyl group as described in step 3 of example 12

Example 18

N-{(S)-1-[7-tert-Butyl-1-methyl-5-(2-oxo-1,2-dihydro-pyridin-3-yl)-1H-indole-3-carbonyl]-pyrrolidin-3-ylmethyl}-methanesulfonamide (I-111)

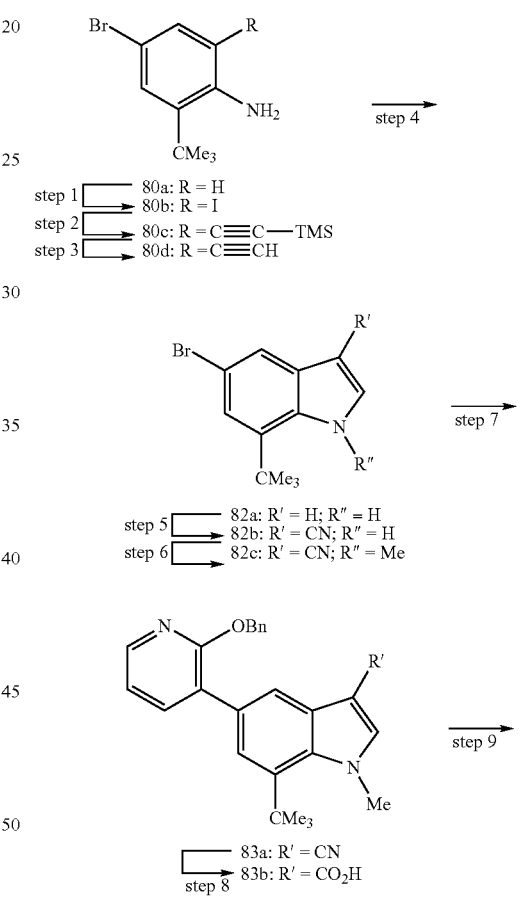

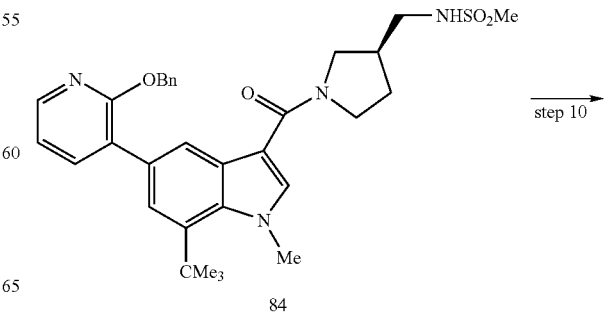

84

-continued

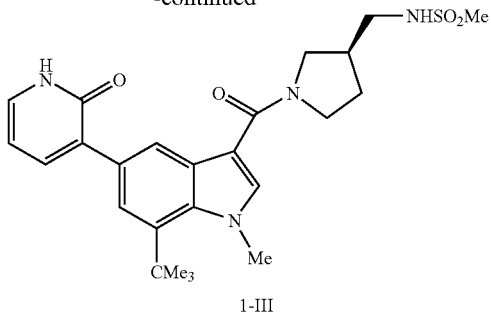

I-III step 1—To a solution of 80a (12.0 g, 52.6 mmol, CASRN 850012-44-1) in EtOH (150 mL) was added iodine (14.7 g, 57.8 mmol). When the iodine dissolved Ag$_2$SO$_4$ (18.0 g, 57.8 mmol) was added and the reaction stirred for 1.5 h at RT. The solid silver salts were removed by filtration and washed with EtOH. The filtrate was concentrated and redissolved in DCM, washed sequentially with 10% aq. Na$_2$S$_2$O$_3$ and water, dried (MgSO$_4$), filtered and concentrated. The crude product was purified by SiO$_2$ chromatography eluting with a DCM/hexane gradient (0 to 20% DCM) to afford 10.3 g (55%) of 80b.

step 2—To a solution of 80b (10.3 g, 29.0 mmol) in THF (100 mL) was added TEA (12.1 mL), trimethylsilylacetylene (4.9 mL, 34.8 mmol), Pd(PPh$_3$)$_2$Cl$_2$ (0.350 g, 0.5 mmol) and CuI (0.095 g, 0.5 mmol). The reaction was stirred at RT overnight, then quenched with water and extracted with EtOAc. The combined extracts were dried (MgSO$_4$), filtered and evaporated. The residue was purified by SiO$_2$ chromatography eluting with a DCM/hexane gradient (0 to 10% DCM) to afford 13.7 g of 80c as a maroon oil.

step 3—To a solution of 80c (9.4 g, 29.0 mmol) in THF (60 mL) was added tetrabutylammonium fluoride (29 mL, 1.0M solution in THF). The reaction was stirred for 30 min at RT then quenched with water and extracted with EtOAc. The combined extracts were dried (MgSO$_4$), filtered and evaporated. The residue was purified by SiO$_2$ chromatography eluting with a DCM/hexane gradient (0 to 20% DCM) to afford 4.38 g (60%) of pure 80d.

step 4—To a solution of 80d (4.38 g, 17.3 mmol) in EtOH (60 mL) was added NaAuCl$_4$.2H$_2$O (0.199 g, 0.5 mmol). The reaction was stirred overnight at RT, concentrated and directly added to a SiO$_2$ column and diluted with an EtOAc/hexane gradient (10 to 20% EtOAc) to afford 3.53 g (81%) of 82a as a light brown solid.

step 5—To a solution of 82a (1.00 g, 3.96 mmol) and MeCN (20 mL) cooled to 0° C. was added dropwise over 5 min chlorosulfonyl isocyanate (0.35 mL, 3.96 mmol). The reaction was stirred at 0° C. for 30 min then DMF (0.33 mL, 4.35 mmol) was added dropwise. Stirring was continued at 0° C. for another 30 min then warmed to RT and stirred for an additional 2 h. The reaction was quenched by addition of water and the resulting solution extracted with EtOAc. The combined extracts were dried (MgSO$_4$), filtered and evaporated. The residue was purified by SiO$_2$ chromatography eluting with an EtOAc/hexane gradient (30 to 50% EtOAc) to afford 0.560 g (51%) of pure 82b.

step 6—To a solution of 82b (0.560 g, 2.02 mmol) and DMF (10 mL) cooled to 0° C. was added NaH (0.090 g, 2.22 mmol, 60% dispersion in mineral; oil). The reaction mixture was warmed to RT and stirred for 45 min. To the solution was added iodomethane (0.15 mL, 2.42 mmol) and the resulting solution stirred overnight. The reaction was quenched with water (ca. 30 mL). The resulting precipitate was filtered, rinsed with water and dried under vacuum to afford 590 mg of 82c.

step 7—Palladium-catalyzed coupling of 82c and 2-benzyloxy-pyridin-3-yl boronic acid to afford 83a is carried out in accord with the procedure described in step 2 of example 12.

step 8—To a suspension of 83a (0.530 g, 1.34 mmol) in water was added NaOH (20 equivalents) and the mixture heated to 100° C. the reactant failed to dissolve and some dioxane and EtOH were added which resulted in a biphasic reaction mixture which was heated overnight. The reaction mixture was cooled, acidified and extracted with EtOAc. The combined extracts were dried (MgSO$_4$), filtered and concentrated. The residue was purified by SiO$_2$ chromatography eluting with an EtOAc/hexane gradient (50 to 100% EtOAc) to afford 0.143 g (26%) of 83b a separate fraction containing 335 mg of the corresponding amide.

step 9—To a solution of 82b (0.135 g 0.32 mmol) and DMF (3 mL) was added N-(S)-1-pyrrolidin-3-ylmethyl-methanesulfonamide TFA salt (0.102 g, 0.35 mmol) [prepared from (R)-3-aminomethyl-pyrrolidine-1-carboxylic acid tert-butyl ester as in example 1], EDCI (0.067 g, 0.35 mmol) and HOBt (0.047 g, 0.35 mmol) followed by DIPEA (0.14 mL, 0.80 mmol). The reaction was stirred overnight at RT, quenched with water and the mixture thrice extracted with EtOAc. The combined extracts were thrice washed with water, dried (MgSO$_4$), filtered and evaporated. The product was purified by SiO$_2$ chromatography eluting with a MeOH/EtOAc gradient (0 to 10% MeOH) to afford 0.075 g (41%) of 84.

The conversion of 84b to I-111 was carried out by catalytic hydrogenolysis of the benzyl group as described in step 3 of example 12.

I-110 was prepared from 82a by catalytic hydrogenolysis of the benzyl group as described in step 3 of example 12.

Example 19

3-(7-tert-Butyl-1-methyl-1H-indol-5-yl)-1H-pyridin-2-one

The title compound is prepared in accord with the procedures in example 18 starting from 5-bromo-7-tert-butyl-1-methyl-1H-indole introducing the 2-benzyloxy-pyridin-3-yl radical by palladium-catalyzed coupling and catalytic hydrogenolysis of the benzyl radical.

5-bromo-7-tert-butyl-1-methyl-1H-indole—To a solution of 82a and DMF (3.0 mL) was added NaH (0.024 g, 60% mineral oil dispersion) and the resulting solution stirred at RT for 15 min. To this solution was added dropwise a iodomethane (0.04 mL). The reaction was stirred for 1.25 h at RT. The reaction was quenched with water and twice extracted with Et$_2$O. The combined extracts were washed with water, dried (Na$_2$SO$_4$), filtered and concentrated. The crude product was purified by SiO$_2$ chromatography eluting with a EtOAc/hexane gradient (0 to 5% EtOAc) to afford 0.560 g (51%) of the title compound.

Example 20

N-{1-[5-Bromo-7-(1-methyl-cyclopropyl)-benzofuran-3-carbonyl]-pyrrolidin-3-ylmethyl}-methanesulfonamide (92)

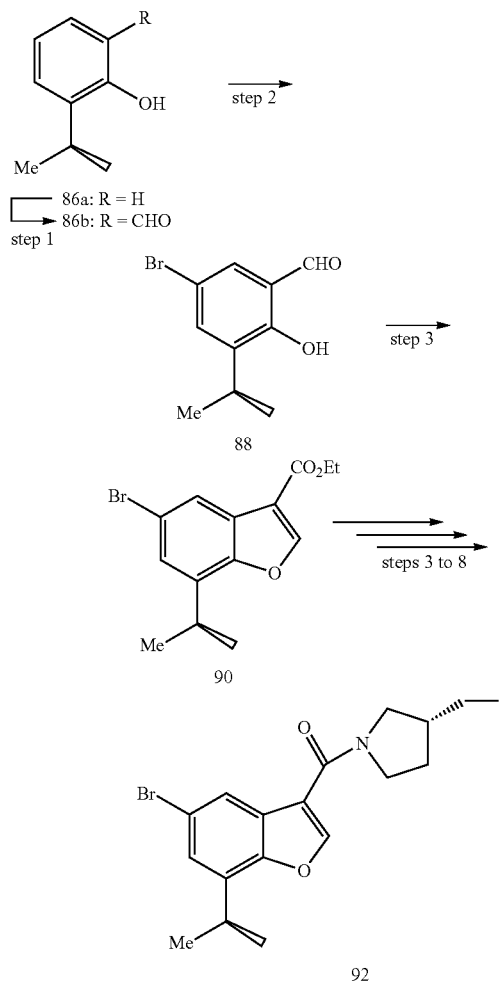

step 1—To a solution of 2-(1-methylcyclopropyl)phenol (86a, 0.55 g, 3.4 mmol; CASRN 433684-77-6) in MeCN (7 mL) was added paraformaldehyde (0.68 g, 23 mmol), $MgCl_2$ (0.48 g, 0.051 mmol) and TEA (1.3 g, 13 mmol). The mixture was stirred and heated at reflux for 5 h. After cooling to RT, the reaction mixture was partitioned between DCM and 1M aqueous HCl, and the organic extracts were dried ($Na_2SO_4$), filtered and concentrated. The crude residue was purified by $SiO_2$ chromatography eluting with EtOAc/hexane to afford 0.34 g (58%) of 2-hydroxy-3-(1-methylcyclopropyl)-benzaldehyde (86b) as a light yellow oil.

step 2: To a solution 86b (0.34 g, 1.9 mmol) in DCM-MeOH (3:2, 20 mL) was added tetrabutylammonium tribromide (0.98 g, 2.0 mmol), and the resulting mixture was stirred at RT for 75 min. The solvent was removed under reduced pressure, and residue was partitioned between EtOAc and water. The EtOAc layer was washed sequentially with water and brine, dried ($Na_2SO_4$), filtered and concentrated. The crude residue was purified by $SiO_2$ chromatography eluting with EtOAc/hexane to afford 0.45 g (91%) of 5-bromo-2-hydroxy-3-(1-methylcyclopropyl)benzaldehyde (88) as a light yellow solid.

The salicyladehyde derivative 88 is converted to 90 with ethyl diazoacetate and fluoroboric acid etherate as described in step 2 of example 1. The ethyl ester 90 is converted to 92 according to the procedures described in steps 3 to 8 of example 1.

Example 21

N-{4-[7-tert-Butyl-5-(3-oxo-3,4-dihydro-pyrazin-2-yl)-benzofuran-3-carbonyl]-morpholin-2-ylmethyl}-methanesulfonamide (100)

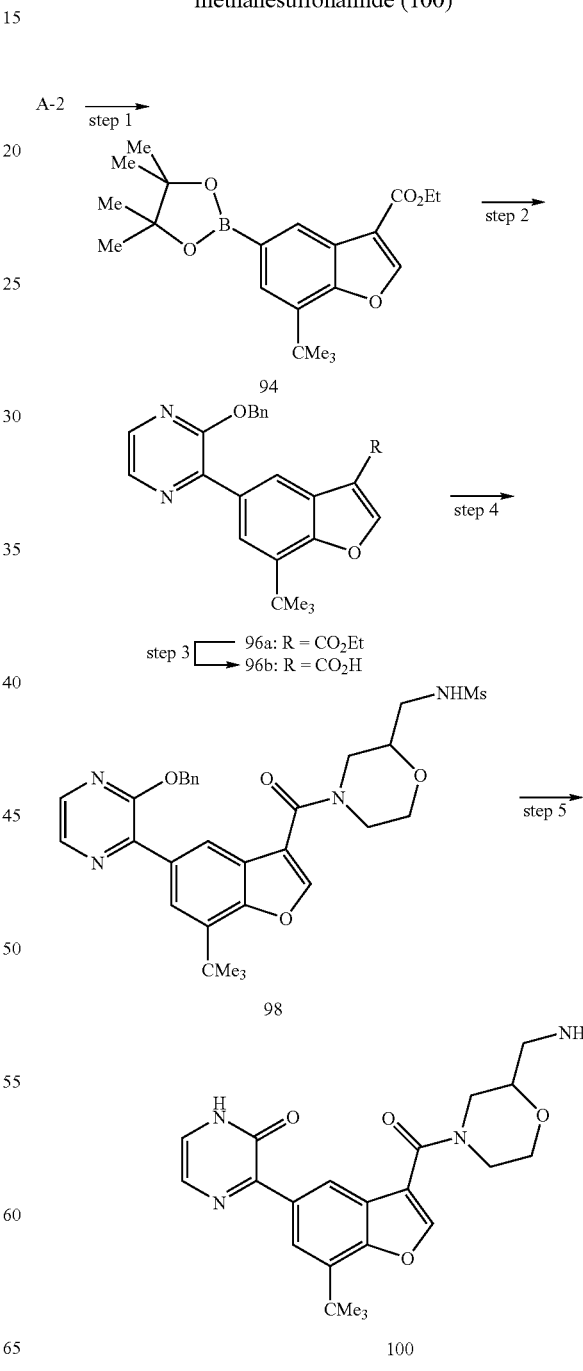

2-benzyloxy-3-chloropyrazine (95)—To a solution of 2,3-dichloro-pyrazine (50.0 g, 0.335 mol), benzyl alcohol (39.9 g) and THF (250 mL) was added solid KOH. A slow exotherm occurred which raised the temperature to around 40° C. The reaction was maintained at 40-45° C. until the reaction was complete. The salts were washed with water, the THF evaporated and 95 purified by simple distillation.

step 1—A flask was charged with A-2b ($R^2$=tert-Bu, 1.00 g, 3.07 mmol), bis-(pinacolato)diboron (0.820 g, 3.22 mmol, CASRN 73183-34-3), Pd(dppf)$Cl_2$.$CH_2Cl_2$ (0.0074 g, 0.09 mmol), dppf (0.050 g, 0.09 mmol), KOAc (0.900 g, 9.20 mmol) and dioxane (20 mL) heated at 80° C. for 72 h. The reaction mixture was cooled to RT and quenched with $H_2O$. The resulting solution was extracted with EtOAc and the combined extracts dried ($MgSO_4$), filtered and concentrated in vacuo. The crude product was purified by $SiO_2$ chromatography (80 g Analogix column) eluting with 10% EtOAc/hexane to afford 0.510 g (45%) of 94 as a yellow solid.

step 2—A microwave vial was charged with 95 (0.251 g, 1.14 mmol), 94 (0.509 g, 1.37 mmol), Pd(PPh$_3$)$_4$ (66 mg, 0.057 mmol), $Na_2CO_3$ (0.242 g, 2.28 mmol), MeOH (6 mL) and DCM (1.5 mmol), sealed and irradiated in a microwave reactor at 115° C. for 40 min. The reaction was incomplete and additional aliquots of 95 (50 mg) and Pd(PPh$_3$)$_4$ (20 mg) were added, the vial resealed and irradiated at 115° C. for another 20 min. The reaction mixture was cooled to RT, diluted with DCM and $CHCl_3$ and the organic solution washed with $H_2O$ and brine. The aqueous phase was back extracted with DCM and the combined organic extracts dried ($MgSO_4$), filtered and evaporated. The crude product was purified by $SiO_2$ chromatography (Analogix, 40 g) eluting with an EtOAc/hexane gradient (0 to 20% EtOAc) to afford 0.384 g of 94 as a mixture of methyl and ethyl esters.

Step 3 was carried out in accord with the procedure described in step 5 of example 1 except the base was NaOH in place of LiOH and the solvent was aqueous EtOH. Step 4 was carried out in accord with the procedure in step 8 of example 1 except 22 is replaced with N-(2-morpholinylmethyl)-methanesulfonamide (CASRN 1153762-77-6 which is available from commercial sources or is readily prepared by sulfonylation and deprotection of 2-aminomethylmorpholine-4-carboxylic acid tert-butyl ester, CASRN 140645-53-0) utilizing procedures analogous to those described herein step 5—A mixture of 98 (0.101 g), moist 20% Pd/C (10 mg) and MeOH at RT was stirred under a hydrogen atmosphere maintained with a hydrogen-filled balloon. The reaction mixture was filtered through a pad of CELITE and rinsed with DCM/MeOH and the filtrated was concentrated and purified by $SiO_2$ chromatography eluting with a MeOH/DCM (containing 0.5% $NH_4OH$ gradient (0 to 5% MeOH) to afford 58 mg (68%) of 100 as a yellow solid: MS (M+H)$^+$=489; $IC_{50}$ NS5B Polymerase=28 nM.

N-{1-[7-tert-Butyl-5-(3-oxo-3,4-dihydro-pyrazin-2-yl)-benzofuran-3-carbonyl]-piperidin-3-ylmethyl}-methanesulfonamide (102) (MS: (M+H)$^+$=487; mp 172.0-174.0° C.; $IC_{50}$ NS5B Polymerase=8.0 nM) as prepared analogously except in step 4, N-(2-morpholinylmethyl)-methanesulfonamide was replaced with N-(3-piperidinylmethyl)-methanesulfonamide (CASRN 86504-28-5) which can be prepared from 3-(aminomethyl)-N-Boc-piperidine (CASRN 162167-97-7) by sulfonylation and deprotection utilizing procedures analogous to those described herein.

Example 22

N-{4-[7-tert-Butyl-5-(2-oxo-1,2-dihydro-pyridin-3-yl)-benzo[b]thiophene-3-carbonyl]-morpholin-2-ylmethyl}-methanesulfonamide (112)

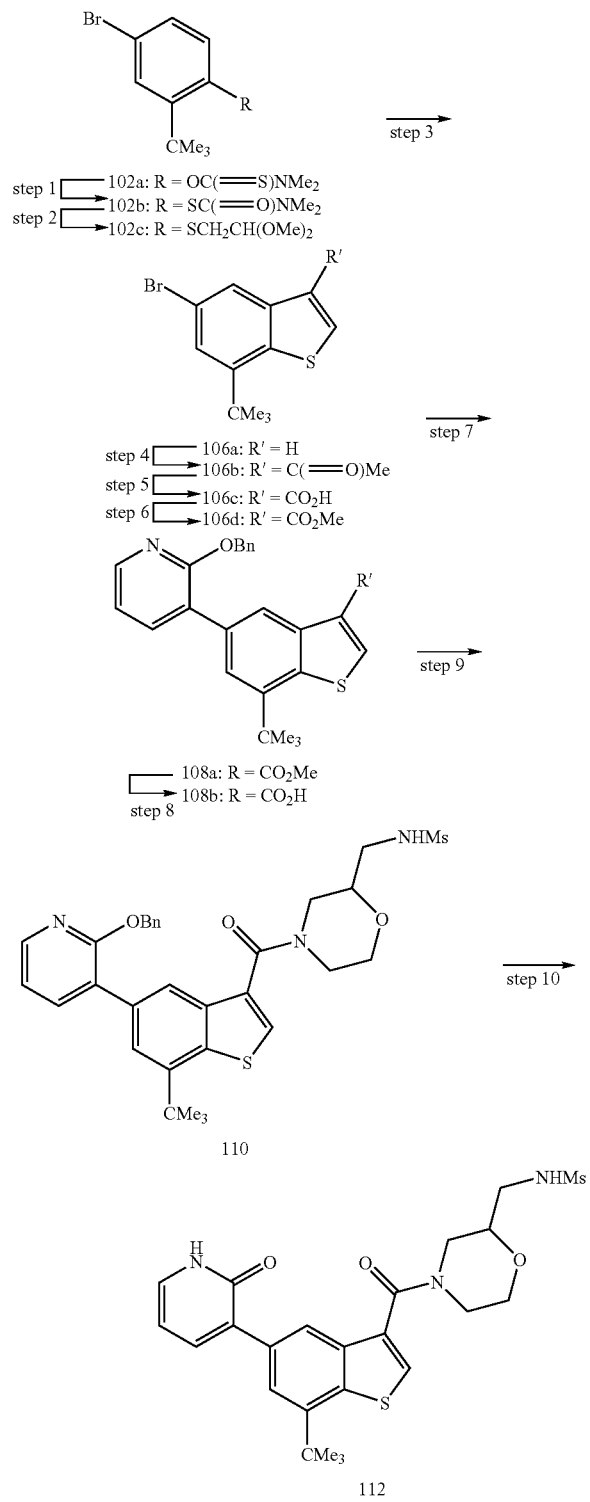

step 1—The neat thiocarbamate 102a (9.2 g, prepared by acylation of 2-tert-butyl-4-bromo-phenol with N,N-dimethyl thiocarbamoyl chloride) was heated with a heat gun for 20 min. (At 20 min extraneous peaks began to be detectable by TLC). The reactant was cooled and purified by SiO$_2$ chromatography (Analogix, 80 g) eluting with an EtOAc/hexane gradient to afford 4.6 g (50%) of 102b as a light brown solid.

step 2—To a solution of 102b (4.6 g, 14.5 mmol) in MeOH (30 mL) was added KOH (1.3 g, 21.8 mmol) and the reaction mixture was heated at 65° C. overnight. Hydrolysis of the thiocarbamate was complete and bromoacetaldehyde dimethylacetal (1.9 mL, 16.0 mmol) was slowly added and heating continued for 3 h. The reaction was cooled to RT and the solvent evaporated. The residue was dissolved in H2O and thrice extracted with Et$_{20}$. The combined extracts were dried (MgSO$_4$), filtered and evaporated. The crude product was purified by SiO2 chromatography (Analogix, 80 g) eluting with 10% EtOAc/hexane to afford 3.28 g (68%) of 102c as a brown oil.

step 3—A 250 mL round-bottom flask was charged with polyphosphoric acid (15 g) and chlorobenzene (30 mL) and heated to 100° C. with vigorous stirring to produce a biphasic mixture. To this solution was added a solution of 102c (3.25 g, 9.75 mmol) and chlorobenzene (10 mL). The resulting brown solution was heated at 130° C. for 2 h then cooled to RT. The upper chlorobenzene layer was removed by pipette and the dark PPA residue was rinsed with toluene and the toluene removed by pipette. The combined aromatic solutions were concentrated and the residue purified by SiO$_2$ chromatography eluting with an EtOAc/hexane gradient (5 to 10% EtOAc) to afford 1.82 g (69%) of 106a as an orange oil.

step 4—To a solution of 106a (1.80 g, 6.7 mmol) and DCE (20 mL) cooled to 0° C. was added acetyl chloride (0.57 mL, 8.0 mmol) followed by SnCl4 (0.94 mL, 1.0 M DCM solution). The resulting solution was stirred overnight at RT. The reaction mixture was poured onto ice/water and extracted with DCM. The combined extracts were washed with sat'd. aq. NaHCO$_3$ and the aqueous extracts back-extracted with DCM. The combined organic extracts were dried (MgSO$_4$), filtered and concentrated in vacuo. The crude product was purified by SiO$_2$ chromatography (Analogix, 40 g) eluting with an EtOAc/hexane gradient (5 to 30% EtOAc) to afford 0.395 g (38%) of 106b as a beige solid.

step 5—To a solution of NaOH (0.870 g) and H$_2$O (10 mL) cooled to 0° C. was added dropwise Br2 (0.45 mL, 8.75 mmol). To the resulting homogeneous yellow solution was added slowly a solution of 106b (0.780 g, 2.50 mmol) and dioxane (15 mL). The resulting solution was allowed to warm to RT and stirred for 2 h. The reaction was quenched with solid NaHSO$_3$ (ca. 300 mg) then acidified with 1.0 M HCl. The resulting precipitate was filtered, washed with water and dried under high vacuum to afford 0.711 g (91%) of 106c as a beige solid.

step 6—To a suspension of 106c (700 mg, 2.23 mmol) suspended in MeOH was added slowly con. H$_2$SO$_4$ and the resulting mixture heated at 80° C. for 8 h then cooled to RT and stirred overnight. The solution was concentrated in vacuo and the solid dissolved in DCM and washed with 1.0 M NaOH. The organic phase was dried (MgSO$_4$), filtered and evaporated to afford 662 mg (91%) of 106d as a brown solid.

step 7—Palladium catalyzed coupling of 106d and 2-benzyloxy-pyridin-3-yl boronic acid was carried out in accord with the procedure in step 2 of example 12 to afford 108a.

step 8—Hydrolysis of the ester was carried out with NaOH in EtOH in accord with step 3 of example 21 to afford 108b.

step 9—To a solution of the HCl salt of N-morpholin-2-ylmethyl-methanesulfonamide (0.067 g, 0.29 mmol), 108b (0.100 g, 0.24 mmol), EDCI (0.050 g, 0.26 mmol), HOBt (0.035 g, 0.26 mmol) and DMF (3 mL) was added DIPEA (0.11 mL, 0.60 mmol) and the resulting solution stirred overnight at RT. The reaction was quenched with H$_2$O and extracted with EtOAc. The organic extract was thrice washed with H$_2$O then brine, dried (MgSO$_4$), filtered and concentrated in vacuo. The crude product was purified by SiO$_2$ chromatography (Analogix, 8 g) eluting with an EtOAc/hexane gradient (30 to 100% EtOAc) to afford 122 mg (86%) of 110 as a white foam.

step 10—Hydrogenolysis of the benzyl ether of 110 was carried out in accord with step 5 of example 21 to afford 112: MS (M+H)+=504; mp 175.0-177.0° C.; IC50 NS5B Polymerase=4 nM.

N-{1-[7-tert-Butyl-5-(2-oxo-1,2-dihydro-pyridin-3-yl)-benzo[b]thiophene-3-carbonyl]-piperidin-3-ylmethyl}-methanesulfonamide (114) was prepared analogously except in step 9, N N-morpholin-2-ylmethyl-methanesulfonamide was replaced with N-piperidin-3-ylmethyl-methanesulfonamide to afford 114: mp 175.0-177.0; IC$_{50}$ NS5B Polymerase=3 nM.

N-{(R)-1-[7-tert-Butyl-5-(2-oxo-1,2-dihydro-pyridin-3-yl)-benzo[b]thiophene-3-carbonyl]-pyrrolidin-2-ylmethyl}-methanesulfonamide (116) was prepared analogously except in step 9, N N-morpholin-2-ylmethyl-methanesulfonamide was replaced with N-(R)-1-pyrrolidin-2-ylmethyl-methanesulfonamide to afford 114: mp 289.0-291.0; 1050 NS5B Polymerase=4 nM.

Example 23

N-{1-[7-tert-Butyl-5-(2-oxo-1,2-dihydro-pyridin-3-yl)-benzofuran-3-carbonyl]-3-fluoro-piperidin-3-ylmethyl}-methanesulfonamide (124)

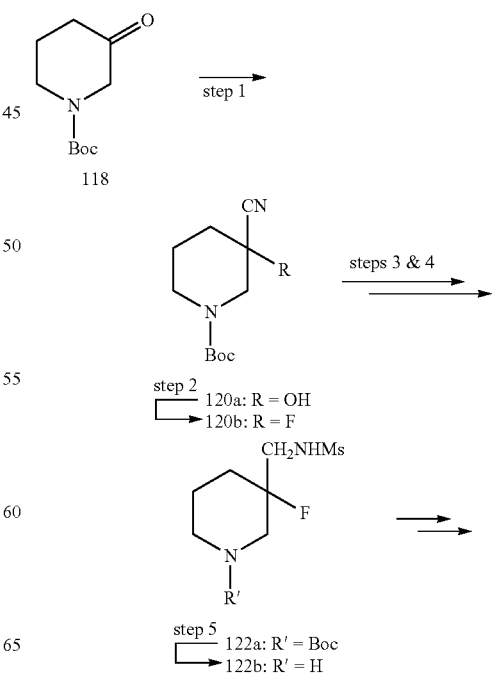

-continued

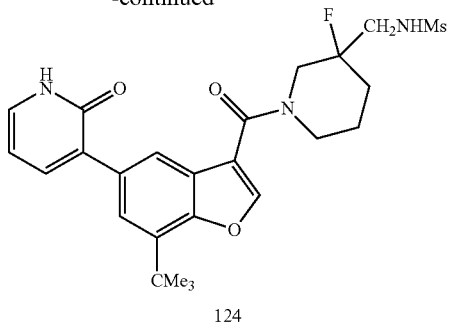

124 step 1—To a solution of N-Boc-3-piperidone (1.6 g, 8.0 mmol) and THF (5 mL) was added KCN (0.745 g, 12.0 mmol) and H₂O (10 mL) and the resulting solution was cooled to 0° C. To the resulting homogeneous orange solution was added a solution of NaHSO₃ (1.25 g) and H₂O (10 mL). The resulting solution was stirred at 0° C. for 1 h. The solution was twice extracted DCM and the combined extracts were dried (MgSO₄), filtered and evaporated to afford 1.80 g of 120a as an orange solid.

step 2—To a solution of 120a (1.8 g, 8.0 mol) and DCM (20 mL) cooled to −78° C. was added dropwise DAST (1.16 mL, 8.8 mmol) and the resulting solution stirred at −78° C. for 1 h. The reaction was warmed to 0° C. and stirred for an additional 1 h. The reaction mixture was diluted with DCM and quenched with sat'd. aq. NaHCO₃. The combined extracts were dried (MgSO₄), filtered and concentrated in vacuo. The crude product was purified by SiO₂ chromatography eluting with an EtOAc/hexane gradient (10 to 20% EtOAc) to afford 1.25 g (69%) of 120b as a pale yellow oil.

steps 3 & 4—To a solution of 120b (0.480 g, 2.1 mmol) in THF (10 mL) cooled to 0° C. was added LiAlH₄ (2.3 mL, 2.3 mmol, 1.0 M in THF). The reaction was stirred at 0° C. for 1 hr then at RT for 3 h. The reaction was quenched with Na₂SO₄.10H₂O and the resulting mixture stirred vigorously for 30 min. The solid was filtered and the filtrate rinse with EtOAc. The filtrate was concentrated to afford a 0.420 g of a pale yellow oil. The residue was in DCM (10 ml) and the solution was cooled to 0° C. To the solution was added sequentially TEA (0.370 mL, 2.7 mmol) and methanesulfonyl chloride (0.18 mL, 2.3 mmol) and the solution stirred at 0° C. for 1 h. The reaction was quenched with H₂O and extracted with DCM. The combined extracts were dried (MgSO₄), filtered and concentrated in vacuo. The residue was purified by SiO₂ chromatography (Analogix, 24 g) eluting with an EtOAc/hexane (20 to 50% EtOAc) to afford 0.220 g (34%) of 122a as a white foam.

step 5—A solution of 122a (0.220 g, 0.770 mmol) and 1.0 M HCl in MeOH (generated by addition of AcCl to MeOH) and the resulting solution stirred at 50° C. for 1 h. the reaction mixture was cooled to RT and concentrated in vacuo to afford 160 mg (92%) of 122b as a hygroscopic white foam.

The conversion of 122b to the title compound was carried out in accord with the procedure described in steps 9 and 10 of example 22. The crude product from step 9 was purified by SiO₂ chromatography eluting with an EtOAc/hexane gradient (30 to 100% EtOAc). Hydrogenolysis of the benzyl ether afforded 124:mp 180.0–182.0; IC₅₀ NS5B Polymerase=6 nM.

Example 24

3-{7-tert-Butyl-3-[3-(2-methanesulfonyl-ethyl)-piperidine-1-carbonyl]-benzo furan-5-yl}-1H-pyridin-2-one (132)

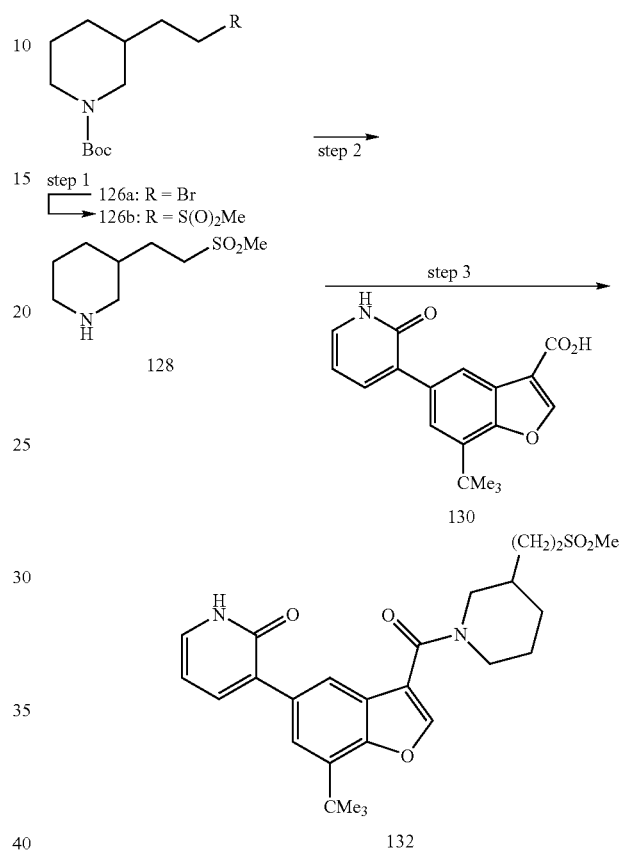

step 1—A tube was charged with 126a (0.540 g, 1.85 mmol, CASRN 210564-54-8) and methanesulfinic acid sodium salt (0.283 g 2.77 mmol), sealed and irradiated in a microwave reactor at 120° C. for 801 min. The reaction mixture was cooled to RT and diluted with EtOAc. The solution was thrice washed with H₂O, brine, dried, filtered and concentrated in vacuo to afford 0.439 g of 126b as an oil.

step 2—To a solution of 126b (0.430 g, 1.48 mmol) and HCl in dioxane (1.11 mL, 4.43 mL, 1.0 M in dioxane was stirred at RT for 7 h. The white precipitate was filtered, rinsed with Et₂O and dried to afford 0.273 g of the HCL salt of 128.

step 3—Condensation of 128 and 130 was carried out in accord with the procedure described in step 9 of example 22 except DIPEA was replaced with TEA to afford 132 which was purified by preparative SiO₂ chromatography: MS (M+H)⁺=485;

mp 145.0–147.0; IC₅₀ NS5B Polymerase=29 nM.

Example 25

HCV NS5B RNA Polymerase Activity

The enzymatic activity of HCV polymerase (NS5B570n-Con1) was measured as the incorporation of radiolabeled nucleotide monophosphates into acid insoluble RNA products. Unincorporated radiolabeled substrate was removed by filtration and scintillant was added to the washed and dried filter plate containing radiolabeled RNA product. The amount of RNA product generated by NS5B570n-Con1 at the end of the reaction was directly proportional to the amount of light emitted by the scintillant.

The HCV polymerase used in the enzymatic activity assay is a 21 amino acid C-terminal deletion of full-length HCV polymerase derived from HCV Con1 strain, genotype 1b (GenBank accession number AJ242654) (NS5B570n-Con1). The NS5B570n-Con1 was sub-cloned downstream to the T7 promoter of the plasmid expression construct pET17b and transformed into *E. coli* strain BL21(DE3) pLysS for protein expression. A single colony was used to start an innoculum for a 10 L culture in LB media supplemented with 100 µg/mL ampicillin at 37° C. Protein expression was induced by the addition of 0.25 mM isopropyl-β-D-thiogalactopyranoside (IPTG) when the optical density of the culture at 600 nM was 0.8. Induction of protein expression was carried out at 30° C. for 16 h after which the cells were harvested by centrifugation. NS5B570n-Con1 was purified to homogeneity using a three-column purification protocol including subsequent column chromatography on Ni-NTA, SP-Sepharose HP and Superdex 75 resins.

Enzymatic reactions in the presence of cIRES RNA template (see section [0300]) contained 20 nM cIRES RNA, 20 nM NS5B570n-Con1 enzyme, 0.5 µCi of tritiated UTP (Perkin Elmer catalog no. TRK-412; specific activity: 30 to 60 Ci/mmol), 1 µM each ATP, CTP, and GTP, 40 mM Tris-HCl pH 8.0, 40 mM NaCl, 4 mM DTT (dithiothreitol), 4 mM MgCl$_2$, 5 µl of compound serial diluted in DMSO, and nuclease-free water to a final reaction volume of 50 µl. Enzymatic reactions in the presence of 20 nM cIRES template, 20 nM NS5B570n-Con1 enzyme, 1 µCi of tritiated UTP (Perkin Elmer catalog no. TRK-412; specific activity: 30 to 60 Ci/mmol), 40 mM Tris-HCl pH 8.0, 40 mM NaCl, 4 mM DTT (dithiothreitol), 4 mM MgCl2, 5 µl of compound serial diluted in DMSO, and nuclease-free water to a final reaction volume of 50 µl. Reaction mixtures were assembled in 96-well filter plates (cat #MADVNOB, Millipore Co.) and incubated for 2 h at 30° C. Reactions were stopped by addition of 10% final (v/v) trichloroacetic acid and incubated for 40 min at 4° C. Reactions were filtered, washed with 8 reaction volumes of 10% (v/v) trichloroacetic acid, 2 reaction volumes of 70% (v/v) ethanol, air dried, and 25 µl of scintillant (Microscint 20, Perkin-Elmer) was added to each reaction well.

Two RNA templates can be used to assay compounds described herein. The cIRES RNA template is 377 nucleotide long and consisting of a partial complementary sequence (36 nucleotides) of the core protein, followed by 341 nucleotide of the complementary sequence of the internal ribosome entry site. The poly A RNA template (GE Amersham catalog number 27-4110) was a homopolymeric RNA pre-annealed to a oligo(rU)16 primer at a molar ratio of 3-to-1 (primer-template). The cIRES template was used in the assay unless otherwise noted.

The amount of light emitted from the scintillant was converted to counts per minute (CPM) on a Topcount® plate reader (Perkin-Elmer, Energy Range: Low, Efficiency Mode Normal, Count Time: 1 min, Background Subtract: none, Cross talk reduction: Off).

Data was analyzed in Excel® (Microsoft®) and Activity-Base® (Idbs®). The reaction in the absence of enzyme was used to determine the background signal, which was subtracted from the enzymatic reactions. Positive control reactions were performed in the absence of compound, from which the background corrected activity was set as 100% polymerase activity. All data was expressed as a percentage of the positive control. The compound concentration at which the enzyme-catalyzed rate of RNA synthesis was reduced by 50% (IC50) was calculated by fitting $$Y = \% \text{ Min} + \frac{(\% \text{ Max} - \% \text{ Min})}{\left[1 + \frac{X}{(IC_{50})S}\right]} \quad \text{(i)}$$

equation (i) to the data where "Y" corresponds to the relative enzyme activity (in %), "% Min" is the residual relative activity at saturating compound concentration, "% Max" is the relative maximum enzymatic activity, "X" corresponds to the compound concentration, and "S" is the Hill coefficient (or slope).

Example 26

HCV Replicon Assay

This assay measures the ability of the compounds of formula I to inhibit HCV RNA replication, and therefore their potential utility for the treatment of HCV infections. The assay utilizes a reporter as a simple readout for intracellular HCV replicon RNA level. The *Renilla luciferase* gene was introduced into the first open reading frame of a genotype 1b replicon construct NK5.1 (N. Krieger et al., *J. Virol.* 2001 75(10):4614), immediately after the internal ribosome entry site (IRES) sequence, and fused with the neomycin phosphotransferase (NPTII) gene via a self-cleavage peptide 2A from foot and mouth disease virus (M. D. Ryan & J. Drew, *EMBO* 1994 13(4):928-933). After in vitro transcription the RNA was electroporated into human hepatoma Huh7 cells, and G418-resistant colonies were isolated and expanded. Stably selected cell line 2209-23 contains replicative HCV subgenomic RNA, and the activity of *Renilla luciferase* expressed by the replicon reflects its RNA level in the cells. The assay was carried out in duplicate plates, one in opaque white and one in transparent, in order to measure the anti-viral activity and cytotoxicity of a chemical compound in parallel ensuring the observed activity is not due to decreased cell proliferation or due to cell death.

HCV replicon cells (2209-23), which express *Renilla luciferase* reporter, were cultured in Dulbecco's MEM (Invitrogen cat no. 10569-010) with 5% fetal bovine serum (FBS, Invitrogen cat. no. 10082-147) and plated onto a 96-well plate at 5000 cells per well, and incubated overnight. Twenty-four hours later, different dilutions of chemical compounds in the growth medium were added to the cells, which were then further incubated at 37° C. for three days. At the end of the incubation time, the cells in white plates were harvested and luciferase activity was measured by using the *R. luciferase* Assay system (Promega cat no. E2820). All the reagents described in the following paragraph were included in the manufacturer's kit, and the manufacturer's instructions were followed for preparations of the reagents. The cells were washed once with 100 µl of phosphate buffered saline (pH 7.0) (PBS) per well and lysed with 20 µl of 1× *R. luciferase* Assay lysis buffer prior to incubation at room temperature for 20 min. The plate was then inserted into the Centro LB 960 microplate luminometer (Berthold Technologies), and 100 µl of *R. luciferase* Assay buffer was injected into each well and the signal measured using a 2-second delay, 2-second measurement program. IC$_{50}$, the concentration of the drug required for reducing replicon level by 50% in relation to the untreated cell control value, can be calculated from the plot of percentage reduction of the luciferase activity vs. drug concentration as described above.

WST-1 reagent from Roche Diagnostic (cat no. 1644807) was used for the cytotoxicity assay. Ten microliter of WST-1 reagent was added to each well of the transparent plates including wells that contain media alone as blanks. Cells were then incubated for 2 h at 37° C., and the OD value was measured using the MRX Revelation microtiter plate reader (Lab System) at 450 nm (reference filter at 650 nm). Again $CC_{50}$, the concentration of the drug required for reducing cell proliferation by 50% in relation to the untreated cell control value, can be calculated from the plot of percentage reduction of the WST-1 value vs. drug concentration as described above.

TABLE II

| Compound Number | HCV Replicon Activity $IC_{50}$ (μM) | Cytotoxic Activity $CC_{50}$ (μM) |
|---|---|---|
| I-78 | 0.078 | 12.4 |
| I-86 | 0.346 | 29.2 |
| I-100 | 0.014 | — |
| I-109 | 0.028 | — |

Example 27

Pharmaceutical compositions of the subject Compounds for administration via several routes were prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:
1. A compound according to formula I

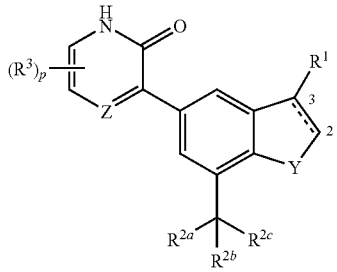

wherein:
the bond between C2 and C3 is either a single or double bond;
Z is N or CH;
$R^1$ is hydrogen, $C_{1-6}$ hydroxyalkyl, —$(CR^7{}_2)_m$COX, —$(CR^7{}_2)_m$CN, $C_{1-3}$ hydroxyalkyl, phenyl or heteroaryl wherein said heteroaryl is pyridinyl, pyrimidinyl, pyrazinyl or pyridazinyl and said phenyl or heteroaryl is optionally independently substituted with one to three substituent selected from the group consisting of hydroxy, $C_{1-6}$ alkoxy, $C_{1-6}$ alkyl, $C_{1-6}$ haloalkyl, $C_{1-6}$ heteroalkyl, $C_{1-3}$ alkoxy-$C_{1-6}$alkyl, —$(CR^7{}_2)_m$NR$^a$R$^b$, cyano, nitro, —$(CR^7{}_2)_m$COR$^4$, —$(CR^7{}_2)_m$SO$_2$NR$^c$R$^d$ and —O$(CR^7{}_2)_m$COR$^4$;
$R^{2a}$, $R^{2b}$ and $R^{2c}$ (i) when taken independently are selected independently from $C_{1-3}$ alkyl, $C_{1-2}$ alkoxy, fluoro or $C_{1-2}$ fluoroalkyl or (ii) when taken together, $R^{2a}$ and $R^{2b}$ together are $C_{2-4}$ methylene and $R^{2c}$ is $C_{1-3}$ alkyl, $C_{1-2}$ alkoxy or $C_{1-2}$ fluoroalkyl;
$R^3$ is independently in each occurrence halogen, $C_{1-3}$ alkyl, $C_{1-3}$ haloalkyl or $C_{1-3}$ alkoxy;
$R^4$ is hydroxy, $C_{1-6}$ alkoxy or NR$^c$R$^d$;
$R^5$ is hydrogen $C_{1-6}$ alkyl, $C_{1-3}$ acyl, $C_{1-3}$ alkylsulfonyl or SO$_2$NR$^i$R$^j$;
$R^7$ is independently in each occurrence hydrogen or $C_{1-3}$ alkyl;
X is hydroxy, $C_{1-6}$ alkoxy, NR$^e$R$^f$, phenyl or heteroaryl wherein said heteroaryl is pyridinyl, thienyl or furanyl and said phenyl and heteroaryl are optionally substituted with one to three substituents independently selected from hydroxyl, $C_{1-3}$ alkyl, $C_{1-3}$ alkoxy or halogen;
$R^a$ and $R^b$ (i) when taken independently are hydrogen, $C_{1-3}$ alkyl, $C_{1-3}$ hydroxyalkyl, $C_{1-3}$ acyl, $C_{1-6}$ alkylsulfonyl, $C_{3-7}$ cycloalkylsulfonyl, —SO$_2$—NR$^e$R$^d$ wherein at least one of R$^a$ and R$^b$ is hydrogen, $C_{1-3}$ hydroxyalkyl or $C_{1-3}$ alkyl, or,
(ii) R$^a$ and R$^b$ when taken together with the nitrogen atom to which they are attached form a pyrrolidine, piperidine or azepine ring said pyrrolidine, piperidine or azepine ring optionally substituted with 1 to 3 groups independently selected from hydroxy, amino, $C_{1-3}$ alkylamine, $C_{1-3}$ dialkylamine, amino-$C_{1-3}$ alkyl, $C_{1-3}$ alkylamine-$C_{1-3}$ alkyl or $C_{1-3}$ dialkylamine-$C_{1-3}$ alkyl, carboxyl, halogen or $C_{1-3}$ alkyl; or,
(iii) R$^a$ and R$^b$ together are $(CH_2)_2X^1(CH_2)_2$;
R$^c$ and R$^d$ (i) when taken independently are hydrogen, $C_{1-3}$ alkyl; or,
(ii) R$^c$ and R$^d$ when taken together along with the nitrogen atom to which they are attached form a pyrrolidine, piperidine or azepine ring; or,
(iii) R$^c$ and R$^d$ together are $(CH_2)_2X^1(CH_2)_2$;
R$^e$ and R$^f$ (i) when taken independently are hydrogen, $C_{1-6}$ alkyl, $C_{1-3}$ alkoxy-$C_{1-3}$ alkyl, $C_{3-7}$ cycloalkyl, phenyl or thiazol-2-yl, said cycloalkyl ring optionally substituted by $C_{1-3}$ hydroxyalkyl, and said phenyl optionally substituted with hydroxy or $(CH_2)_m$NR$^g$R$^h$; or,
(ii) R$^e$ and R$^f$ when taken together along with the nitrogen atom to which they are attached form an azetidine, pyrrolidine, piperidine, azepine, morpholine, pyrazolidin-1-yl, thiazolidin-3-yl, isothiazolidin-2-yl, isoxazolidin-2-yl or oxazolidin-3-yl ring each optionally substituted by one or two groups independently selected in each occurrence from halogen, hydroxy, $C_{1-3}$ alkyl, $C_{1-3}$ hydroxyalkyl, —$(CR^7{}_2)_m$NR$^g$R$^h$, —$(CR^7{}_2)_m$CONR$^g$R$^h$, —$(CR^7{}_2)_m$SO$_2$—$C_{1-3}$ alkyl or —$(CR^7{}_2)_m$COR$^4$; or,
(iii) R$^e$ and R$^f$ together are $(CH_2)_2X^1(CH_2)_2$ or [1,4] diazepam-1-yl optionally substituted with $C_{1-3}$ hydroxyalkyl, $(CR^7{}_2)_m$NR$^g$R$^h$ or $C_{1-3}$ alkyl;
R$^g$ and R$^h$ (i) when taken independently are hydrogen, $C_{1-6}$ alkyl, $C_{1-6}$ haloalkyl, $C_{1-6}$ acyl, $C_{1-6}$ haloalkylcarbonyl, $C_{1-6}$ alkylsulfonyl, $C_{1-6}$ haloalkylsulfonyl, $C_{3-7}$ cycloalkylsulfonyl, phenylsulfonyl, —SO$_2$—NR$^i$R$^j$, or $C_{1-6}$ alkoxycarbonyl; or,
(ii) R$^g$ and R$^h$ taken together are $(CH_2)_2X^2(CH_2)_2$ optionally substituted with $C_{1-3}$ hydroxyalkyl;
R$_i$ and R$^j$ are independently hydrogen or $C_{1-3}$ alkyl;
$X^1$ is independently S(O)$_n$ or NR$^5$;
$X^2$ are independently O, S(O)$_n$ or NR$^5$;
Y is O, S or NR$^7$, with the proviso that when the bond between C2 and C3 is a single bond, Y is O;
m is independently in each occurrence zero to three;
n is zero to two;
p is zero to two; or,
pharmaceutically acceptable salts thereof.

2. A compound according to claim 1 wherein Y is O and Z is CH.

3. A compound according to claim 2 wherein:
the bond between C2 and C3 is a double bond;
$R^1$ is —$(CR^7{}_2)_m$COX wherein m is zero;
X is NR$^e$R$^f$;
R$^e$ and R$^f$ together with the nitrogen to which they are attached are piperidine, pyrrolidine or morpholine each optionally substituted by $(CR^7{}_2)_m$NR$^g$R$^h$ wherein m is zero or one and R$^7$ is in each occurrence hydrogen;
n and p are zero or one;
R$^g$ is hydrogen or $C_{1-3}$ alkyl; and,
R$^h$ is hydrogen, $C_{1-3}$ alkyl, $C_{1-3}$ alkylsulfonyl, cyclopropylsulfonyl or SO$_2$NR$^i$R$^j$ wherein R$^i$ and R$^j$ are independently hydrogen or $C_{1-3}$ alkyl.

4. A compound according to claim 2 wherein $R^{2a}$, $R^{2b}$ and $R^{2c}$ are methyl, $R^3$ is halogen or $C_{1-3}$ alkyl and p is one.

5. A compound according to claim 3 wherein R$^e$ and R$^f$ together with the nitrogen to which they are attached are piperidinyl, pyrrolidinyl or morpholinyl substituted by $(CR^7{}_2)_m$NR$^g$R$^h$ wherein m is zero or one and R$^7$ is, in each occurrence, hydrogen; R$^g$ is hydrogen and R$^h$ is $C_{1-3}$ alkylsulfonyl or cyclopropylsulfonyl.

6. A compound according to claim 2 wherein the bond between C2 and C3 is a double bond and $R^1$ is optionally substituted phenyl or pyridinyl.

7. A compound according to claim 6 wherein $R^1$ is phenyl or pyridinyl substituted by:
(a) —$(CR^7{}_2)_m$NR$^a$R$^b$; R$^a$ is hydrogen, $C_{1-3}$ alkyl or $C_{1-3}$ hydroxyalkyl and R$^h$ is hydrogen, $C_{1-3}$ alkyl or $C_{1-3}$ alkylsulfonyl or cyclopropylsulfonyl; or,
(b) —$(CR^7{}_2)_m$COR$^4$ and R$^4$ is NR$^c$R$^d$;

wherein m is zero or one and $R^7$ is, in each occurrence, hydrogen.

8. A compound according to claim 6 wherein $R^1$ is phenyl or pyridinyl either optionally substituted by a one to three substituents independently selected from the group consisting of hydroxy, $C_{1-6}$ alkoxy, cyano and —O(CR$^7_2$)$_m$COR$^4$ wherein m is zero or one and $R^7$ is, in each occurrence, hydrogen.

9. A compound according to claim 1 wherein Y is $NR^7$ and $R^7$ is $C_{1-3}$ alkyl.

10. A compound according to claim 9 wherein:
$R^1$ is —(CR$^7_2$)$_m$COX wherein m is zero or one and $R^7$ is, in each occurrence, hydrogen;
X is $NR^eR^f$;
$R^e$ and $R^f$ together with the nitrogen to which they are attached are piperidine, pyrrolidine or morpholine each optionally substituted by (CR$^7_2$)$_m$NR$^g$R$^h$;
p is zero or one;
$R^g$ is hydrogen or $C_{1-3}$ alkyl; and,
$R^h$ is hydrogen, $C_{1-3}$ alkyl, $C_{1-3}$ alkylsulfonyl, cyclopropylsulfonyl or SO$_2$NR$^i$R$^j$ wherein $R^i$ and $R^j$ are independently hydrogen, $C_{1-3}$ alkyl.

11. A compound according to claim 1 which compound is selected from the group consisting of:
[7-tert-butyl-5-(2-oxo-1,2-dihydro-pyridin-3-yl)-benzofuran-3-yl]-acetonitrile;
[7-tert-butyl-5-(2-oxo-1,2-dihydro-pyridin-3-yl)-benzofuran-3-yl]-acetic acid;
3-[7-tert-butyl-3-(morpholine-4-carbonyl)-benzofuran-5-yl]-1H-pyridin-2-one;
3-(7-tert-butyl-3-hydroxymethyl-benzofuran-5-yl)-1H-pyridin-2-one;
7-tert-butyl-5-(2-oxo-1,2-dihydro-pyridin-3-yl)-benzofuran-3-carboxylic acid isopropylamide;
7-tert-butyl-5-(2-oxo-1,2-dihydro-pyridin-3-yl)-benzofuran-3-carboxylic acid isobutyl-amide;
7-tert-butyl-5-(2-oxo-1,2-dihydro-pyridin-3-yl)-benzofuran-3-carboxylic acid isobutyl-methyl-amide;
3-[7-tert-butyl-3-(4-hydroxy-piperidine-1-carbonyl)-benzofuran-5-yl]-1H-pyridin-2-one;
3-[7-tert-butyl-3-(piperidine-1-carbonyl)-benzofuran-5-yl]-1H-pyridin-2-one;
3-[7-tert-butyl-3-(3-hydroxymethyl-piperidine-1-carbonyl)-benzofuran-5-yl]-1H-pyridin-2-one;
3-[7-tert-butyl-3-(2-hydroxymethyl-morpholine-4-carbonyl)-benzofuran-5-yl]-1H-pyridin-2-one;
3-[7-tert-butyl-3-((R)-2-hydroxymethyl-pyrrolidine-1-carbonyl)-benzofuran-5-yl]-1H-pyridin-2-one;
3-[7-tert-butyl-3-((S)-2-hydroxymethyl-pyrrolidine-1-carbonyl)-benzofuran-5-yl]-1H-pyridin-2-one;
7-tert-butyl-5-(2-oxo-1,2-dihydro-pyridin-3-yl)-benzofuran-3-carboxylic acid (1-hydroxymethyl-cyclopentyl)-amide;
7-tert-butyl-5-(2-oxo-1,2-dihydro-pyridin-3-yl)-benzofuran-3-carboxylic acid bis-(2-methoxy-ethyl)-amide;
3-(3-benzoyl-7-tert-butyl-benzofuran-5-yl)-1H-pyridin-2-one;
7-tert-butyl-5-(2-oxo-1,2-dihydro-pyridin-3-yl)-benzofuran-3-carboxylic acid (3-hydroxy-phenyl)-amide;
7-tert-butyl-5-(2-oxo-1,2-dihydro-pyridin-3-yl)-benzofuran-3-carboxylic acid methylamide;
7-tert-butyl-5-(2-oxo-1,2-dihydro-pyridin-3-yl)-benzofuran-3-carboxylic acid phenylamide;
3-(7-tert-butyl-3-phenyl-benzofuran-5-yl)-1H-pyridin-2-one;
7-tert-butyl-5-(2-oxo-1,2-dihydro-pyridin-3-yl)-benzofuran-3-carboxylic acid ethyl-(2-methoxy-ethyl)-amide;
7-tert-butyl-5-(2-oxo-1,2-dihydro-pyridin-3-yl)-2,3-dihydro-benzofuran-3-carboxylic acid methyl ester;
3-[7-tert-butyl-3-(3-hydroxy-piperidine-1-carbonyl)-benzofuran-5-yl]-1H-pyridin-2-one;
3-[3-(4-amino-piperidine-1-carbonyl)-7-tert-butyl-benzofuran-5-yl]-1H-pyridin-2-one;
3-[3-(4-amino-piperidine-1-carbonyl)-7-tert-butyl-benzofuran-5-yl]-1H-pyridin-2-one;
3-[7-tert-butyl-3-(3-methoxy-benzoyl)-benzofuran-5-yl]-1H-pyridin-2-one;
3-[7-tert-butyl-3-(3-methyl-thiophene-2-carbonyl)-benzofuran-5-yl]-1H-pyridin-2-one;
3-[7-tert-butyl-5-(2-oxo-1,2-dihydro-pyridin-3-yl)-benzofuran-3-yl]-benzonitrile;
3-[7-tert-butyl-3-(3-methoxy-phenyl)-benzofuran-5-yl]-1H-pyridin-2-one;
3-[7-tert-butyl-3-(3-hydroxy-phenyl)-benzofuran-5-yl]-1H-pyridin-2-one;
4-[7-tert-butyl-5-(2-oxo-1,2-dihydro-pyridin-3-yl)-benzofuran-3-yl]-benzonitrile;
3-[7-tert-butyl-3-(3-hydroxy-benzoyl)-benzofuran-5-yl]-1H-pyridin-2-one;
N-{4-[7-tert-butyl-5-(2-oxo-1,2-dihydro-pyridin-3-yl)-benzofuran-3-yl]-benzyl}-methanesulfonamide;
{(R)-1-[7-tert-butyl-5-(2-oxo-1,2-dihydro-pyridin-3-yl)-benzofuran-3-carbonyl]-piperidin-3-yl}-carbamic acid tert-butyl ester;
{1-[7-tert-butyl-5-(2-oxo-1,2-dihydro-pyridin-3-yl)-benzofuran-3-carbonyl]-piperidin-4-yl}-carbamic acid tert-butyl ester;
{(S)-1-[7-tert-butyl-5-(2-oxo-1,2-dihydro-pyridin-3-yl)-benzofuran-3-carbonyl]-piperidin-3-yl}-carbamic acid tert-butyl ester;
3-[3-((S)-3-amino-piperidine-1-carbonyl)-7-tert-butyl-benzofuran-5-yl]-1H-pyridin-2-one;
3-[3-((R)-3-amino-piperidine-1-carbonyl)-7-tert-butyl-benzofuran-5-yl]-1H-pyridin-2-one;
{1-[7-tert-butyl-5-(2-oxo-1,2-dihydro-pyridin-3-yl)-benzofuran-3-carbonyl]-piperidin-3-ylmethyl}-carbamic acid tert-butyl ester;
{1-[7-tert-butyl-5-(2-oxo-1,2-dihydro-pyridin-3-yl)-benzofuran-3-carbonyl]-pyrrolidin-3-ylmethyl}-carbamic acid tert-butyl ester;
N-{(R)-1-[7-tert-butyl-5-(2-oxo-1,2-dihydro-pyridin-3-yl)-benzofuran-3-carbonyl]-piperidin-3-yl}-methanesulfonamide;
N-{(S)-1-[7-tert-butyl-5-(2-oxo-1,2-dihydro-pyridin-3-yl)-benzofuran-3-carbonyl]-piperidin-3-yl}-methanesulfonamide;
3-[3-(3-amino-pyrrolidine-1-carbonyl)-7-tert-butyl-benzofuran-5-yl]-1H-pyridin-2-one;
3-[3-(3-aminomethyl-pyrrolidine-1-carbonyl)-7-tert-butyl-benzofuran-5-yl]-1H-pyridin-2-one;
3-[3-(3-aminomethyl-piperidine-1-carbonyl)-7-tert-butyl-benzofuran-5-yl]-1H-pyridin-2-one
3-[7-tert-butyl-3-(pyrrolidine-1-carbonyl)-benzofuran-5-yl]-1H-pyridin-2-one;
3-[3-(4-acetyl-piperazine-1-carbonyl)-7-tert-butyl-benzofuran-5-yl]-1H-pyridin-2-one;
3-[7-tert-butyl-3-((S)-3-dimethylamino-pyrrolidine-1-carbonyl)-benzofuran-5-yl]-1H-pyridin-2-one; compound with formic acid;
3-[7-tert-butyl-3-(4-methyl-[1,4]diazepane-1-carbonyl)-benzofuran-5-yl]-1H-pyridin-2-one; compound with formic acid;

N-{1-[7-tert-butyl-5-(2-oxo-1,2-dihydro-pyridin-3-yl)-benzofuran-3-carbonyl]-piperidin-4-yl}-2,2,2-trifluoro-acetamide;

1-[7-tert-butyl-5-(2-oxo-1,2-dihydro-pyridin-3-yl)-benzofuran-3-carbonyl]-piperidine-4-carboxylic acid amide;

3-[3-(4-aminomethyl-phenyl)-7-tert-butyl-benzofuran-5-yl]-1H-pyridin-2-one;

N-{1-[7-tert-butyl-5-(2-oxo-1,2-dihydro-pyridin-3-yl)-benzofuran-3-carbonyl]-pyrrolidin-3-yl}-2,2,2-trifluoro-acetamide;

1-[7-tert-butyl-5-(2-oxo-1,2-dihydro-pyridin-3-yl)-benzofuran-3-carbonyl]-piperidine-3-carboxylic acid amide;

3-[3-(3-aminomethyl-phenyl)-7-tert-butyl-benzofuran-5-yl]-1H-pyridin-2-one;

(2S,4R)-1-[7-tert-butyl-5-(2-oxo-1,2-dihydro-pyridin-3-yl)-benzofuran-3-carbonyl]-4-hydroxy-pyrrolidine-2-carboxylic acid methyl ester;

1-[7-tert-butyl-5-(2-oxo-1,2-dihydro-pyridin-3-yl)-benzofuran-3-carbonyl]-4-hydroxy-piperidine-4-carboxylic acid amide;

3-[7-tert-butyl-3-(3-hydroxy-pyrrolidine-1-carbonyl)-benzofuran-5-yl]-1H-pyridin-2-one;

1-[7-tert-butyl-5-(2-oxo-1,2-dihydro-pyridin-3-yl)-benzofuran-3-carbonyl]-4-ethylamino-piperidine-4-carboxylic acid amide; formate salt;

3-[7-tert-butyl-3-((R)-3-dimethylamino-pyrrolidine-1-carbonyl)-benzofuran-5-yl]-1H-pyridin-2-one; formate salt;

3-[7-tert-butyl-3-(4,4-difluoro-piperidine-1-carbonyl)-benzofuran-5-yl]-1H-pyridin-2-one;

3-[7-tert-butyl-3-(3,3-dimethyl-piperidine-1-carbonyl)-benzofuran-5-yl]-1H-pyridin-2-one;

3-[7-tert-butyl-3-(3-hydroxymethyl-pyrrolidine-1-carbonyl)-benzofuran-5-yl]-1H-pyridin-2-one;

3-[7-tert-butyl-3-(thiazolidine-3-carbonyl)-benzofuran-5-yl]-1H-pyridin-2-one;

N-{(S)-1-[7-tert-butyl-5-(2-oxo-1,2-dihydro-pyridin-3-yl)-benzofuran-3-carbonyl]-pyrrolidin-3-ylmethyl}-methanesulfonamide;

N-{(R)-1-[7-tert-butyl-5-(2-oxo-1,2-dihydro-pyridin-3-yl)-benzofuran-3-carbonyl]-pyrrolidin-3-ylmethyl}-methanesulfonamide;

N-{4-[7-tert-butyl-5-(5-fluoro-2-oxo-1,2-dihydro-pyridin-3-yl)-benzofuran-3-yl]-benzyl}-methanesulfonamide;

N-{(R)-1-[7-tert-butyl-5-(2-oxo-1,2-dihydro-pyridin-3-yl)-benzofuran-3-carbonyl]-pyrrolidin-3-ylmethyl}-acetamide;

N-{4-[7-tert-butyl-5-(2-oxo-1,2-dihydro-pyridin-3-yl)-benzofuran-3-yl]-benzyl}-N-(2-hydroxy-ethyl)-methanesulfonamide;

N-{4-[7-tert-butyl-5-(2-oxo-1,2-dihydro-pyridin-3-yl)-benzofuran-3-yl]-benzyl}-N-methyl-methanesulfonamide;

3-[7-tert-butyl-5-(2-oxo-1,2-dihydro-pyridin-3-yl)-benzofuran-3-yl]-benzamide

N-{4-[7-tert-butyl-5-(2-oxo-1,2-dihydro-pyridin-3-yl)-benzofuran-3-yl]-phenyl}-methanesulfonamide;

N-{4-[7-tert-butyl-5-(2-oxo-1,2-dihydro-pyridin-3-yl)-benzofuran-3-yl]-phenyl}-acetamide;

N-{3-[7-tert-butyl-5-(2-oxo-1,2-dihydro-pyridin-3-yl)-benzofuran-3-yl]-benzyl}-methanesulfonamide;

N-{3-[7-tert-butyl-5-(2-oxo-1,2-dihydro-pyridin-3-yl)-benzofuran-3-yl]-phenyl}-methanesulfonamide;

7-tert-butyl-5-(2-oxo-1,2-dihydro-pyridin-3-yl)-benzofuran-3-carboxylic acid (3-methanesulfonylamino-phenyl)-amide;

7-tert-butyl-5-(2-oxo-1,2-dihydro-pyridin-3-yl)-benzofuran-3-carboxylic acid thiazol-2-ylamide;

7-tert-butyl-5-(2-oxo-1,2-dihydro-pyridin-3-yl)-benzofuran-3-carboxylic acid [3-(methanesulfonylamino-methyl)-phenyl]-amide;

3-[3-(4-amino-phenyl)-7-tert-butyl-benzofuran-5-yl]-1H-pyridin-2-one;

4-[7-tert-butyl-5-(2-oxo-1,2-dihydro-pyridin-3-yl)-benzofuran-3-yl]-benzamide;

N-(1-{4-[7-tert-butyl-5-(2-oxo-1,2-dihydro-pyridin-3-yl)-benzofuran-3-yl]-phenyl}-ethyl)-methanesulfonamide;

3-[3-(2-amino-pyrimidin-5-yl)-7-tert-butyl-benzofuran-5-yl]-1H-pyridin-2-one;

N-{1-[7-tert-butyl-5-(2-oxo-1,2-dihydro-pyridin-3-yl)-benzofuran-3-carbonyl]-piperidin-3-ylmethyl}-methanesulfonamide;

3-[7-tert-butyl-3-(5-methyl-pyridin-2-yl)-benzofuran-5-yl]-1H-pyridin-2-one;

N-{(S)-1-[7-tert-butyl-5-(5-fluoro-2-oxo-1,2-dihydro-pyridin-3-yl)-benzofuran-3-carbonyl]-pyrrolidin-3-ylmethyl}-methanesulfonamide;

N-{5-[7-tert-butyl-5-(2-oxo-1,2-dihydro-pyridin-3-yl)-benzofuran-3-yl]-pyridin-2-ylmethyl}-methanesulfonamide;

3-[3-(azetidine-1-carbonyl)-7-tert-butyl-benzofuran-5-yl]-1H-pyridin-2-one;

3-[7-tert-butyl-3-(3-hydroxymethyl-azetidine-1-carbonyl)-benzofuran-5-yl]-1H-pyridin-2-one;

3-[3-(6-amino-pyridin-3-yl)-7-tert-butyl-benzofuran-5-yl]-1H-pyridin-2-one;

N-{4-[7-tert-butyl-5-(2-oxo-1,2-dihydro-pyridin-3-yl)-benzofuran-3-yl]-3-methoxymethyl-benzyl}-methanesulfonamide;

N-{(S)-1-[7-tert-butyl-5-(6-methyl-2-oxo-1,2-dihydro-pyridin-3-yl)-benzofuran-3-carbonyl]-pyrrolidin-3-ylmethyl}-methanesulfonamide;

N-{1-[7-tert-butyl-5-(2-oxo-1,2-dihydro-pyridin-3-yl)-benzofuran-3-carbonyl]-piperidin-4-yl}-methanesulfonamide;

N-{(S)-1-[7-tert-butyl-5-(2-oxo-1,2-dihydro-pyridin-3-yl)-benzofuran-3-carbonyl]-piperidin-3-ylmethyl}-methane sulfonamide;

N-{(R)-1-[7-tert-butyl-5-(2-oxo-1,2-dihydro-pyridin-3-yl)-benzofuran-3-carbonyl]-piperidin-3-ylmethyl}-methanesulfonamide;

3-[7-tert-butyl-3-(3-hydroxy-azetidine-1-carbonyl)-benzofuran-5-yl]-1H-pyridin-2-one;

N-{[7-tert-butyl-5-(2-oxo-1,2-dihydro-pyridin-3-yl)-benzofuran-3-carbonyl]-azetidin-3-ylmethyl}-methanesulfonamide;

N-{1-[7-tert-butyl-5-(2-oxo-1,2-dihydro-pyridin-3-yl)-benzofuran-3-carbonyl]-piperidin-3-ylmethyl}-N-methyl-methanesulfonamide;

N-{(S)-1-[7-tert-butyl-5-(2-oxo-1,2-dihydro-pyridin-3-yl)-benzofuran-3-carbonyl]-pyrrolidin-3-ylmethyl}-N-methyl-methanesulfonamide;

ethanesulfonic acid {(S)-1-[7-tert-butyl-5-(2-oxo-1,2-dihydro-pyridin-3-yl)-benzofuran-3-carbonyl]-pyrrolidin-3-ylmethyl}-amide;

cyclopropanesulfonic acid {(S)-1-[7-tert-butyl-5-(2-oxo-1,2-dihydro-pyridin-3-yl)-benzofuran-3-carbonyl]-pyrrolidin-3-ylmethyl}-amide;

propane-2-sulfonic acid {(S)-1-[7-tert-butyl-5-(2-oxo-1,2-dihydro-pyridin-3-yl)-benzofuran-3-carbonyl]-pyrrolidin-3-ylmethyl}-amide; or, N-{4-[7-tert-butyl-5-(2-oxo-1,2-dihydro-pyridin-3-yl)-benzofuran-3-carbonyl]-morpholin-2-ylmethyl}-methanesulfonamide;

7-tert-Butyl-1-methyl-5-(2-oxo-1,2-dihydro-pyridin-3-yl)-1H-indole-3-carbonitrile;

N-{(S)-1-[7-tert-Butyl-1-methyl-5-(2-oxo-1,2-dihydropyridin-3-yl)-1H-indole-3-carbonyl]-pyrrolidin-3-ylmethyl}-methanesulfonamide; and, 7-tert-Butyl-1-methyl-5-(2-oxo-1,2-dihydro-pyridin-3-yl)-1H-indole-3-carboxylic acid amide; or, a pharmaceutically acceptable salt thereof.

12. A pharmaceutical composition comprising a therapeutically effective quantity of a compound according to claim 1 admixed with at least one pharmaceutically acceptable carrier, diluent or excipient.

* * * * *